(12) United States Patent
Bakker et al.

(10) Patent No.: US 9,260,724 B2
(45) Date of Patent: *Feb. 16, 2016

(54) OPTIMIZATION OF EXPRESSION OF PARVOVIRAL REP AND CAP PROTEINS IN INSECT CELLS

(71) Applicant: uniQure IP B.V., Amsterdam (NL)

(72) Inventors: Andrew Christian Bakker, Almere (NL); Wilhelmus Theodorus Johannes Maria Christiaan Maria Christ Hermens, Almere (NL); Yvet Noordman, Utrecht (NL)

(73) Assignee: UNIQURE IP B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/149,953

(22) Filed: Jan. 8, 2014

(65) Prior Publication Data

US 2014/0127801 A1    May 8, 2014

Related U.S. Application Data

(63) Continuation of application No. 12/918,460, filed as application No. PCT/NL2009/050076 on Feb. 19, 2009, now Pat. No. 8,642,314.

(60) Provisional application No. 61/029,673, filed on Feb. 19, 2008.

(30) Foreign Application Priority Data

Feb. 19, 2008    (EP) .................................. 08151634

(51) Int. Cl.
```
C12N 7/00      (2006.01)
C12N 15/86     (2006.01)
C07K 14/005    (2006.01)
```

(52) U.S. Cl.
CPC .............. *C12N 15/86* (2013.01); *C07K 14/005* (2013.01); *C12N 7/00* (2013.01); *C12N 2710/14143* (2013.01); *C12N 2750/14122* (2013.01); *C12N 2750/14243* (2013.01); *C12N 2800/105* (2013.01); *C12N 2800/50* (2013.01)

(58) Field of Classification Search
CPC .................................. C12N 7/00; C12N 15/86
USPC ............................................ 435/235.1, 320.1
See application file for complete search history.

(56) References Cited

U.S. PATENT DOCUMENTS

| | | | |
|---|---|---|---|
| 6,723,551 B2 | 4/2004 | Kotin et al. | |
| 8,642,314 B2 * | 2/2014 | Bakker et al. | 435/235.1 |
| 2003/0148506 A1 * | 8/2003 | Kotin et al. | 435/320.1 |
| 2009/0191588 A1 | 7/2009 | Hermens et al. | |
| 2009/0191597 A1 | 7/2009 | Samulski et al. | |
| 2009/0203071 A1 | 8/2009 | Chen | |

FOREIGN PATENT DOCUMENTS

| | | | |
|---|---|---|---|
| WO | WO03/042361 A2 | 5/2003 | |
| WO | WO 2007046703 A2 * | 4/2007 | |
| WO | WO2007084773 A2 | 7/2007 | |
| WO | WO2007148971 A2 | 12/2007 | |
| WO | WO2008024998 A2 | 2/2008 | |

OTHER PUBLICATIONS

Habib et al.; Bifunctionality of the AcMNPV Homologous Region Sequence (hrl): Enhancer and ori Functions Have Different Sequence Requirements; DNA and Cell Biology; vol. 15, No. 9, (1996); pp. 737-747.*
Aucoin et al., "Production of adeno-associated viral vectors in insect cells using triple infection: optimization of baculovirus concentration ratios," Biotechnology and Bioengineering, 2006, 95:1081-1092.
Urabe et al.,"Insect cells as a factory to produce adeno-associated virus type 2 vectors," Human Gene Therapy, 2002, 13:1935-1943.
Kohlbrenner et al., "Successful Production of Pseudotyped rAAV Vectors Using a Modified Baculovirus Expression System," Molecular Therapy, 2005, '12:217-1225.
Huang et al.,"Combination of baculovirus-mediated gene delivery and packed-bed reactor for scalable production of adeno-associated virus," Human Gene Therapy 18:1161-1170.

* cited by examiner

*Primary Examiner* — Antonio Galisteo Gonzalez
(74) *Attorney, Agent, or Firm* — Browdy and Neimark, PLLC

(57) ABSTRACT

The present invention relates to the improved production of recombinant parvoviral virions in insect cells. In particular, the invention relates to an improved process for the production of recombinant parvoviral virions in insect cells, wherein the full/empty parvoviral virion ratio is increased. The invention also relates to the production of parvoviral vectors that may be used in gene therapy and to improvements in expression of the viral Rep proteins that increase the productivity of parvoviral vectors.

25 Claims, 11 Drawing Sheets

SEQUENCE LISTING

```
<160> NUMBER OF SEQ ID NOS: 31

<210> SEQ ID NO 1
<211> LENGTH: 1194
<212> TYPE: DNA
<213> ORGANISM: adeno-associated virus 2
<220> FEATURE:
<221> NAME/KEY: misc_feature
<222> LOCATION: (1)..(1194)
<223> OTHER INFORMATION: rep52 wild type

<400> SEQUENCE: 1
atggagctgg tcgggtggct cgtggacaag gggattacct cggagaagca gtggatccag      60
gaggaccagg cctcatacat ctccttcaat gcggcctcca actcgcggtc ccaaatcaag     120
gctgccttgg acaatgcggg aaagattatg agcctgacta aaaccgcccc cgactacctg     180
gtgggccagc agcccgtgga ggacatttcc agcaatcgga tttataaaat tttggaacta     240
aacgggtacg atccccaata tgcggcttcc gtctttctgg gatgggccac gaaaaagttc     300
ggcaagagga acaccatctg gctgtttggg cctgcaacta ccgggaagac caacatcgcg     360
gaggccatag cccacactgt gcccttctac gggtgcgtaa actggaccaa tgagaactt     420 cccttcaacg actgtgtcga caagatggtg atctggtggg aggaggggaa gatgaccgcc     480
aaggtcgtgg agtcggccaa agccattctc ggaggaagca aggtgcgcgt ggaccagaaa     540
tgcaagtcct cggcccagat agacccgact cccgtgatcg tcacctccaa caccaacatg     600
tgcgccgtga ttgacgggaa ctcaacgacc ttcgaacacc agcagccgtt gcaagaccgg     660
atgttcaaat ttgaactcac ccgccgtctg gatcatgact tgggaaggt caccaagcag     720 gaagtcaaag acttttttcg gtgggcaaag gatcacgtgt tgaggtgga gcatgaattc     780 tacgtcaaaa agggtggagc caagaaaaga cccgccccca gtgacgcaga tataagtgag     840
cccaaacggg tgcgcgagtc agttgcgcag ccatcgacgt cagacgcgga agcttcgatc     900
aactacgcag accgctacca aaacaaatgt tctcgtcacg tgggcatgaa tctgatgctg     960
tttccctgca gacaatgcga gagaatgaat cagaattcaa atatctgctt cactcacgga    1020
```

-continued

```
cagaaagact gtttagagtg ctttcccgtg tcagaatctc aacccgtttc tgtcgtcaaa    1080
aaggcgtatc agaaactgtg ctacattcat catatcatgg gaaaggtgcc agacgcttgc    1140
actgcctgcg atctggtcaa tgtggatttg gatgactgca tctttgaaca ataa          1194
```

<210> SEQ ID NO 2
<211> LENGTH: 1194
<212> TYPE: DNA
<213> ORGANISM: adeno-associated virus 2
<220> FEATURE:
<221> NAME/KEY: misc_feature
<222> LOCATION: (1)..(1194)
<223> OTHER INFORMATION: rep52 sf9 (insect cell) optimised

<400> SEQUENCE: 2

```
atggagctgg tgggttggct ggtggacaag ggtatcacct ccgagaagca gtggatccag      60
gaggaccagg cttcctacat ctccttcaac gctgcttcca ctcccgttc ccagatcaag     120 gctgctctgg acaacgctgg taagatcatg tccctgacca agaccgctcc tgactacctg    180
gtgggtcagc agcctgtgga ggacatctcc tccaaccgta tctacaagat cctggagctg    240
aacggttacg accctcagta cgctgcttcc gtgttcctgg ttgggctac caagaagttc     300 ggtaagcgta acaccatctg gctgttcggt cctgctacca ccggtaagac caacatcgct    360
gaggctatcg ctcacaccgt gcctttctac ggttgcgtga actggaccaa cgagaacttc    420
cctttcaacg actgcgtgga caagatggtg atctggtggg aggagggtaa gatgaccgct    480
aaggtggtgg agtccgctaa ggctatcctg gtggttcca aggtgcgtgt ggaccagaag     540
tgcaagtcct ccgctcagat cgaccctacc cctgtgatcg tgacctccaa caccaacatg    600
tgcgctgtga tcgacggtaa ctccaccacc ttcgagcacc agcagcctct gcaggaccgt    660
atgttcaagt tcgagctgac ccgtcgtctg gaccacgact tcggtaaggt gaccaagcag    720
gaggtgaagg acttcttccg ttgggctaag gaccacgtgg tggaggtgga gcacgagttc    780
tacgtgaaga agggtggtgc taagaagcgt cctgctcctt ccgacgctga catctccgag    840
cctaagcgtg tgcgtgagtc cgtggctcag ccttccacct ccgacgctga ggcttccatc    900
aactacgctg accgttacca gaacaagtgc tcccgtcacg tgggtatgaa cctgatgctg    960
ttcccttgcc gtcagtgcga gcgtatgaac cagaactcca acatctgctt cacccacggt   1020
cagaaggact gcctggagtg cttccctgtg tccgagtccc agcctgtgtc cgtggtgaag   1080
aaggcttacc agaagctgtg ctacatccac cacatcatgg gtaaggtgcc tgacgcttgc   1140
accgcttgcg acctggtgaa cgtggacctg gacgactgca tcttcgagca gtaa          1194
```

<210> SEQ ID NO 3
<211> LENGTH: 1194
<212> TYPE: DNA
<213> ORGANISM: adeno-associated virus 2
<220> FEATURE:
<221> NAME/KEY: misc_feature
<222> LOCATION: (1)..(1194)
<223> OTHER INFORMATION: rep52 AT optimised

<400> SEQUENCE: 3

```
atggaattag taggatggtt agtagataaa ggaataacat cagaaaaaca atggatacaa      60
gaagatcaag catcatatat atcatttaat gcagcatcaa attcaagatc acaaataaaa    120
gcagcattag ataatgcagg aaaaataatg tcattaacaa aaacagcacc agattattta    180
gtaggacaac aaccagtaga agatatatca tcaaatagaa tatataaaat attagaatta    240
```

| | |
|---|---|
| aatggatatg atccacaata tgcagcatca gtatttttag gatgggcaac aaaaaaattt | 300 |
| ggaaaaagaa atacaatatg gttatttgga ccagcaacaa caggaaaaac aaatatagca | 360 |
| gaagcaatag cacatacagt accattttat ggatgtgtaa attggacaaa tgaaaatttt | 420 |
| ccatttaatg attgtgtaga taaaatggta atatggtggg aagaaggaaa atgacagca | 480 |
| aaagtagtag aatcagcaaa agcaatatta ggaggatcaa aagtaagagt agatcaaaaa | 540 |
| tgtaaatcat cagcacaaat agatccaaca ccagtaatag taacatcaaa tacaaatatg | 600 |
| tgtgcagtaa tagatggaaa ttcaacaaca tttgaacatc aacaaccatt acaagataga | 660 |
| atgtttaaat ttgaattaac aagaagatta gatcatgatt ttggaaaagt aacaaaacaa | 720 |
| gaagtaaaag atttttttag atgggcaaaa gatcatgtag tagaagtaga acatgaattt | 780 |
| tatgtaaaaa aaggaggagc aaaaaaaaga ccagcaccat cagatgcaga tatatcagaa | 840 |
| ccaaaaagag taagagaatc agtagcacaa ccatcaacat cagatgcaga agcatcaata | 900 |
| aattatgcag atagatatca aaataaatgt tcaagacatg taggaatgaa tttaatgtta | 960 |
| tttccatgta gacaatgtga agaatgaat caaaattcaa atatatgttt tacacatgga | 1020 |
| caaaaagatt gtttagaatg ttttccagta tcagaatcac aaccagtatc agtagtaaaa | 1080 |
| aaagcatatc aaaaattatg ttatatacat catataatgg gaaaagtacc agatgcatgt | 1140 |
| acagcatgtg atttagtaaa tgtagattta gatgattgta tatttgaaca ataa | 1194 |

<210> SEQ ID NO 4
<211> LENGTH: 1194
<212> TYPE: DNA
<213> ORGANISM: adeno-associated virus 2
<220> FEATURE:
<221> NAME/KEY: misc_feature
<222> LOCATION: (1)..(1194)
<223> OTHER INFORMATION: rep52 GC optimised

<400> SEQUENCE: 4

| | |
|---|---|
| atggagctgg tggggtggct ggtggacaag gggatcacga gcgagaagca gtggatccag | 60 |
| gaggaccagg cgagctacat cagcttcaac gcggcgagca acagccggag ccagatcaag | 120 |
| gcggcgctga caacgcgggg aagatcatg agcctgacga gacggcgcc ggactacctg | 180 |
| gtggggcagc agccggtgga ggacatcagc agcaaccgga tctacaagat cctggagctg | 240 |
| aacgggtacg acccgcagta cgcggcgagc gtgttcctgg gtgggcgac gaagaagttc | 300 |
| gggaagcgga acacgatctg gctgttcggg ccggcgacga cggggaagac gaacatcgcg | 360 |
| gaggcgatcg cgcacacggt gccgttctac ggtgcgtga actggacgaa cgagaacttc | 420 |
| ccgttcaacg actgcgtgga caagatggtg atctggtggg aggagggaa gatgacggcg | 480 |
| aaggtggtgg agagcgcgaa ggcgatcctg ggggggagca aggtgcgggt ggaccagaag | 540 |
| tgcaagagca gcgcgcagat cgacccgacg ccggtgatcg tgacgagcaa cacgaacatg | 600 |
| tgcgcggtga tcgacgggaa cagcacgacg ttcgagcacc agcagccgct gcaggaccgg | 660 |
| atgttcaagt tcgagctgac gcggcggctg gaccacgact cgggaaggt gacgaagcag | 720 |
| gaggtgaagg acttcttccg gtgggcgaag gaccacgtgg tggaggtgga gcacgagttc | 780 |
| tacgtgaaga aggggggggc gaagaagcgg ccggcgccga cgacgcgga catcagcgag | 840 |
| ccgaagcggg tgcgggagag cgtggcgcag ccgagcacga cgcgacgcgga ggcgagcatc | 900 |
| aactacgcgg accggtacca gaacaagtgc agcggcacg tggggatgaa cctgatgctg | 960 |
| ttcccgtgcc ggcagtgcga gcggatgaac cagaacagca acatctgctt cacgcacggg | 1020 |
| cagaaggact gcctggagtg cttcccggtg agcgagagcc agccggtgag cgtggtgaag | 1080 |

-continued

```
aaggcgtacc agaagctgtg ctacatccac cacatcatgg ggaaggtgcc ggacgcgtgc   1140
acggcgtgcg acctggtgaa cgtggacctg gacgactgca tcttcgagca gtaa          1194

<210> SEQ ID NO 5
<211> LENGTH: 1194
<212> TYPE: DNA
<213> ORGANISM: adeno-associated virus 2
<220> FEATURE:
<221> NAME/KEY: CDS
<222> LOCATION: (1)..(1194)
<223> OTHER INFORMATION: Rep52

<400> SEQUENCE: 5 atg gag ctg gtc ggg tgg ctc gtg gac aag ggg att acc tcg gag aag      48
Met Glu Leu Val Gly Trp Leu Val Asp Lys Gly Ile Thr Ser Glu Lys
1               5                   10                  15 cag tgg atc cag gag gac cag gcc tca tac atc tcc ttc aat gcg gcc      96
Gln Trp Ile Gln Glu Asp Gln Ala Ser Tyr Ile Ser Phe Asn Ala Ala
            20                  25                  30 tcc aac tcg cgg tcc caa atc aag gct gcc ttg gac aat gcg gga aag     144
Ser Asn Ser Arg Ser Gln Ile Lys Ala Ala Leu Asp Asn Ala Gly Lys
        35                  40                  45 att atg agc ctg act aaa acc gcc ccc gac tac ctg gtg ggc cag cag     192
Ile Met Ser Leu Thr Lys Thr Ala Pro Asp Tyr Leu Val Gly Gln Gln
    50                  55                  60 ccc gtg gag gac att tcc agc aat cgg att tat aaa att ttg gaa cta     240
Pro Val Glu Asp Ile Ser Ser Asn Arg Ile Tyr Lys Ile Leu Glu Leu
65                  70                  75                  80 aac ggg tac gat ccc caa tat gcg gct tcc gtc ttt ctg gga tgg gcc     288
Asn Gly Tyr Asp Pro Gln Tyr Ala Ala Ser Val Phe Leu Gly Trp Ala
                85                  90                  95 acg aaa aag ttc ggc aag agg aac acc atc tgg ctg ttt ggg cct gca     336
Thr Lys Lys Phe Gly Lys Arg Asn Thr Ile Trp Leu Phe Gly Pro Ala
            100                 105                 110 act acc ggg aag acc aac atc gcg gag gcc ata gcc cac act gtg ccc     384
Thr Thr Gly Lys Thr Asn Ile Ala Glu Ala Ile Ala His Thr Val Pro
        115                 120                 125 ttc tac ggg tgc gta aac tgg acc aat gag aac ttt ccc ttc aac gac     432
Phe Tyr Gly Cys Val Asn Trp Thr Asn Glu Asn Phe Pro Phe Asn Asp
    130                 135                 140 tgt gtc gac aag atg gtg atc tgg tgg gag gag ggg aag atg acc gcc     480
Cys Val Asp Lys Met Val Ile Trp Trp Glu Glu Gly Lys Met Thr Ala
145                 150                 155                 160 aag gtc gtg gag tcg gcc aaa gcc att ctc gga gga agc aag gtg cgc     528
Lys Val Val Glu Ser Ala Lys Ala Ile Leu Gly Gly Ser Lys Val Arg
                165                 170                 175 gtg gac cag aaa tgc aag tcc tcg gcc cag ata gac ccg act ccc gtg     576
Val Asp Gln Lys Cys Lys Ser Ser Ala Gln Ile Asp Pro Thr Pro Val
            180                 185                 190 atc gtc acc tcc aac acc aac atg tgc gcc gtg att gac ggg aac tca     624
Ile Val Thr Ser Asn Thr Asn Met Cys Ala Val Ile Asp Gly Asn Ser
        195                 200                 205 acg acc ttc gaa cac cag cag ccg ttg caa gac cgg atg ttc aaa ttt     672
Thr Thr Phe Glu His Gln Gln Pro Leu Gln Asp Arg Met Phe Lys Phe
    210                 215                 220 gaa ctc acc cgc cgt ctg gat cat gac ttt ggg aag gtc acc aag cag     720
Glu Leu Thr Arg Arg Leu Asp His Asp Phe Gly Lys Val Thr Lys Gln
225                 230                 235                 240 gaa gtc aaa gac ttt ttc cgg tgg gca aag gat cac gtg gtt gag gtg     768
Glu Val Lys Asp Phe Phe Arg Trp Ala Lys Asp His Val Val Glu Val
```

```
                    245                 250                 255
gag cat gaa ttc tac gtc aaa aag ggt gga gcc aag aaa aga ccc gcc        816
Glu His Glu Phe Tyr Val Lys Lys Gly Gly Ala Lys Lys Arg Pro Ala
                    260                 265                 270 ccc agt gac gca gat ata agt gag ccc aaa cgg gtg cgc gag tca gtt        864
Pro Ser Asp Ala Asp Ile Ser Glu Pro Lys Arg Val Arg Glu Ser Val
                275                 280                 285 gcg cag cca tcg acg tca gac gcg gaa gct tcg atc aac tac gca gac        912
Ala Gln Pro Ser Thr Ser Asp Ala Glu Ala Ser Ile Asn Tyr Ala Asp
            290                 295                 300 cgc tac caa aac aaa tgt tct cgt cac gtg ggc atg aat ctg atg ctg        960
Arg Tyr Gln Asn Lys Cys Ser Arg His Val Gly Met Asn Leu Met Leu
305                 310                 315                 320 ttt ccc tgc aga caa tgc gag aga atg aat cag aat tca aat atc tgc       1008
Phe Pro Cys Arg Gln Cys Glu Arg Met Asn Gln Asn Ser Asn Ile Cys
                325                 330                 335 ttc act cac gga cag aaa gac tgt tta gag tgc ttt ccc gtg tca gaa       1056
Phe Thr His Gly Gln Lys Asp Cys Leu Glu Cys Phe Pro Val Ser Glu
                340                 345                 350 tct caa ccc gtt tct gtc gtc aaa aag gcg tat cag aaa ctg tgc tac       1104
Ser Gln Pro Val Ser Val Val Lys Lys Ala Tyr Gln Lys Leu Cys Tyr
                355                 360                 365 att cat cat atc atg gga aag gtg cca gac gct tgc act gcc tgc gat       1152
Ile His His Ile Met Gly Lys Val Pro Asp Ala Cys Thr Ala Cys Asp
        370                 375                 380 ctg gtc aat gtg gat ttg gat gac tgc atc ttt gaa caa taa              1194
Leu Val Asn Val Asp Leu Asp Asp Cys Ile Phe Glu Gln
385                 390                 395

<210> SEQ ID NO 6
<211> LENGTH: 397
<212> TYPE: PRT
<213> ORGANISM: adeno-associated virus 2

<400> SEQUENCE: 6

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175
```

```
Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Ala Tyr Gln Lys Leu Cys Tyr
        355                 360                 365

Ile His His Ile Met Gly Lys Val Pro Asp Ala Cys Thr Ala Cys Asp
    370                 375                 380

Leu Val Asn Val Asp Leu Asp Asp Cys Ile Phe Glu Gln
385                 390                 395

<210> SEQ ID NO 7
<211> LENGTH: 1876
<212> TYPE: DNA
<213> ORGANISM: adeno-associated virus 2
<220> FEATURE:
<221> NAME/KEY: CDS
<222> LOCATION: (11)..(1876)
<223> OTHER INFORMATION: Rep78

<400> SEQUENCE: 7
cgcagccgcc atg ccg ggg ttt tac gag att gtg att aag gtc ccc agc      49
           Met Pro Gly Phe Tyr Glu Ile Val Ile Lys Val Pro Ser
               1               5                   10 gac ctt gac gag cat ctg ccc ggc att tct gac agc ttt gtg aac tgg      97
Asp Leu Asp Glu His Leu Pro Gly Ile Ser Asp Ser Phe Val Asn Trp
 15              20                  25 gtg gcc gag aag gaa tgg gag ttg ccg cca gat tct gac atg gat ctg     145
Val Ala Glu Lys Glu Trp Glu Leu Pro Pro Asp Ser Asp Met Asp Leu
 30              35                  40                  45 aat ctg att gag cag gca ccc ctg acc gtg gcc gag aag ctg cag cgc     193
Asn Leu Ile Glu Gln Ala Pro Leu Thr Val Ala Glu Lys Leu Gln Arg
                 50                  55                  60 gac ttt ctg acg gaa tgg cgc cgt gtg agt aag gcc ccg gag gcc ctt     241
Asp Phe Leu Thr Glu Trp Arg Arg Val Ser Lys Ala Pro Glu Ala Leu
             65                  70                  75 ttc ttt gtg caa ttt gag aag gga gag agc tac ttc cac atg cac gtg     289
Phe Phe Val Gln Phe Glu Lys Gly Glu Ser Tyr Phe His Met His Val
         80                  85                  90 ctc gtg gaa acc acc ggg gtg aaa tcc atg gtt ttg gga cgt ttc ctg     337
```

```
                                Leu Val Glu Thr Thr Gly Val Lys Ser Met Val Leu Gly Arg Phe Leu
                                     95                 100                 105 agt cag att cgc gaa aaa ctg att cag aga att tac cgc ggg atc gag                385
Ser Gln Ile Arg Glu Lys Leu Ile Gln Arg Ile Tyr Arg Gly Ile Glu
110                 115                 120                 125 ccg act ttg cca aac tgg ttc gcg gtc aca aag acc aga aat ggc gcc                433
Pro Thr Leu Pro Asn Trp Phe Ala Val Thr Lys Thr Arg Asn Gly Ala
                    130                 135                 140 gga ggc ggg aac aag gtg gtg gat gag tgc tac atc ccc aat tac ttg                481
Gly Gly Gly Asn Lys Val Val Asp Glu Cys Tyr Ile Pro Asn Tyr Leu
                145                 150                 155 ctc ccc aaa acc cag cct gag ctc cag tgg gcg tgg act aat atg gaa                529
Leu Pro Lys Thr Gln Pro Glu Leu Gln Trp Ala Trp Thr Asn Met Glu
        160                 165                 170 cag tat tta agc gcc tgt ttg aat ctc acg gag cgt aaa cgg ttg gtg                577
Gln Tyr Leu Ser Ala Cys Leu Asn Leu Thr Glu Arg Lys Arg Leu Val
        175                 180                 185 gcg cag cat ctg acg cac gtg tcg cag acg cag gag cag aac aaa gag                625
Ala Gln His Leu Thr His Val Ser Gln Thr Gln Glu Gln Asn Lys Glu
190                 195                 200                 205 aat cag aat ccc aat tct gat gcg ccg gtg atc aga tca aaa act tca                673
Asn Gln Asn Pro Asn Ser Asp Ala Pro Val Ile Arg Ser Lys Thr Ser
                    210                 215                 220 gcc agg tac atg gag ctg gtc ggg tgg ctc gtg gac aag ggg att acc                721
Ala Arg Tyr Met Glu Leu Val Gly Trp Leu Val Asp Lys Gly Ile Thr
                225                 230                 235 tcg gag aag cag tgg atc cag gag gac cag gcc tca tac atc tcc ttc                769
Ser Glu Lys Gln Trp Ile Gln Glu Asp Gln Ala Ser Tyr Ile Ser Phe
        240                 245                 250 aat gcg gcc tcc aac tcg cgg tcc caa atc aag gct gcc ttg gac aat                817
Asn Ala Ala Ser Asn Ser Arg Ser Gln Ile Lys Ala Ala Leu Asp Asn
        255                 260                 265 gcg gga aag att atg agc ctg act aaa acc gcc ccc gac tac ctg gtg                865
Ala Gly Lys Ile Met Ser Leu Thr Lys Thr Ala Pro Asp Tyr Leu Val
270                 275                 280                 285 ggc cag cag ccc gtg gag gac att tcc agc aat cgg att tat aaa att                913
Gly Gln Gln Pro Val Glu Asp Ile Ser Ser Asn Arg Ile Tyr Lys Ile
                    290                 295                 300 ttg gaa cta aac ggg tac gat ccc caa tat gcg gct tcc gtc ttt ctg                961
Leu Glu Leu Asn Gly Tyr Asp Pro Gln Tyr Ala Ala Ser Val Phe Leu
                305                 310                 315 gga tgg gcc acg aaa aag ttc ggc aag agg aac acc atc tgg ctg ttt               1009
Gly Trp Ala Thr Lys Lys Phe Gly Lys Arg Asn Thr Ile Trp Leu Phe
        320                 325                 330 ggg cct gca act acc ggg aag acc aac atc gcg gag gcc ata gcc cac               1057
Gly Pro Ala Thr Thr Gly Lys Thr Asn Ile Ala Glu Ala Ile Ala His
        335                 340                 345 act gtg ccc ttc tac ggg tgc gta aac tgg acc aat gag aac ttt ccc               1105
Thr Val Pro Phe Tyr Gly Cys Val Asn Trp Thr Asn Glu Asn Phe Pro
350                 355                 360                 365 ttc aac gac tgt gtc gac aag atg gtg atc tgg tgg gag gag ggg aag               1153
Phe Asn Asp Cys Val Asp Lys Met Val Ile Trp Trp Glu Glu Gly Lys
                    370                 375                 380 atg acc gcc aag gtc gtg gag tcg gcc aaa gcc att ctc gga gga agc               1201
Met Thr Ala Lys Val Val Glu Ser Ala Lys Ala Ile Leu Gly Gly Ser
                385                 390                 395 aag gtg cgc gtg gac cag aaa tgc aag tcc tcg gcc cag ata gac ccg               1249
Lys Val Arg Val Asp Gln Lys Cys Lys Ser Ser Ala Gln Ile Asp Pro
        400                 405                 410
```

```
act ccc gtg atc gtc acc tcc aac acc aac atg tgc gcc gtg att gac      1297
Thr Pro Val Ile Val Thr Ser Asn Thr Asn Met Cys Ala Val Ile Asp
    415                 420                 425 ggg aac tca acg acc ttc gaa cac cag cag ccg ttg caa gac cgg atg      1345
Gly Asn Ser Thr Thr Phe Glu His Gln Gln Pro Leu Gln Asp Arg Met
430                 435                 440                 445 ttc aaa ttt gaa ctc acc cgc cgt ctg gat cat gac ttt ggg aag gtc      1393
Phe Lys Phe Glu Leu Thr Arg Arg Leu Asp His Asp Phe Gly Lys Val
                450                 455                 460 acc aag cag gaa gtc aaa gac ttt ttc cgg tgg gca aag gat cac gtg      1441
Thr Lys Gln Glu Val Lys Asp Phe Phe Arg Trp Ala Lys Asp His Val
            465                 470                 475 gtt gag gtg gag cat gaa ttc tac gtc aaa aag ggt gga gcc aag aaa      1489
Val Glu Val Glu His Glu Phe Tyr Val Lys Lys Gly Gly Ala Lys Lys
        480                 485                 490 aga ccc gcc ccc agt gac gca gat ata agt gag ccc aaa cgg gtg cgc      1537
Arg Pro Ala Pro Ser Asp Ala Asp Ile Ser Glu Pro Lys Arg Val Arg
    495                 500                 505 gag tca gtt gcg cag cca tcg acg tca gac gcg gaa gct tcg atc aac      1585
Glu Ser Val Ala Gln Pro Ser Thr Ser Asp Ala Glu Ala Ser Ile Asn
510                 515                 520                 525 tac gca gac agg tac caa aac aaa tgt tct cgt cac gtg ggc atg aat      1633
Tyr Ala Asp Arg Tyr Gln Asn Lys Cys Ser Arg His Val Gly Met Asn
                530                 535                 540 ctg atg ctg ttt ccc tgc aga caa tgc gag aga atg aat cag aat tca      1681
Leu Met Leu Phe Pro Cys Arg Gln Cys Glu Arg Met Asn Gln Asn Ser
            545                 550                 555 aat atc tgc ttc act cac gga cag aaa gac tgt tta gag tgc ttt ccc      1729
Asn Ile Cys Phe Thr His Gly Gln Lys Asp Cys Leu Glu Cys Phe Pro
        560                 565                 570 gtg tca gaa tct caa ccc gtt tct gtc gtc aaa aag gcg tat cag aaa      1777
Val Ser Glu Ser Gln Pro Val Ser Val Val Lys Lys Ala Tyr Gln Lys
    575                 580                 585 ctg tgc tac att cat cat atc atg gga aag gtg cca gac gct tgc act      1825
Leu Cys Tyr Ile His His Ile Met Gly Lys Val Pro Asp Ala Cys Thr
590                 595                 600                 605 gcc tgc gat ctg gtc aat gtg gat ttg gat gac tgc atc ttt gaa caa      1873
Ala Cys Asp Leu Val Asn Val Asp Leu Asp Asp Cys Ile Phe Glu Gln
                610                 615                 620 taa                                                                  1876

<210> SEQ ID NO 8
<211> LENGTH: 621
<212> TYPE: PRT
<213> ORGANISM: adeno-associated virus 2

<400> SEQUENCE: 8

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95
```

-continued

```
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
```

```
Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620

<210> SEQ ID NO 9
<211> LENGTH: 9
<212> TYPE: DNA
<213> ORGANISM: adeno-associated virus 2
<220> FEATURE:
<221> NAME/KEY: misc_feature
<222> LOCATION: (1)..(9)
<223> OTHER INFORMATION: 7 nt initiation

<400> SEQUENCE: 9 cctgttaag                                                                  9

<210> SEQ ID NO 10
<211> LENGTH: 28
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(28)
<223> OTHER INFORMATION: HR1-FW

<400> SEQUENCE: 10
gtatacgtat gacactatcg atgttgac                                            28

<210> SEQ ID NO 11
<211> LENGTH: 30
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (1)..(30)
<223> OTHER INFORMATION: HR1-RV

<400> SEQUENCE: 11
gtatacgatc gattattgct ccaatactag                                          30

<210> SEQ ID NO 12
<211> LENGTH: 25
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(25)
<223> OTHER INFORMATION: polyA FW
```

<400> SEQUENCE: 12
agatctgtag tggctatggc agggc                                          25

<210> SEQ ID NO 13
<211> LENGTH: 35
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(35)
<223> OTHER INFORMATION: p10 RV

<400> SEQUENCE: 13
agatctcccg ggacggacct ttaattcaac ccaac                               35

<210> SEQ ID NO 14
<211> LENGTH: 33
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(33)
<223> OTHER INFORMATION: BstZ17I-deltaIE1 FW

<400> SEQUENCE: 14
ggtccgtata cgacgataac gccgttggtg gcg                                 33

<210> SEQ ID NO 15
<211> LENGTH: 30
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (1)..(30)
<223> OTHER INFORMATION: AflII-delta IE1 RV

<400> SEQUENCE: 15
cgacttaaga cggcgaattc tgcagatggc                                     30

<210> SEQ ID NO 16
<211> LENGTH: 37
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(37)
<223> OTHER INFORMATION: SmaI-pPolh FW

<400> SEQUENCE: 16
tctcccggga gatcatggag ataattaaaa tgataac                             37

<210> SEQ ID NO 17
<211> LENGTH: 21
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (1)..(21)
<223> OTHER INFORMATION: SpeI-pPolh RV -continued

```
<400> SEQUENCE: 17
gttactagtg agctcgtcga c                                              21

<210> SEQ ID NO 18
<211> LENGTH: 23
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (1)..(23)
<223> OTHER INFORMATION: BstZ17I-p10 FW

<400> SEQUENCE: 18
agtatacgga cctttaattc aac                                            23

<210> SEQ ID NO 19
<211> LENGTH: 28
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (1)..(28)
<223> OTHER INFORMATION: AflII-p10 RV

<400> SEQUENCE: 19
cgacttaaga gcgggccgct ttcgaatc                                       28

<210> SEQ ID NO 20
<211> LENGTH: 2211
<212> TYPE: DNA
<213> ORGANISM: Artificial sequence
<220> FEATURE:
<223> OTHER INFORMATION: adeno-associated virus 1; VP1, VP2, VP3;
      startcodon VP1 altered (GTG)
<220> FEATURE:
<221> NAME/KEY: CDS
<222> LOCATION: (1)..(2208)
<223> OTHER INFORMATION: VP1
<220> FEATURE:
<221> NAME/KEY: misc_feature
<222> LOCATION: (412)..(2208)
<223> OTHER INFORMATION: VP2
<220> FEATURE:
<221> NAME/KEY: misc_feature
<222> LOCATION: (607)..(2208)
<223> OTHER INFORMATION: VP3

<400> SEQUENCE: 20 gtg gct gcc gac ggt tat cta ccc gat tgg ctc gag gac aac ctc tct      48
Val Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aag ccc      96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac     240
Val Asn Ala Ala Asp Ala Ala Ala Leu Glu His Asp Lys Ala Tyr Asp
65                  70                  75                  80
```

-continued

```
cag cag ctc aaa gcg ggt gac aat ccg tac ctg cgg tat aac cac gcc    288
Gln Gln Leu Lys Ala Gly Asp Asn Pro Tyr Leu Arg Tyr Asn His Ala
            85                  90                  95 gac gcc gag ttt cag gag cgt ctg caa gaa gat acg tct ttt ggg ggc    336
Asp Ala Glu Phe Gln Glu Arg Leu Gln Glu Asp Thr Ser Phe Gly Gly
100                 105                 110 aac ctc ggg cga gca gtc ttc cag gcc aag aag cgg gtt ctc gaa cct    384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aaa cgt    432
Leu Gly Leu Val Glu Glu Gly Ala Lys Thr Ala Pro Gly Lys Lys Arg
    130                 135                 140 ccg gta gag cag tcg cca caa gag cca gac tcc tcc tcg ggc atc ggc    480
Pro Val Glu Gln Ser Pro Gln Glu Pro Asp Ser Ser Ser Gly Ile Gly
145                 150                 155                 160 aag aca ggc cag cag ccc gct aaa aag aga ctc aat ttt ggt cag act    528
Lys Thr Gly Gln Gln Pro Ala Lys Lys Arg Leu Asn Phe Gly Gln Thr
                165                 170                 175 ggc gac tca gag tca gtc ccc gat cca caa cct ctc gga gaa cct cca    576
Gly Asp Ser Glu Ser Val Pro Asp Pro Gln Pro Leu Gly Glu Pro Pro
            180                 185                 190 gca acc ccc gct gct gtg gga cct act aca atg gct tca ggc ggt ggc    624
Ala Thr Pro Ala Ala Val Gly Pro Thr Thr Met Ala Ser Gly Gly Gly
        195                 200                 205 gca cca atg gca gac aat aac gaa ggc gcc gac gga gtg ggt aat gcc    672
Ala Pro Met Ala Asp Asn Asn Glu Gly Ala Asp Gly Val Gly Asn Ala
    210                 215                 220 tca gga aat tgg cat tgc gat tcc aca tgg ctg ggc gac aga gtc atc    720
Ser Gly Asn Trp His Cys Asp Ser Thr Trp Leu Gly Asp Arg Val Ile
225                 230                 235                 240 acc acc agc acc cgc acc tgg gcc ttg ccc acc tac aat aac cac ctc    768
Thr Thr Ser Thr Arg Thr Trp Ala Leu Pro Thr Tyr Asn Asn His Leu
                245                 250                 255 tac aag caa atc tcc agt gct tca acg ggg gcc agc aac gac aac cac    816
Tyr Lys Gln Ile Ser Ser Ala Ser Thr Gly Ala Ser Asn Asp Asn His
            260                 265                 270 tac ttc ggc tac agc acc ccc tgg ggg tat ttt gat ttc aac aga ttc    864
Tyr Phe Gly Tyr Ser Thr Pro Trp Gly Tyr Phe Asp Phe Asn Arg Phe
        275                 280                 285 cac tgc cac ttt tca cca cgt gac tgg cag cga ctc atc aac aac aat    912
His Cys His Phe Ser Pro Arg Asp Trp Gln Arg Leu Ile Asn Asn Asn
    290                 295                 300 tgg gga ttc cgg ccc aag aga ctc aac ttc aaa ctc ttc aac atc caa    960
Trp Gly Phe Arg Pro Lys Arg Leu Asn Phe Lys Leu Phe Asn Ile Gln
305                 310                 315                 320 gtc aag gag gtc acg acg aat gat ggc gtc aca acc atc gct aat aac   1008
Val Lys Glu Val Thr Thr Asn Asp Gly Val Thr Thr Ile Ala Asn Asn
                325                 330                 335 ctt acc agc acg gtt caa gtc ttc tcg gac tcg gag tac cag ctt ccg   1056
Leu Thr Ser Thr Val Gln Val Phe Ser Asp Ser Glu Tyr Gln Leu Pro
            340                 345                 350 tac gtc ctc ggc tct gcg cac cag ggc tgc ctc cct ccg ttc ccg gcg   1104
Tyr Val Leu Gly Ser Ala His Gln Gly Cys Leu Pro Pro Phe Pro Ala
        355                 360                 365 gac gtg ttc atg att ccg caa tac ggc tac ctg acg ctc aac aat ggc   1152
Asp Val Phe Met Ile Pro Gln Tyr Gly Tyr Leu Thr Leu Asn Asn Gly
    370                 375                 380 agc caa gcc gtg gga cgt tca tcc ttt tac tgc ctg gaa tat ttc cct   1200
Ser Gln Ala Val Gly Arg Ser Ser Phe Tyr Cys Leu Glu Tyr Phe Pro
```

```
                    385                 390                 395                 400
tct cag atg ctg aga acg ggc aac aac ttt acc ttc agc tac acc ttt    1248
Ser Gln Met Leu Arg Thr Gly Asn Asn Phe Thr Phe Ser Tyr Thr Phe
                405                 410                 415 gag gaa gtg cct ttc cac agc agc tac gcg cac agc cag agc ctg gac    1296
Glu Glu Val Pro Phe His Ser Ser Tyr Ala His Ser Gln Ser Leu Asp
                420                 425                 430 cgg ctg atg aat cct ctc atc gac caa tac ctg tat tac ctg aac aga    1344
Arg Leu Met Asn Pro Leu Ile Asp Gln Tyr Leu Tyr Tyr Leu Asn Arg
                435                 440                 445 act caa aat cag tcc gga agt gcc caa aac aag gac ttg ctg ttt agc    1392
Thr Gln Asn Gln Ser Gly Ser Ala Gln Asn Lys Asp Leu Leu Phe Ser
                450                 455                 460 cgt ggg tct cca gct ggc atg tct gtt cag ccc aaa aac tgg cta cct    1440
Arg Gly Ser Pro Ala Gly Met Ser Val Gln Pro Lys Asn Trp Leu Pro
465                 470                 475                 480 gga ccc tgt tat cgg cag cag cgc gtt tct aaa aca aaa aca gac aac    1488
Gly Pro Cys Tyr Arg Gln Gln Arg Val Ser Lys Thr Lys Thr Asp Asn
                485                 490                 495 aac aac agc aat ttt acc tgg act ggt gct tca aaa tat aac ctc aat    1536
Asn Asn Ser Asn Phe Thr Trp Thr Gly Ala Ser Lys Tyr Asn Leu Asn
                500                 505                 510 ggg cgt gaa tcc atc atc aac cct ggc act gct atg gcc tca cac aaa    1584
Gly Arg Glu Ser Ile Ile Asn Pro Gly Thr Ala Met Ala Ser His Lys
                515                 520                 525 gac gac gaa gac aag ttc ttt ccc atg agc ggt gtc atg att ttt gga    1632
Asp Asp Glu Asp Lys Phe Phe Pro Met Ser Gly Val Met Ile Phe Gly
                530                 535                 540 aaa gag agc gcc gga gct tca aac act gca ttg gac aat gtc atg att    1680
Lys Glu Ser Ala Gly Ala Ser Asn Thr Ala Leu Asp Asn Val Met Ile
545                 550                 555                 560 aca gac gaa gag gaa att aaa gcc act aac cct gtg gcc acc gaa aga    1728
Thr Asp Glu Glu Glu Ile Lys Ala Thr Asn Pro Val Ala Thr Glu Arg
                565                 570                 575 ttt ggg acc gtg gca gtc aat ttc cag agc agc agc aca gac cct gcg    1776
Phe Gly Thr Val Ala Val Asn Phe Gln Ser Ser Ser Thr Asp Pro Ala
                580                 585                 590 acc gga gat gtg cat gct atg gga gca tta cct ggc atg gtg tgg caa    1824
Thr Gly Asp Val His Ala Met Gly Ala Leu Pro Gly Met Val Trp Gln
                595                 600                 605 gat aga gac gtg tac ctg cag ggt ccc att tgg gcc aaa att cct cac    1872
Asp Arg Asp Val Tyr Leu Gln Gly Pro Ile Trp Ala Lys Ile Pro His
                610                 615                 620 aca gat gga cac ttt cac ccg tct cct ctt atg ggc ggc ttt gga ctc    1920
Thr Asp Gly His Phe His Pro Ser Pro Leu Met Gly Gly Phe Gly Leu
625                 630                 635                 640 aag aac ccg cct cct cag atc ctc atc aaa aac acg cct gtt cct gcg    1968
Lys Asn Pro Pro Pro Gln Ile Leu Ile Lys Asn Thr Pro Val Pro Ala
                645                 650                 655 aat cct ccg gcg gag ttt tca gct aca aag ttt gct tca ttc atc acc    2016
Asn Pro Pro Ala Glu Phe Ser Ala Thr Lys Phe Ala Ser Phe Ile Thr
                660                 665                 670 caa tac tcc aca gga caa gtg agt gtg gaa att gaa tgg gag ctg cag    2064
Gln Tyr Ser Thr Gly Gln Val Ser Val Glu Ile Glu Trp Glu Leu Gln
                675                 680                 685 aaa gaa aac agc aag cgc tgg aat ccc gaa gtg cag tac aca tcc aat    2112
Lys Glu Asn Ser Lys Arg Trp Asn Pro Glu Val Gln Tyr Thr Ser Asn
                690                 695                 700 tat gca aaa tct gcc aac gtt gat ttt act gtg gac aac aat gga ctt    2160
```

```
Tyr Ala Lys Ser Ala Asn Val Asp Phe Thr Val Asp Asn Asn Gly Leu
705                 710                 715                 720 tat act gag cct cgc ccc att ggc acc cgt tac ctt acc cgt ccc ctg    2208
Tyr Thr Glu Pro Arg Pro Ile Gly Thr Arg Tyr Leu Thr Arg Pro Leu
                725                 730                 735 taa                                                                2211
```

<210> SEQ ID NO 21
<211> LENGTH: 736
<212> TYPE: PRT
<213> ORGANISM: Artificial sequence
<220> FEATURE:
<223> OTHER INFORMATION: Synthetic Construct

<400> SEQUENCE: 21

```
Val Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320
```

```
Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
        405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
    515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

```
<210> SEQ ID NO 22
<211> LENGTH: 1800
<212> TYPE: DNA
<213> ORGANISM: Artificial sequence
<220> FEATURE:
<223> OTHER INFORMATION: adeno-associated virus 1; VP2, VP3
<220> FEATURE:
<221> NAME/KEY: CDS
<222> LOCATION: (1)..(1797)
<223> OTHER INFORMATION: VP2

<400> SEQUENCE: 22 acg gct cct gga aag aaa cgt ccg gta gag cag tcg cca caa gag cca      48
Thr Ala Pro Gly Lys Lys Arg Pro Val Glu Gln Ser Pro Gln Glu Pro
1               5                   10                  15 gac tcc tcc tcg ggc atc ggc aag aca ggc cag cag ccc gct aaa aag      96
Asp Ser Ser Ser Gly Ile Gly Lys Thr Gly Gln Gln Pro Ala Lys Lys
            20                  25                  30 aga ctc aat ttt ggt cag act ggc gac tca gag tca gtc ccc gat cca     144
Arg Leu Asn Phe Gly Gln Thr Gly Asp Ser Glu Ser Val Pro Asp Pro
        35                  40                  45 caa cct ctc gga gaa cct cca gca acc ccc gct gct gtg gga cct act     192
Gln Pro Leu Gly Glu Pro Pro Ala Thr Pro Ala Ala Val Gly Pro Thr
    50                  55                  60 aca atg gct tca ggc ggt ggc gca cca atg gca gac aat aac gaa ggc     240
Thr Met Ala Ser Gly Gly Gly Ala Pro Met Ala Asp Asn Asn Glu Gly
65                  70                  75                  80 gcc gac gga gtg ggt aat gcc tca gga aat tgg cat tgc gat tcc aca     288
Ala Asp Gly Val Gly Asn Ala Ser Gly Asn Trp His Cys Asp Ser Thr
                85                  90                  95 tgg ctg ggc gac aga gtc atc acc acc agc acc cgc acc tgg gcc ttg     336
Trp Leu Gly Asp Arg Val Ile Thr Thr Ser Thr Arg Thr Trp Ala Leu
            100                 105                 110 ccc acc tac aat aac cac ctc tac aag caa atc tcc agt gct tca acg     384
Pro Thr Tyr Asn Asn His Leu Tyr Lys Gln Ile Ser Ser Ala Ser Thr
        115                 120                 125 ggg gcc agc aac gac aac cac tac ttc ggc tac agc acc ccc tgg ggg     432
Gly Ala Ser Asn Asp Asn His Tyr Phe Gly Tyr Ser Thr Pro Trp Gly
    130                 135                 140 tat ttt gat ttc aac aga ttc cac tgc cac ttt tca cca cgt gac tgg     480
Tyr Phe Asp Phe Asn Arg Phe His Cys His Phe Ser Pro Arg Asp Trp
145                 150                 155                 160 cag cga ctc atc aac aac aat tgg gga ttc cgg ccc aag aga ctc aac     528
Gln Arg Leu Ile Asn Asn Asn Trp Gly Phe Arg Pro Lys Arg Leu Asn
                165                 170                 175 ttc aaa ctc ttc aac atc caa gtc aag gag gtc acg acg aat gat ggc     576
Phe Lys Leu Phe Asn Ile Gln Val Lys Glu Val Thr Thr Asn Asp Gly
            180                 185                 190 gtc aca acc atc gct aat aac ctt acc agc acg gtt caa gtc ttc tcg     624
Val Thr Thr Ile Ala Asn Asn Leu Thr Ser Thr Val Gln Val Phe Ser
        195                 200                 205 gac tcg gag tac cag ctt ccg tac gtc ctc ggc tct gcg cac cag ggc     672
Asp Ser Glu Tyr Gln Leu Pro Tyr Val Leu Gly Ser Ala His Gln Gly
    210                 215                 220 tgc ctc cct ccg ttc ccg gcg gac gtg ttc atg att ccg caa tac ggc     720
Cys Leu Pro Pro Phe Pro Ala Asp Val Phe Met Ile Pro Gln Tyr Gly
225                 230                 235                 240 tac ctg acg ctc aac aat ggc agc caa gcc gtg gga cgt tca tcc ttt     768
Tyr Leu Thr Leu Asn Asn Gly Ser Gln Ala Val Gly Arg Ser Ser Phe
                245                 250                 255 tac tgc ctg gaa tat ttc cct tct cag atg ctg aga acg ggc aac aac     816
Tyr Cys Leu Glu Tyr Phe Pro Ser Gln Met Leu Arg Thr Gly Asn Asn
```

```
                    260                 265                 270
ttt acc ttc agc tac acc ttt gag gaa gtg cct ttc cac agc agc tac    864
Phe Thr Phe Ser Tyr Thr Phe Glu Glu Val Pro Phe His Ser Ser Tyr
        275                 280                 285 gcg cac agc cag agc ctg gac cgg ctg atg aat cct ctc atc gac caa    912
Ala His Ser Gln Ser Leu Asp Arg Leu Met Asn Pro Leu Ile Asp Gln
    290                 295                 300 tac ctg tat tac ctg aac aga act caa aat cag tcc gga agt gcc caa    960
Tyr Leu Tyr Tyr Leu Asn Arg Thr Gln Asn Gln Ser Gly Ser Ala Gln
305                 310                 315                 320 aac aag gac ttg ctg ttt agc cgt ggg tct cca gct ggc atg tct gtt   1008
Asn Lys Asp Leu Leu Phe Ser Arg Gly Ser Pro Ala Gly Met Ser Val
                325                 330                 335 cag ccc aaa aac tgg cta cct gga ccc tgt tat cgg cag cag cgc gtt   1056
Gln Pro Lys Asn Trp Leu Pro Gly Pro Cys Tyr Arg Gln Gln Arg Val
            340                 345                 350 tct aaa aca aaa aca gac aac aac aac agc aat ttt acc tgg act ggt   1104
Ser Lys Thr Lys Thr Asp Asn Asn Asn Ser Asn Phe Thr Trp Thr Gly
        355                 360                 365 gct tca aaa tat aac ctc aat ggg cgt gaa tcc atc atc aac cct ggc   1152
Ala Ser Lys Tyr Asn Leu Asn Gly Arg Glu Ser Ile Ile Asn Pro Gly
    370                 375                 380 act gct atg gcc tca cac aaa gac gac gaa gac aag ttc ttt ccc atg   1200
Thr Ala Met Ala Ser His Lys Asp Asp Glu Asp Lys Phe Phe Pro Met
385                 390                 395                 400 agc ggt gtc atg att ttt gga aaa gag agc gcc gga gct tca aac act   1248
Ser Gly Val Met Ile Phe Gly Lys Glu Ser Ala Gly Ala Ser Asn Thr
                405                 410                 415 gca ttg gac aat gtc atg att aca gac gaa gag gaa att aaa gcc act   1296
Ala Leu Asp Asn Val Met Ile Thr Asp Glu Glu Glu Ile Lys Ala Thr
            420                 425                 430 aac cct gtg gcc acc gaa aga ttt ggg acc gtg gca gtc aat ttc cag   1344
Asn Pro Val Ala Thr Glu Arg Phe Gly Thr Val Ala Val Asn Phe Gln
        435                 440                 445 agc agc agc aca gac cct gcg acc gga gat gtg cat gct atg gga gca   1392
Ser Ser Ser Thr Asp Pro Ala Thr Gly Asp Val His Ala Met Gly Ala
    450                 455                 460 tta cct ggc atg gtg tgg caa gat aga gac gtg tac ctg cag ggt ccc   1440
Leu Pro Gly Met Val Trp Gln Asp Arg Asp Val Tyr Leu Gln Gly Pro
465                 470                 475                 480 att tgg gcc aaa att cct cac aca gat gga cac ttt cac ccg tct cct   1488
Ile Trp Ala Lys Ile Pro His Thr Asp Gly His Phe His Pro Ser Pro
                485                 490                 495 ctt atg ggc ggc ttt gga ctc aag aac ccg cct cct cag atc ctc atc   1536
Leu Met Gly Gly Phe Gly Leu Lys Asn Pro Pro Pro Gln Ile Leu Ile
            500                 505                 510 aaa aac acg cct gtt cct gcg aat cct ccg gcg gag ttt tca gct aca   1584
Lys Asn Thr Pro Val Pro Ala Asn Pro Pro Ala Glu Phe Ser Ala Thr
        515                 520                 525 aag ttt gct tca ttc atc acc caa tac tcc aca gga caa gtg agt gtg   1632
Lys Phe Ala Ser Phe Ile Thr Gln Tyr Ser Thr Gly Gln Val Ser Val
    530                 535                 540 gaa att gaa tgg gag ctg cag aaa gaa aac agc aag cgc tgg aat ccc   1680
Glu Ile Glu Trp Glu Leu Gln Lys Glu Asn Ser Lys Arg Trp Asn Pro
545                 550                 555                 560 gaa gtg cag tac aca tcc aat tat gca aaa tct gcc aac gtt gat ttt   1728
Glu Val Gln Tyr Thr Ser Asn Tyr Ala Lys Ser Ala Asn Val Asp Phe
                565                 570                 575 act gtg gac aac aat gga ctt tat act gag cct cgc ccc att ggc acc   1776
```

```
                Thr Val Asp Asn Asn Gly Leu Tyr Thr Glu Pro Arg Pro Ile Gly Thr
                            580                 585                 590 cgt tac ctt acc cgt ccc ctg taa                                                        1800
Arg Tyr Leu Thr Arg Pro Leu
            595

<210> SEQ ID NO 23
<211> LENGTH: 599
<212> TYPE: PRT
<213> ORGANISM: Artificial sequence
<220> FEATURE:
<223> OTHER INFORMATION: Synthetic Construct

<400> SEQUENCE: 23

Thr Ala Pro Gly Lys Lys Arg Pro Val Glu Gln Ser Pro Gln Glu Pro
1               5                   10                  15

Asp Ser Ser Ser Gly Ile Gly Lys Thr Gly Gln Gln Pro Ala Lys Lys
            20                  25                  30

Arg Leu Asn Phe Gly Gln Thr Gly Asp Ser Glu Ser Val Pro Asp Pro
        35                  40                  45

Gln Pro Leu Gly Glu Pro Pro Ala Thr Pro Ala Ala Val Gly Pro Thr
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Thr Asn Asp Gly
            180                 185                 190

Val Thr Thr Ile Ala Asn Asn Leu Thr Ser Thr Val Gln Val Phe Ser
        195                 200                 205

Asp Ser Glu Tyr Gln Leu Pro Tyr Val Leu Gly Ser Ala His Gln Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asn Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270

Phe Thr Phe Ser Tyr Thr Phe Glu Glu Val Pro Phe His Ser Ser Tyr
        275                 280                 285

Ala His Ser Gln Ser Leu Asp Arg Leu Met Asn Pro Leu Ile Asp Gln
    290                 295                 300

Tyr Leu Tyr Tyr Leu Asn Arg Thr Gln Asn Gln Ser Gly Ser Ala Gln
305                 310                 315                 320

Asn Lys Asp Leu Leu Phe Ser Arg Gly Ser Pro Ala Gly Met Ser Val
                325                 330                 335
```

```
Gln Pro Lys Asn Trp Leu Pro Gly Pro Cys Tyr Arg Gln Gln Arg Val
                 340                 345                 350
Ser Lys Thr Lys Thr Asp Asn Asn Ser Asn Phe Thr Trp Thr Gly
        355                 360                 365
Ala Ser Lys Tyr Asn Leu Asn Gly Arg Glu Ser Ile Ile Asn Pro Gly
    370                 375                 380
Thr Ala Met Ala Ser His Lys Asp Asp Glu Asp Lys Phe Phe Pro Met
385                 390                 395                 400
Ser Gly Val Met Ile Phe Gly Lys Glu Ser Ala Gly Ala Ser Asn Thr
                405                 410                 415
Ala Leu Asp Asn Val Met Ile Thr Asp Glu Glu Glu Ile Lys Ala Thr
            420                 425                 430
Asn Pro Val Ala Thr Glu Arg Phe Gly Thr Val Ala Val Asn Phe Gln
        435                 440                 445
Ser Ser Ser Thr Asp Pro Ala Thr Gly Asp Val His Ala Met Gly Ala
    450                 455                 460
Leu Pro Gly Met Val Trp Gln Asp Arg Asp Val Tyr Leu Gln Gly Pro
465                 470                 475                 480
Ile Trp Ala Lys Ile Pro His Thr Asp Gly His Phe His Pro Ser Pro
                485                 490                 495
Leu Met Gly Gly Phe Gly Leu Lys Asn Pro Pro Pro Gln Ile Leu Ile
            500                 505                 510
Lys Asn Thr Pro Val Pro Ala Asn Pro Pro Ala Glu Phe Ser Ala Thr
        515                 520                 525
Lys Phe Ala Ser Phe Ile Thr Gln Tyr Ser Thr Gly Gln Val Ser Val
    530                 535                 540
Glu Ile Glu Trp Glu Leu Gln Lys Glu Asn Ser Lys Arg Trp Asn Pro
545                 550                 555                 560
Glu Val Gln Tyr Thr Ser Asn Tyr Ala Lys Ser Ala Asn Val Asp Phe
                565                 570                 575
Thr Val Asp Asn Asn Gly Leu Tyr Thr Glu Pro Arg Pro Ile Gly Thr
            580                 585                 590
Arg Tyr Leu Thr Arg Pro Leu
        595

<210> SEQ ID NO 24
<211> LENGTH: 1605
<212> TYPE: DNA
<213> ORGANISM: Artificial sequence
<220> FEATURE:
<223> OTHER INFORMATION: adeno-associated virus 1; VP3
<220> FEATURE:
<221> NAME/KEY: CDS
<222> LOCATION: (1)..(1602)
<223> OTHER INFORMATION: VP3

<400> SEQUENCE: 24 atg gct tca ggc ggt ggc gca cca atg gca gac aat aac gaa ggc gcc    48
Met Ala Ser Gly Gly Gly Ala Pro Met Ala Asp Asn Asn Glu Gly Ala
1               5                   10                  15 gac gga gtg ggt aat gcc tca gga aat tgg cat tgc gat tcc aca tgg    96
Asp Gly Val Gly Asn Ala Ser Gly Asn Trp His Cys Asp Ser Thr Trp
            20                  25                  30 ctg ggc gac aga gtc atc acc acc agc acc cgc acc tgg gcc ttg ccc    144
Leu Gly Asp Arg Val Ile Thr Thr Ser Thr Arg Thr Trp Ala Leu Pro
        35                  40                  45 acc tac aat aac cac ctc tac aag caa atc tcc agt gct tca acg ggg    192
```

```
                Thr Tyr Asn Asn His Leu Tyr Lys Gln Ile Ser Ser Ala Ser Thr Gly
                    50                  55                  60 gcc agc aac gac aac cac tac ttc ggc tac agc acc ccc tgg ggg tat       240
Ala Ser Asn Asp Asn His Tyr Phe Gly Tyr Ser Thr Pro Trp Gly Tyr
65                  70                  75                  80 ttt gat ttc aac aga ttc cac tgc cac ttt tca cca cgt gac tgg cag       288
Phe Asp Phe Asn Arg Phe His Cys His Phe Ser Pro Arg Asp Trp Gln
                85                  90                  95 cga ctc atc aac aac aat tgg gga ttc cgg ccc aag aga ctc aac ttc       336
Arg Leu Ile Asn Asn Asn Trp Gly Phe Arg Pro Lys Arg Leu Asn Phe
            100                 105                 110 aaa ctc ttc aac atc caa gtc aag gag gtc acg acg aat gat ggc gtc       384
Lys Leu Phe Asn Ile Gln Val Lys Glu Val Thr Thr Asn Asp Gly Val
        115                 120                 125 aca acc atc gct aat aac ctt acc agc acg gtt caa gtc ttc tcg gac       432
Thr Thr Ile Ala Asn Asn Leu Thr Ser Thr Val Gln Val Phe Ser Asp
    130                 135                 140 tcg gag tac cag ctt ccg tac gtc ctc ggc tct gcg cac cag ggc tgc       480
Ser Glu Tyr Gln Leu Pro Tyr Val Leu Gly Ser Ala His Gln Gly Cys
145                 150                 155                 160 ctc cct ccg ttc ccg gcg gac gtg ttc atg att ccg caa tac ggc tac       528
Leu Pro Pro Phe Pro Ala Asp Val Phe Met Ile Pro Gln Tyr Gly Tyr
                165                 170                 175 ctg acg ctc aac aat ggc agc caa gcc gtg gga cgt tca tcc ttt tac       576
Leu Thr Leu Asn Asn Gly Ser Gln Ala Val Gly Arg Ser Ser Phe Tyr
            180                 185                 190 tgc ctg gaa tat ttc cct tct cag atg ctg aga acg ggc aac aac ttt       624
Cys Leu Glu Tyr Phe Pro Ser Gln Met Leu Arg Thr Gly Asn Asn Phe
        195                 200                 205 acc ttc agc tac acc ttt gag gaa gtg cct ttc cac agc agc tac gcg       672
Thr Phe Ser Tyr Thr Phe Glu Glu Val Pro Phe His Ser Ser Tyr Ala
    210                 215                 220 cac agc cag agc ctg gac cgg ctg atg aat cct ctc atc gac caa tac       720
His Ser Gln Ser Leu Asp Arg Leu Met Asn Pro Leu Ile Asp Gln Tyr
225                 230                 235                 240 ctg tat tac ctg aac aga act caa aat cag tcc gga agt gcc caa aac       768
Leu Tyr Tyr Leu Asn Arg Thr Gln Asn Gln Ser Gly Ser Ala Gln Asn
                245                 250                 255 aag gac ttg ctg ttt agc cgt ggg tct cca gct ggc atg tct gtt cag       816
Lys Asp Leu Leu Phe Ser Arg Gly Ser Pro Ala Gly Met Ser Val Gln
            260                 265                 270 ccc aaa aac tgg cta cct gga ccc tgt tat cgg cag cag cgc gtt tct       864
Pro Lys Asn Trp Leu Pro Gly Pro Cys Tyr Arg Gln Gln Arg Val Ser
        275                 280                 285 aaa aca aaa aca gac aac aac aac agc aat ttt acc tgg act ggt gct       912
Lys Thr Lys Thr Asp Asn Asn Asn Ser Asn Phe Thr Trp Thr Gly Ala
    290                 295                 300 tca aaa tat aac ctc aat ggg cgt gaa tcc atc atc aac cct ggc act       960
Ser Lys Tyr Asn Leu Asn Gly Arg Glu Ser Ile Ile Asn Pro Gly Thr
305                 310                 315                 320 gct atg gcc tca cac aaa gac gac gaa gac aag ttc ttt ccc atg agc      1008
Ala Met Ala Ser His Lys Asp Asp Glu Asp Lys Phe Phe Pro Met Ser
                325                 330                 335 ggt gtc atg att ttt gga aaa gag agc gcc gga gct tca aac act gca      1056
Gly Val Met Ile Phe Gly Lys Glu Ser Ala Gly Ala Ser Asn Thr Ala
            340                 345                 350 ttg gac aat gtc atg att aca gac gaa gag gaa att aaa gcc act aac      1104
Leu Asp Asn Val Met Ile Thr Asp Glu Glu Glu Ile Lys Ala Thr Asn
        355                 360                 365
```

```
cct gtg gcc acc gaa aga ttt ggg acc gtg gca gtc aat ttc cag agc    1152
Pro Val Ala Thr Glu Arg Phe Gly Thr Val Ala Val Asn Phe Gln Ser
    370                 375                 380 agc agc aca gac cct gcg acc gga gat gtg cat gct atg gga gca tta    1200
Ser Ser Thr Asp Pro Ala Thr Gly Asp Val His Ala Met Gly Ala Leu
385                 390                 395                 400 cct ggc atg gtg tgg caa gat aga gac gtg tac ctg cag ggt ccc att    1248
Pro Gly Met Val Trp Gln Asp Arg Asp Val Tyr Leu Gln Gly Pro Ile
            405                 410                 415 tgg gcc aaa att cct cac aca gat gga cac ttt cac ccg tct cct ctt    1296
Trp Ala Lys Ile Pro His Thr Asp Gly His Phe His Pro Ser Pro Leu
        420                 425                 430 atg ggc ggc ttt gga ctc aag aac ccg cct cct cag atc ctc atc aaa    1344
Met Gly Gly Phe Gly Leu Lys Asn Pro Pro Pro Gln Ile Leu Ile Lys
                435                 440                 445 aac acg cct gtt cct gcg aat cct ccg gcg gag ttt tca gct aca aag    1392
Asn Thr Pro Val Pro Ala Asn Pro Pro Ala Glu Phe Ser Ala Thr Lys
    450                 455                 460 ttt gct tca ttc atc acc caa tac tcc aca gga caa gtg agt gtg gaa    1440
Phe Ala Ser Phe Ile Thr Gln Tyr Ser Thr Gly Gln Val Ser Val Glu
465                 470                 475                 480 att gaa tgg gag ctg cag aaa gaa aac agc aag cgc tgg aat ccc gaa    1488
Ile Glu Trp Glu Leu Gln Lys Glu Asn Ser Lys Arg Trp Asn Pro Glu
            485                 490                 495 gtg cag tac aca tcc aat tat gca aaa tct gcc aac gtt gat ttt act    1536
Val Gln Tyr Thr Ser Asn Tyr Ala Lys Ser Ala Asn Val Asp Phe Thr
        500                 505                 510 gtg gac aac aat gga ctt tat act gag cct cgc ccc att ggc acc cgt    1584
Val Asp Asn Asn Gly Leu Tyr Thr Glu Pro Arg Pro Ile Gly Thr Arg
                515                 520                 525 tac ctt acc cgt ccc ctg taa                                        1605
Tyr Leu Thr Arg Pro Leu
    530

<210> SEQ ID NO 25
<211> LENGTH: 534
<212> TYPE: PRT
<213> ORGANISM: Artificial sequence
<220> FEATURE:
<223> OTHER INFORMATION: Synthetic Construct

<400> SEQUENCE: 25

Met Ala Ser Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Thr Asn Asp Gly Val
        115                 120                 125

Thr Thr Ile Ala Asn Asn Leu Thr Ser Thr Val Gln Val Phe Ser Asp
```

```
            130                 135                 140
Ser Glu Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asn Gly Ser Gln Ala Val Gly Arg Ser Ser Phe Tyr
                180                 185                 190

Cys Leu Glu Tyr Phe Pro Ser Gln Met Leu Arg Thr Gly Asn Asn Phe
                195                 200                 205

Thr Phe Ser Tyr Thr Phe Glu Glu Val Pro Phe His Ser Ser Tyr Ala
        210                 215                 220

His Ser Gln Ser Leu Asp Arg Leu Met Asn Pro Leu Ile Asp Gln Tyr
225                 230                 235                 240

Leu Tyr Tyr Leu Asn Arg Thr Gln Asn Gln Ser Gly Ser Ala Gln Asn
                245                 250                 255

Lys Asp Leu Leu Phe Ser Arg Gly Ser Pro Ala Gly Met Ser Val Gln
                260                 265                 270

Pro Lys Asn Trp Leu Pro Gly Pro Cys Tyr Arg Gln Gln Arg Val Ser
            275                 280                 285

Lys Thr Lys Thr Asp Asn Asn Asn Ser Asn Phe Thr Trp Thr Gly Ala
290                 295                 300

Ser Lys Tyr Asn Leu Asn Gly Arg Glu Ser Ile Ile Asn Pro Gly Thr
305                 310                 315                 320

Ala Met Ala Ser His Lys Asp Asp Glu Asp Lys Phe Phe Pro Met Ser
                325                 330                 335

Gly Val Met Ile Phe Gly Lys Glu Ser Ala Gly Ala Ser Asn Thr Ala
                340                 345                 350

Leu Asp Asn Val Met Ile Thr Asp Glu Glu Ile Lys Ala Thr Asn
                355                 360                 365

Pro Val Ala Thr Glu Arg Phe Gly Thr Val Ala Val Asn Phe Gln Ser
        370                 375                 380

Ser Ser Thr Asp Pro Ala Thr Gly Asp Val His Ala Met Gly Ala Leu
385                 390                 395                 400

Pro Gly Met Val Trp Gln Asp Arg Asp Val Tyr Leu Gln Gly Pro Ile
                405                 410                 415

Trp Ala Lys Ile Pro His Thr Asp Gly His Phe His Pro Ser Pro Leu
                420                 425                 430

Met Gly Gly Phe Gly Leu Lys Asn Pro Pro Gln Ile Leu Ile Lys
            435                 440                 445

Asn Thr Pro Val Pro Ala Asn Pro Pro Ala Glu Phe Ser Ala Thr Lys
450                 455                 460

Phe Ala Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Val Gln Tyr Thr Ser Asn Tyr Ala Lys Ser Ala Asn Val Asp Phe Thr
                500                 505                 510

Val Asp Asn Asn Gly Leu Tyr Thr Glu Pro Arg Pro Ile Gly Thr Arg
            515                 520                 525

Tyr Leu Thr Arg Pro Leu
            530

<210> SEQ ID NO 26
```

```
<211> LENGTH: 19
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(19)
<223> OTHER INFORMATION: CMV gene

<400> SEQUENCE: 26
aatgggcggt aggcgtgta                                                   19

<210> SEQ ID NO 27
<211> LENGTH: 22
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (1)..(22)
<223> OTHER INFORMATION: CMV gene

<400> SEQUENCE: 27
aggcgatctg acggttcact aa                                               22

<210> SEQ ID NO 28
<211> LENGTH: 11954
<212> TYPE: DNA
<213> ORGANISM: Artificial sequence
<220> FEATURE:
<223> OTHER INFORMATION: pVD84 vector

<400> SEQUENCE: 28
gggtgatcaa gtcttcgtcg agtgattgta aataaaatgt aatttacagt atagtatttt      60
aattaatata caaatgattt gataataatt cttatttaac tataatatat tgtgttgggt     120
tgaattaaag gtccgtatac tccggaatat taatagatca tggagataat taaaatgata     180
accatctcgc aaataaataa gtattttact gttttcgtaa cagttttgta ataaaaaaac     240 ctataaaatat tccggattat tcataccgtc ccaccatcgg gcgcggatcc tgttaaggtg     300
gctgccgacg gttatctacc cgattggctc gaggacaacc tctctgaggg cattcgcgag     360
tggtgggact tgaaacctgg agccccgaag cccaaagcca accagcaaaa gcaggacgac     420
ggccggggtc tggtgcttcc tggctacaag tacctcggac ccttcaacgg actcgacaag     480
ggggagcccg tcaacgcggc ggacgcagcg ccctcgagc acgacaaggc ctacgaccag     540
cagctcaaag cgggtgacaa tccgtacctg cggtataacc acgccgacgc cgagtttcag     600
gagcgtctgc aagaagatac gtcttttggg ggcaacctcg ggcgagcagt cttccaggcc     660
aagaagcggg ttctcgaacc tctcggtctg gttgaggaag gcgctaagac ggctcctgga     720
aagaaacgtc cggtagagca gtcgccacaa gagccagact cctcctcggg catcggcaag     780
acaggccagc agcccgctaa aaagagactc aattttggtc agactggcga ctcagagtca     840
gtccccgatc cacaacctct cggagaacct ccagcaaccc ccgctgctgt gggacctact     900
acaatggctt caggcggtgg cgcaccaatg gcagacaata acgaaggcgc cgacggagtg     960
ggtaatgcct caggaaattg gcattgcgat tccacatggc tgggcgacag agtcatcacc    1020
accagcaccc gcacctgggc cttgcccacc tacaataacc acctctacaa gcaaatctcc    1080
agtgcttcaa cgggggccag caacgacaac cactacttcg gctacagcac cccctgggg    1140 tattttgatt tcaacagatt ccactgccac ttttcaccac gtgactggca gcgactcatc    1200
```

```
aacaacaatt ggggattccg gcccaagaga ctcaacttca aactcttcaa catccaagtc   1260
aaggaggtca cgacgaatga tggcgtcaca accatcgcta ataaccttac cagcacggtt   1320
caagtcttct cggactcgga gtaccagctt ccgtacgtcc tcggctctgc gcaccagggc   1380
tgcctccctc cgttcccggc ggacgtgttc atgattccgc aatacggcta cctgacgctc   1440
aacaatggca gccaagccgt gggacgttca tccttttact gcctggaata tttcccttct   1500
cagatgctga gaacgggcaa caactttacc ttcagctaca cctttgagga agtgcctttc   1560
cacagcagct acgcgcacag ccagagcctg gaccggctga tgaatcctct catcgaccaa   1620
tacctgtatt acctgaacag aactcaaaat cagtccggaa gtgcccaaaa caaggacttg   1680
ctgtttagcc gtgggtctcc agctggcatg tctgttcagc ccaaaaactg gctacctgga   1740
ccctgttatc ggcagcagcg cgtttctaaa acaaaaacag acaacaacaa cagcaatttt   1800
acctggactg gtgcttcaaa atataacctc aatgggcgtg aatccatcat caaccctggc   1860
actgctatgg cctcacacaa agacgacgaa gacaagttct ttcccatgag cggtgtcatg   1920 attttttggaa aagagagcgc cggagcttca aacactgcat ggacaatgt catgattaca   1980 gacgaagagg aaattaaagc cactaaccct gtggccaccg aaagatttgg gaccgtggca   2040
gtcaatttcc agagcagcag cacagaccct gcgaccggag atgtgcatgc tatgggagca   2100
ttacctggca tggtgtggca agatagagac gtgtacctgc agggtcccat ttgggccaaa   2160
attcctcaca cagatggaca cttttcaccc g tctcctctta tgggcggctt tggactcaag   2220
aacccgcctc ctcagatcct catcaaaaac acgcctgttc ctgcgaatcc tccggcggag   2280
ttttcagcta caaagtttgc ttcattcatc acccaatact ccacaggaca agtgagtgtg   2340
gaaattgaat gggagctgca gaaagaaaac agcaagcgct ggaatcccga agtgcagtac   2400
acatccaatt atgcaaaatc tgccaacgtt gattttactg tggacaacaa tggactttat   2460
actgagcctc gccccattgg cacccgttac cttacccgtc ccctgtaagc aagggcgaat   2520
tctgcagata tccatcacac tggcggccgc tttcgaatct agagcctgca gtctcgacaa   2580
gcttgtcgag aagtactaga ggatcataat cagccatacc acatttgtag aggttttact   2640
tgctttaaaa aacctcccac acctccccct gaacctgaaa cataaaatga atgcaattgt   2700
tgttgttaac ttgttattg cagcttataa tggttacaaa taaagcaata gcatcacaaa   2760
tttcacaaat aaagcatttt tttcactgca ttctagttgt ggtttgtcca aactcatcaa   2820
tgtatcttat catgtctgga tctgatcact gcttgagcct agaggcctcg cgagatctta   2880
attaattaag taccgactct gctgaagagg aggaaattct ccttgaagtt ccctggtgt   2940 tcaaagtaaa ggagtttgca ccagacgcac ctctgttcac tggtccggcg tattaaaaca   3000
cgatacattg ttattagtac atttattaag cgctagattc tgtgcgttgt tgatttacag   3060
acaattgttg tacgtatttt aataattcat taaatttata atctttaggg tggtatgtta   3120
gagcgaaaat caaatgattt tcagcgtctt tatatctgaa tttaaatatt aaatcctcaa   3180
tagatttgta aaataggttt cgattagttt caaacaaggg ttgttttttcc gaaccgatgg   3240 ctggactatc taatggattt tcgctcaacg ccacaaaact tgccaaatct tgtagcagca   3300
atctagcttt gtcgatattc gtttgtgttt tgttttgtaa taaaggttcg acgtcgttca   3360
aaatattatg cgcttttgta tttctttcat cactgtcgtt agtgtacaat tgactcgacg   3420
taaacacgtt aaataaagct tggacatatt taacatcggg cgtgttagct ttattaggcc   3480
gattatcgtc gtcgtcccaa ccctcgtcgt tagaagttgc ttccgaagac gattttgcca   3540
```

```
tagccacacg acgcctatta attgtgtcgg ctaacacgtc cgcgatcaaa tttgtagttg    3600
agcttttggg aattatttct gattgcgggc gttttggggc gggtttcaat ctaactgtgc    3660
ccgattttaa ttcagacaac acgttagaaa gcgatggtgc aggcggtggt aacatttcag    3720
acggcaaatc tactaatggc ggcggtggtg gagctgatga taaatctacc atcggtggag    3780
gcgcaggcgg ggctggcggc ggaggcggag gcggaggtgg tggcggtgat gcagacggcg    3840
gtttaggctc aaatgtctct ttaggcaaca cagtcggcac ctcaactatt gtactggttt    3900
cgggcgccgt ttttggtttg accggtctga gacgagtgcg attttttttcg tttctaatag    3960
cttccaacaa ttgttgtctg tcgtctaaag gtgcagcggg ttgaggttcc gtcggcattg    4020
gtggagcggg cggcaattca gacatcgatg gtggtggtgg tggtggaggc gctggaatgt    4080
taggcacggg agaaggtggt ggcggcggtg ccgccggtat aatttgttct ggtttagttt    4140
gttcgcgcac gattgtgggc accggcgcag gcgccgctgg ctgcacaacg gaaggtcgtc    4200
tgcttcgagg cagcgcttgg ggtggtggca attcaatatt ataattggaa tacaaatcgt    4260
aaaaatctgc tataagcatt gtaatttcgc tatcgtttac cgtgccgata tttaacaacc    4320
gctcaatgta agcaattgta ttgtaaagag attgtctcaa gctcggatcc cgcacgccga    4380
taacaagcct tttcattttt actacagcat tgtagtggcg agacacttcg ctgtcgtcga    4440
cgtacatgta tgctttgttg tcaaaaacgt cgttggcaag cttttaaaata tttaaaagaa    4500
catctctgtt cagcaccact gtgttgtcgt aaatgttgtt tttgataatt tgcgcttccg    4560
cagtatcgac acgttcaaaa aattgatgcg catcaatttt gttgttccta ttattgaata    4620
aataagattg tacagattca tatctacgat tcgtcatggc caccacaaat gctacgctgc    4680
aaacgctggt acaattttac gaaaactgca aaaacgtcaa aactcggtat aaaataatca    4740
acgggcgctt tggcaaaata tctattttat cgcacaagcc cactagcaaa ttgtatttgc    4800
agaaaacaat ttcggcgcac aatttttaacg ctgacgaaat aaaagttcac cagttaatga    4860
gcgaccaccc aaattttata aaaatctatt ttaatcacgg ttccatcaac aaccaagtga    4920
tcgtgatgga ctacattgac tgtcccgatt tatttgaaac actacaaatt aaaggcgagc    4980
tttcgtacca acttgttagc aatattatta gacagctgtg tgaagcgctc aacgatttgc    5040
acaagcacaa tttcatacac aacgacataa aactcgaaaa tgtcttatat ttcgaagcac    5100
ttgatcgcgt gtatgtttgc gattacggat tgtgcaaaca cgaaaactca cttagcgtgc    5160
acgacggcac gttggagtat tttagtccgg aaaaaattcg acacacaact atgcacgttt    5220
cgtttgactg gtacgcggcg tgttaacata caagttgcta accggcggcc gacacccatt    5280
tgaaaaaagc gaagacgaaa tgttggactt gaatagcatg aagcgtcgtc agcaatacaa    5340
tgacattggc gttttaaaac acgttcgtaa cgttaacgct cgtgactttg tgtactgcct    5400
aacaagatac aacatagatt gtagactcac aaattacaaa caaattataa acatgagtt     5460
tttgtcgtaa aaatgccact tgttttacga gtagaattcg taatcatggt catagctgtt    5520
tcctgtgtga aattgttatc cgctcacaat tccacacaac atacgagccg gaagcataaa    5580
gtgtaaagcc tgggggtgcct aatgagtgag ctaactcaca ttaattgcgt tgcgctcact    5640
gcccgctttc cagtcgggaa acctgtcgtg ccagctgcat taatgaatcg gccaacgcgc    5700
ggggagaggc ggtttgcgta ttgggcgctc ttccgcttcc tcgctcactg actcgctgcg    5760
ctcggtcgtt cggctgcggc gagcggtatc agctcactca aaggcggtaa tacggttatc    5820
cacagaatca ggggataacg caggaaagaa catgtgagca aaaggccagc aaaaggccag    5880
gaaccgtaaa aaggccgcgt tgctggcgtt tttccatagg ctccgccccc ctgacgagca    5940
```

```
tcacaaaaat cgacgctcaa gtcagaggtg gcgaaacccg acaggactat aaagatacca    6000
ggcgtttccc cctggaagct ccctcgtgcg ctctcctgtt ccgaccctgc cgcttaccgg    6060
atacctgtcc gccttctcc cttcgggaag cgtggcgctt tctcatagct cacgctgtag    6120
gtatctcagt tcggtgtagg tcgttcgctc caagctgggc tgtgtgcacg aaccccccgt    6180
tcagcccgac cgctgcgcct tatccggtaa ctatcgtctt gagtccaacc cggtaagaca    6240
cgacttatcg ccactggcag cagccactgg taacaggatt agcagagcga ggtatgtagg    6300
cggtgctaca gagttcttga agtggtggcc taactacggc tacactagaa ggacagtatt    6360
tggtatctgc gctctgctga agccagttac cttcggaaaa agagttggta gctcttgatc    6420
cggcaaacaa accaccgctg gtagcggtgg ttttttttgtt tgcaagcagc agattacgcg    6480
cagaaaaaaa ggatctcaag aagatccttt gatcttttct acggggtctg acgctcagtg    6540
gaacgaaaac tcacgttaag ggattttggt catgagatta tcaaaaagga tcttcaccta    6600 gatccttta aattaaaaat gaagttttaa atcaatctaa agtatatatg agtaaacttg    6660
gtctgacagt taccaatgct taatcagtga ggcacctatc tcagcgatct gtctatttcg    6720
ttcatccata gttgcctgac tccccgtcgt gtagataact acgatacggg agggcttacc    6780
atctggcccc agtgctgcaa tgataccgcg agacccacgc tcaccggctc cagatttatc    6840
agcaataaac cagccagccg gaagggccga gcgcagaagt ggtcctgcaa ctttatccgc    6900
ctccatccag tctattaatt gttgccggga agctagagta agtagttcgc cagttaatag    6960
tttgcgcaac gttgttgcca ttgctacagg catcgtggtg tcacgctcgt cgtttggtat    7020
ggcttcattc agctccggtt cccaacgatc aaggcgagtt acatgatccc ccatgttgtg    7080
caaaaaagcg gttagctcct tcggtcctcc gatcgttgtc agaagtaagt tggccgcagt    7140
gttatcactc atggttatgg cagcactgca taattctctt actgtcatgc catccgtaag    7200
atgcttttct gtgactggtg agtactcaac caagtcattc tgagaatagt gtatgcggcg    7260
accgagttgc tcttgcccgg cgtcaatacg ggataatacc gcgccacata gcagaacttt    7320
aaaagtgctc atcattggaa aacgttcttc ggggcgaaaa ctctcaagga tcttaccgct    7380
gttgagatcc agttcgatgt aacccactcg tgcacccaac tgatcttcag catcttttac    7440
tttcaccagc gtttctgggt gagcaaaaac aggaaggcaa aatgccgcaa aaaagggaat    7500
aagggcgaca cggaaatgtt gaatactcat actcttcctt tttcaatatt attgaagcat    7560
ttatcagggt tattgtctca tgagcggata catatttgaa tgtatttaga aaaataaaca    7620
aataggggtt ccgcgcacat ttccccgaaa agtgccacct gacgtctaag aaaccattat    7680
tatcatgaca ttaacctata aaaataggcg tatcacgagg ccctttcgtc tcgcgcgttt    7740
cggtgatgac ggtgaaaacc tctgacacat gcagctcccg gagacggtca cagcttgtct    7800
gtaagcggat gccgggagca gacaagcccg tcagggcgcg tcagcgggtg ttggcgggtg    7860
tcggggctgg cttaactatg cggcatcaga gcagattgta ctgagagtgc accatatgcg    7920
gtgtgaaata ccgcacagat gcgtaaggag aaaataccgc atcaggcgcc attcgccatt    7980
caggctgcgc aactgttggg aagggcgatc ggtgcgggcc tcttcgctat tacgccagct    8040
ggcgaaaggg ggatgtgctg caaggcgatt aagttgggta acgccagggt tttcccagtc    8100
acgacgttgt aaaacgaccg agttgtttgc gtacgtgact agcgaagaag atgtgtggac    8160
cgcagaacag atagtaaaac aaaacccctag tattggagca ataatcgatt taaccaacac    8220
gtctaaatat tatgatggtg tgcattttt gcgggcgggc ctgttataca aaaaaattca    8280
```

```
agtacctggc cagactttgc cgcctgaaag catagttcaa gaatttattg acacggtaaa    8340
agaatttaca gaaaagtgtc ccggcatgtt ggtgggcgtg cactgcacac acggtattaa    8400
tcgcaccggt tacatggtgt gcagatattt aatgcacacc ctgggtattg cgccgcagga    8460
agccatagat agattcgaaa aagccagagg tcacaaaatt gaaagacaaa attacgttca    8520
agatttatta atttaattaa tattatttgc attcttaac aaatacttta tcctatttc     8580 aaattgttgc gcttcttcca gcgaaccaaa actatgcttc gcttgctccg tttagcttgt    8640
agccgatcag tggcgttgtt ccaatcgacg gtaggattag gccggatatt ctccaccaca    8700
atgttggcaa cgttgatgtt acgtttatgc ttttggtttt ccacgtacgt cttttggccg    8760
gtaatagccg taaacgtagt gccgtcgcgc gtcacgcaca acaccggatg tttgcgcttg    8820 tccgcgggt attgaaccgc gcgatccgac aaatccacca cttggcaac taaatcggtg      8880 acctgcgcgt cttttttctg cattatttcg tctttctttt gcatggtttc ctggaagccg    8940
gtgtacatgc ggtttagatc agtcatgacg cgcgtgacct gcaaatcttt ggcctcgatc    9000
tgcttgtcct tgatggcaac gatgcgttca ataaactctt gttttttaac aagttcctcg    9060
gttttttgcg ccaccaccgc ttgcagcgcg tttgtgtgct cggtgaatgt cgcaatcagc    9120
ttagtcacca actgtttgct ctcctcctcc cgttgtttga tcgcgggatc gtacttgccg    9180
gtgcagagca cttgaggaat tacttcttct aaaagccatt cttgtaattc tatggcgtaa    9240
ggcaatttgg acttcataat cagctgaatc acgccggatt tagtaatgag cactgtatgc    9300
ggctgcaaat acagcgggtc gcccctttc acgacgctgt tagaggtagg gccccccattt    9360 tggatggtct gctcaaataa cgatttgtat ttattgtcta catgaacacg tatagcttta    9420
tcacaaactg tatatttaa actgttagcg acgtccttgg ccacgaaccg gacctgttgg     9480
tcgcgctcta gcacgtaccg caggttgaac gtatcttctc caaatttaaa ttctccaatt    9540
ttaacgcgag ccattttgat acacgtgtgt cgattttgca acaactattg ttttttaacg    9600
caaactaaac ttattgtggt aagcaataat taaatatggg ggaacatgcg ccgctacaac    9660
actcgtcgtt atgaacgcag acggcgccgg tctcggcgca agcggctaaa acgtgttgcg    9720
cgttcaacgc ggcaaacatc gcaaaagcca atagtacagt tttgatttgc atattaacgg    9780
cgatttttta aattatctta tttaataaat agttatgacg cctacaactc cccgcccgcg    9840
ttgactcgct gcacctcgag cagttcgttg acgccttcct ccgtgtggcc gaacacgtcg    9900
agcgggtggt cgatgaccag cggcgtgccg cacgcgacgc acaagtatct gtacaccgaa    9960
tgatcgtcgg gcgaaggcac gtcggcctcc aagtggcaat attggcaaat tcgaaaatat   10020
atacagttgg gttgtttgcg catatctatc gtggcgttgg gcatgtacgt ccgaacgttg   10080
atttgcatgc aagccgaaat taaatcattg cgattagtgc gattaaaacg ttgtacatcc   10140
tcgcttttaa tcatgccgtc gattaaatcg cgcaatcgag tcaagtgatc aaagtgtgga   10200
ataatgtttt ctttgtattc ccgagtcaag cgcagcgcgt attttaacaa actagccatc   10260
ttgtaagtta gtttcatta atgcaacttt atccaataat atattatgta tcgcacgtca    10320
agaattaaca atgcgcccgt tgtcgcatct caacacgact atgatagaga tcaaataaag   10380
cgcgaattaa atagcttgcg acgcaacgtg cacgatctgt gcacgcgttc cggcacgagc   10440
tttgattgta ataagttttt acgaagcgat gacatgaccc ccgtagtgac aacgatcacg   10500
cccaaaagaa ctgccgacta caaaattacc gagtatgtcg gtgacgttaa aactattaag   10560
ccatccaatc gaccgttagt cgaatcagga ccgctggtgc gagaagccgc gaagtatggc   10620
gaatgcatcg tataacgtgt ggagtccgct cattagagcg tcatgtttag acaagaaagc   10680
```

```
tacatattta attgatcccg atgatttat tgataaattg accctaactc catacacggt    10740
attctacaat ggcggggttt tggtcaaaat ttccggactg cgattgtaca tgctgttaac    10800
ggctccgccc actattaatg aaattaaaaa ttccaatttt aaaaaacgca gcaagagaaa    10860
catttgtatg aaagaatgcg tagaaggaaa gaaaaatgtc gtcgacatgc tgaacaacaa    10920
gattaatatg cctccgtgta taaaaaaaat attgaacgat ttgaaagaaa acaatgtacc    10980
gcgcggcggt atgtacagga agaggtttat actaaactgt tacattgcaa acgtggtttc    11040
gtgtgccaag tgtgaaaacc gatgtttaat caaggctctg acgcatttct acaaccacga    11100
ctccaagtgt gtgggtgaag tcatgcatct tttaatcaaa tcccaagatg tgtataaacc    11160
accaaactgc caaaaaatga aaactgtcga caagctctgt ccgtttgctg gcaactgcaa    11220
gggtctcaat cctatttgta attattgaat aataaaacaa ttataaatgc taaatttgtt    11280
ttttattaac gatacaaacc aaacgcaaca agaacatttg tagtattatc tataattgaa    11340
aacgcgtagt tataatcgct gaggtaatat ttaaaatcat tttcaaatga ttcacagtta    11400
atttgcgaca atataatttt attttcacat aaactagacg ccttgtcgtc ttcttcttcg    11460
tattccttct cttttcatt tttctcctca taaaaattaa catagttatt atcgtatcca    11520
tatatgtatc tatcgtatag agtaaatttt ttgttgtcat aaatatatat gtctttttta    11580
atggggtgta tagtaccgct gcgcatagtt tttctgtaat ttacaacagt gctattttct    11640
ggtagttctt cggagtgtgt tgctttaatt attaaattta tataatcaat gaatttggga    11700
tcgtcggttt tgtacaatat gttgccggca tagtacgcag cttcttctag ttcaattaca    11760 ccattttta gcagcaccgg attaacataa ctttccaaaa tgttgtacga accgttaaac    11820
aaaaacagtt cacctccctt ttctatacta ttgtctgcga gcagttgttt gttgttaaaa    11880
ataacagcca ttgtaatgag acgcacaaac taatatcaca aactggaaat gtctatcaat    11940
atatagttgc tgat                                                     11954
```

<210> SEQ ID NO 29
<211> LENGTH: 30
<212> TYPE: DNA
<213> ORGANISM: Artificial sequence
<220> FEATURE:
<223> OTHER INFORMATION: primer sequence (forward, comprising BamHI site)

<400> SEQUENCE: 29
ttaggatcct gttaaggtgg ctgccgacgg                                     30

<210> SEQ ID NO 30
<211> LENGTH: 30
<212> TYPE: DNA
<213> ORGANISM: Artificial sequence
<220> FEATURE:
<223> OTHER INFORMATION: primer sequence (reverse, comprising StuI site)

<400> SEQUENCE: 30
gtcgtaggcc ttgtcgtgct cgagggccgc                                     30

<210> SEQ ID NO 31
<211> LENGTH: 1966
<212> TYPE: DNA
<213> ORGANISM: adeno-associated virus 2
<220> FEATURE:
<221> NAME/KEY: misc_feature
<222> LOCATION: (1)..(1966)
<223> OTHER INFORMATION: rep with CTG start codon and no internal ATG

<400> SEQUENCE: 31

```
cggtccgaag cgcgcggaat tcaaaggcct acgtcgacga ggggagatct gccgccctgg      60
cggggtttta cgagattgtg attaaggtcc ccagcgacct tgacgagcat ctgcccggca     120
tttctgacag ctttgtgaac tgggtggccg agaaggagtg ggagttgccg ccagattctg     180
acttggatct gaatctgatt gagcaggcac ccctgaccgt ggccgagaag ctgcagcgcg     240
actttctgac ggagtggcgc cgtgtgagta aggccccgga ggcccttttc tttgtgcaat     300
ttgagaaggg agagagctac ttccacttac acgtgctcgt ggaaaccacc ggggtgaaat     360
ccttagtttt gggacgtttc ctgagtcaga ttcgcgaaaa actgattcag agaatttacc     420
gcgggatcga gccgactttg ccaaactggt tcgcggtcac aaagaccaga aacggcgccg     480
gaggcgggaa caaggtggtg gacgagtgct acatccccaa ttacttgctc cccaaaaccc     540
agcctgagct ccagtgggcg tggactaatt tagaacagta tttaagcgcc tgtttgaatc     600
tcacggagcg taaacggttg gtggcgcagc atctgacgca cgtgtcgcag acgcaggagc     660
agaacaaaga gaatcagaat cccaattctg acgcgccggt gatcagatca aaaacttcag     720
ccaggtacat ggagctggtc gggtggctcg tggacaaggg gattacctcg gagaagcagt     780
ggatccagga ggaccaggcc tcatacatct ccttcaatgc ggcctccaac tcgcggtccc     840
aaatcaaggc tgccttggac aatgcgggaa agattatgag cctgactaaa accgcccccg     900
actacctggt gggccagcag cccgtggagg acatttccag caatcggatt tataaaattt     960
tggaactaaa cgggtacgat ccccaatatg cggcttccgt ctttctggga tgggccacga    1020
aaaagttcgg caagaggaac accatctggc tgtttgggcc tgcaactacc gggaagacca    1080
acatcgcgga ggccatagcc cacactgtgc ccttctacgg gtgcgtaaac tggaccaatg    1140
agaactttcc cttcaacgac tgtgtcgaca agatggtgat ctggtgggag gagggggaaga   1200
tgaccgccaa ggtcgtggag tcggccaaag ccattctcgg aggaagcaag gtgcgcgtgg    1260
accagaaatg caagtcctcg gcccagatag acccgactcc cgtgatcgtc acctccaaca    1320
ccaacatgtg cgccgtgatt gacgggaact caacgaccct cgaacaccag cagccgttgc    1380
aagaccggat gttcaaattt gaactcaccc gccgtctgga tcatgacttt gggaaggtca    1440
ccaagcagga agtcaaagac ttttttccggt gggcaaagga tcacgtggtt gaggtggagc    1500
atgaattcta cgtcaaaaag ggtggagcca agaaaagacc cgcccccagt gacgcagata    1560
taagtgagcc caaacgggtg cgcgagtcag ttgcgcagcc atcgacgtca gacgcggaag    1620
cttcgatcaa ctacgcagac aggtaccaaa acaaatgttc tcgtcacgtg ggcatgaatc    1680
tgatgctgtt tccctgcaga caatgcgaga gaatgaatca gaattcaaat atctgcttca    1740
ctcacggaca gaaagactgt ttagagtgct ttcccgtgtc agaatctcaa cccgtttctg    1800
tcgtcaaaaa ggcgtatcag aaactgtgct acattcatca tatcatggga aaggtgccag    1860
acgcttgcac tgcctgcgat ctggtcaatg tggatttgga tgactgcatc tttgaacaat    1920
aaactcgagg acaatcaagc ttgcatgcct gcaggtcgac tctaga                   1966
```

OPTIMIZATION OF EXPRESSION OF PARVOVIRAL REP AND CAP PROTEINS IN INSECT CELLS

FIELD OF THE INVENTION

This invention relates to the production of parvovirus vectors, especially to the production of recombinant adeno-associated viruses (rAAV) in insect cells, baculoviral expression vectors comprising a construct of the invention and a cell comprising such a baculoviral expression vector.

BACKGROUND OF THE INVENTION

The baculovirus expression system is well known for its use as eukaryotic cloning and expression vector (King, L A & R D Possee, 1992, *The baculovirus expression system*, Chapman and Hall, UK; O'Reilly, D R et al., 1992. *Baculovirus Expression Vectors: A Laboratory Manual*. New York: W.H. Freeman). Advantages of the baculovirus expression system are among others that the expressed proteins are almost always soluble, correctly folded and biologically active. Further advantages include high protein expression levels, faster production, suitability for expression of large proteins and suitability for large-scale production. However, in large-scale or continuous production of heterologous proteins using the baculovirus expression system in insect cell bioreactors, the instability of production levels, also known as the passage effect, is a major obstacle. This effect is at least in part due to recombination between repeated homologous sequences in the baculoviral DNA.

The baculovirus expression system has also successfully been used for the production of recombinant adeno-associated virus (AAV) vectors (Urabe et al., 2002, *Hum. Gene Ther.* 13:1935-43; U.S. Pat. No. 6,723,551 and US 2004/0197895). AAV may be considered as one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans it has never been associated with any disease. In view of these advantages, recombinant adeno-associated virus (rAAV) is being evaluated in gene therapy clinical trials for hemophilia B, malignant melanoma, cystic fibrosis, hyperlipoproteinemia type I and other diseases.

To overcome problems with mammalian productions systems for AAV (Urabe et al., 2002, supra) developed an AAV production system in insect cells. For production of AAV in insect cells some modifications were necessary in order to achieve the correct stoichiometry of the three AAV capsid proteins (VP1, VP2 and VP3), which relies on a combination of alternate usage of two splice acceptor sites and the suboptimal utilization of an ACG initiation codon for VP2 that is not accurately reproduced by insect cells. To mimic the correct stoichiometry of the capsid proteins in insect cells Urabe et al. (2002, supra) use a construct that is transcribed into a single polycistronic messenger that is able to express all three VP proteins without requiring splicing and wherein the most upstream initiator codon is replaced by the suboptimal initiator codon ACG. WO2007/046703 discloses further improvement of the infectivity of baculovirus-produced rAAV vectors based production by optimisation of the stoichiometry of AAV capsid proteins as produced in insect cells.

For expression of the AAV Rep proteins in the AAV insect cell expression system as initially developed by Urabe et al. (2002, supra), a recombinant baculovirus construct is used that harbours two independent Rep expression units (one for Rep78 and one for Rep52), each under the control of a separate insect cell promoter, the ΔIE1 and PolH promoters, respectively. However, Kohlbrenner et al. (2005, *Mol. Ther.* 12 1217-25; and WO2005/072364) reported that the baculovirus construct for expression of the two Rep proteins, as used by Urabe et al. (supra) suffers from an inherent instability. By splitting the palindromic orientation of the two Rep genes in Urabe's (supra) original vector and designing two separate baculovirus vectors for expressing Rep52 and Rep78, Kohlbrenner et al. (supra) increased the passaging stability of the vector. However, despite the consistent expression of Rep78 and Rep52 from the two independent baculovirus-Rep constructs in insect cells over at least 5 passages, rAAV vector yield is 5 to 10-fold lower as compared to the original baculovirus-Rep construct designed by Urabe et al. (2002, supra).

In WO2007/148971, the present inventors have significantly improved the stability of rAAV vector production in insect cells by using a single coding sequence for the Rep78 and Rep52 proteins wherein a suboptimal initiator codon is used for the Rep78 protein that is partially skipped by the scanning ribosomes to allow for initiation of translation to also occur further downstream at the initiation codon of the Rep52 protein.

International patent application WO 2007/084773 discloses a method of rAAV production in insect cells, wherein the production of infectious viral particles is increased by supplementing VP1 relative to VP2 and VP3. Supplementation can be effected by introducing into the insect cell a capsid vector comprising nucleotide sequences expressing VP1, VP2 and VP3 and additionally introducing into the insect cell a nucleotide sequences expressing VP1, which may be either on the same capsid vector or on a different vector.

There is however still a need for further improvements in large scale (commercial) production of parvoviral vectors in insect cells. Thus it is an object of the present invention to provide for means and methods that allow for stable and high yield (large scale) production of parvoviral vectors and for production which results in an improved full:empty particle ratio (i.e., a greater proportion of filled particles).

SUMMARY OF THE INVENTION

The invention relates to a method for the production of a recombinant parvoviral virion. The use of such a method may allow for the production of such virions at increased production titres. The use of the method may alternatively, or additionally, allow production having a greater proportion of filled particles, i.e., a more favourable full:empty ratio or total:full ratio.

The invention provides a method for the production of a recombinant parvoviral virion, which method comprises the steps of:
(a) providing an insect cell comprising one or more nucleic acid constructs comprising:
  (i) a nucleotide sequence comprising a transgene that is flanked by at least one parvoviral inverted terminal repeat nucleotide sequence;
  (ii) a first expression cassette comprising a nucleotide sequence encoding a parvoviral Rep protein which is operably linked to a first promoter that is capable of driving expression of the Rep protein in the insect cell;
  (iii) a second expression cassette comprising a nucleotide sequence encoding a parvoviral capsid protein which is operably linked to a second promoter that is capable of driving expression of the capsid protein in the insect cell;

(b) culturing the cell defined in (a) under a condition conducive to the expression of the Rep and the capsid protein; and,
(c) optionally recovering of the recombinant parvoviral virion;
wherein the first and second expression cassettes are present on a single nucleic acid construct and wherein the first and second expression cassettes, when present in equimolar amount in the insect cell produce a ratio of levels of Rep protein encoding mRNA versus capsid protein encoding mRNA of at least 0.5 as determined by quantitative reverse-transcription PCR at a time point between 24 and 72 hours after transfection.

The invention also provides
a nucleic acid construct comprising a first and a second expression cassette as defined above, wherein:
(a) the first promoter is a p10 promoter and the second promoter is a PolH promoter or a 4×Hsp27 EcRE+minimal Hsp70 promoter;
(b) the first promoter is a 4×Hsp27 EcRE+minimal Hsp70 promoter and the second promoter is a PolH promoter;
(c) the first promoter is a PolH promoter and the second promoter is a p10, a deltaIE1 or an IE1 promoter;
(d) the first promoter is a PolH promoter and the second promoter is a deltaIE1 or an IE1 promoter;
(e) the first promoter is a p10 promoter and the second promoter is a deltaIE1 or an IE1 promoter; or
(f) the first promoter is a PolH promoter and the second promoter is a PolH promoter.
and wherein the first expression cassette optionally comprises an enhancer element;
an insect cell as defined above; and
a kit comprising
(a) a nucleic acid construct comprising the first and second expression cassette as defined above; and
(b) a nucleic acid construct comprising a nucleotide sequence encoding a multiple cloning site for a transgene that is flanked by at least one parvoviral inverted terminal repeat nucleotide sequence, which transgene is operably linked to a promoter capable of driving expression of the transgene in a host cell.

DESCRIPTION OF THE INVENTION

Definitions

Figure 1:
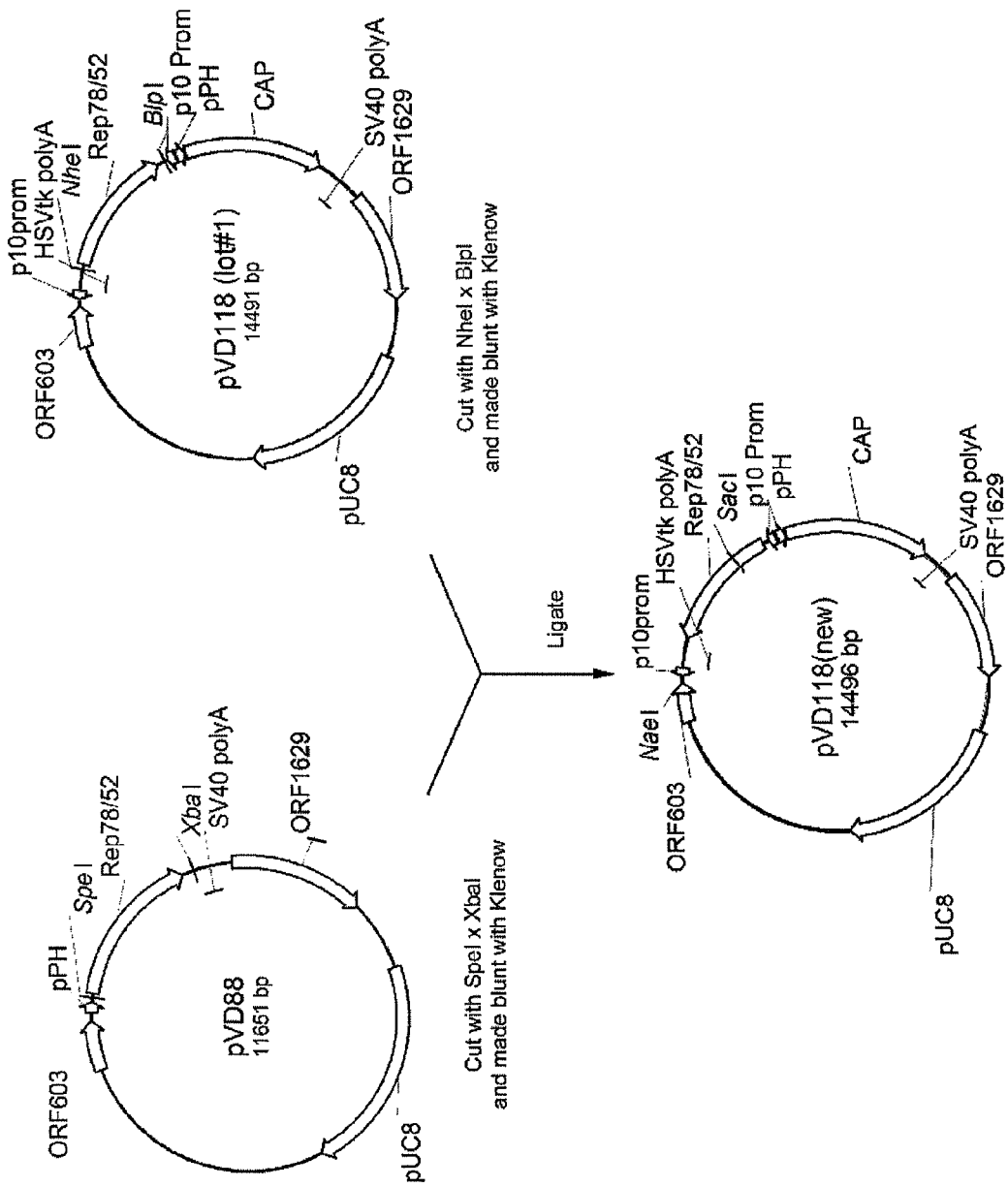
FIG. 1 shows a schematic representation of the construction of pVD118(new).

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked.

An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g., by the application of a chemical inducer. A "tissue specific" promoter is only active in specific types of tissues or cells.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g., Needleman Wunsch) which aligns the sequences optimally over the entire length, while sequences of substantially different lengths are preferably aligned using a local alignment algorithm (e.g., Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, *PNAS* 89:915-19). Sequence alignments and scores for percentage sequence identity may be determined using computer programs, such as the GCG Wisconsin Package, Version 10.3, available from Accelrys Inc., San Diego, Calif., USA, or using open source software, such as the program "needle" (using the global Needleman-Wunsch algorithm) or "water" (using the local Smith-Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith-Waterman algorithm, are preferred. Alternatively percentage similarity or identity may be determined by searching against public databases, using algorithms such as FASTA, BLAST, etc.

Nucleotide sequences encoding parvoviral Cap and/or Rep proteins of the invention may also be defined by their capability to hybridise with the nucleotide sequences of SEQ ID NO.'s: 20, 22, 24 and 1-4, respectively, under moderate, or preferably under stringent hybridisation conditions.

Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e., at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e., at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A "vector" is a nucleic acid molecule (typically DNA or RNA) that serves to transfer a passenger nucleic acid sequence (i.e., DNA or RNA) into a host cell. Three common types of vectors include plasmids, phages and viruses. Preferably, the vector is a virus. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A "viral vector" refers to a vector comprising some or all of the following: viral genes encoding a gene product, control sequences and viral packaging sequences.

A "parvoviral vector" is defined as a recombinantly produced parvovirus or parvoviral particle that comprises a polynucleotide to be delivered into a host cell, either in vivo, ex vivo or in vitro. Examples of parvoviral vectors include e.g., adeno-associated virus vectors. Herein, a parvoviral vector construct refers to the polynucleotide comprising the viral genome or part thereof, and a transgene.

The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, *Nucleic Acids Res* 15:1281-95; see, also, Jansen et al., 2003, *Nucleic Acids Res* 31:2242-51).

The term "reporter" (or reporter gene or protein) is mainly used to refer to nucleotide sequence encoding visible marker proteins, such as green fluorescent protein (GFP), eGFP, other fluorescent proteins, luciferase, secreted alkaline phosphatase (SEAP), GUS and the like, as well as nptII markers and the like.

DETAILED DESCRIPTION OF THE INVENTION

The present invention relates to the use of parvoviruses, in particular dependoviruses such as infectious human or simian AAV, and the components thereof (e.g., a parvovirus genome) for use as vectors for introduction and/or expression of nucleic acids in mammalian cells, preferably human cells. In particular, the invention relates to improvements in productivity of such parvoviral vectors when produced in insect cells.

Productivity in this context encompasses improvements in production titres and improvements in the quality of the resulting product, for example a product which has improved an total:full ratio (a measure of the number of particles which comprise nucleic acid). That is to say, the final product may have an increased proportion of filled particles, where filled implies that the particle comprises nucleic acid.

Viruses of the Parvoviridae family are small DNA viruses. The family Parvoviridae may be divided between two subfamilies: the Parvovirinae, which infect vertebrates, and the Densovirinae, which infect invertebrates, including insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in K. I. Berns, *Parvoviridae: The Viruses and Their Replication*, Chap. 69 in *Fields Virology* ($3^{rd}$ ed. 1996). For convenience, the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e., Rep78 and Rep52) are expressed from the P5 promoter and the P19 promoter, respectively and both Rep proteins have a function in the replication of the viral genome. A splicing event in the Rep ORF results in the expression of actually four Rep proteins (i.e., Rep78, Rep68, Rep52 and Rep40).

However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral or AAV vector" (or "rAAV vector") herein refers to a vector comprising one or more polynucleotide sequences of interest, genes of interest or "transgenes" that is/are flanked by at least one parvoviral or AAV inverted terminal repeat sequence (ITR). Preferably, the transgene(s) is/are flanked by ITRs, one on each side of the transgene(s). Such rAAV vectors can be replicated and packaged into infectious viral particles when present in an insect host cell that is expressing AAV rep and cap gene products (i.e., AAV Rep and Cap proteins). When an rAAV vector is incorporated into a larger nucleic acid construct (e.g., in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

The invention relates to a method for producing a recombinant parvoviral (rAAV) virion, comprising a recombinant parvoviral (rAAV) vector, in an insect cell.

In a first aspect, the invention relates to a method for the production of a recombinant parvoviral virion comprising the steps of: (a) providing an insect cell comprising one or more nucleic acid constructs comprising: (i) a nucleotide sequence comprising a transgene that is flanked by at least one parvoviral inverted terminal repeat nucleotide sequence; (ii) a first expression cassette comprising a nucleotide sequence encoding a parvoviral Rep protein which is operably linked to a first promoter that is capable of driving expression of the Rep protein in the insect cell; (iii) a second expression cassette comprising a nucleotide sequence encoding a parvoviral capsid protein which is operably linked to a second promoter that is capable of driving expression of the capsid protein in the insect cell; (b) culturing the cell defined in (a) under a condition conducive to the expression of the Rep and the capsid protein; and, (c) optionally recovery of the recombinant parvoviral virion. Preferably, in the insect cell, the first and second expression cassettes are present on a single nucleic acid construct.

Preferably, the first and second expression cassettes, when present in equimolar amount in an insect cell produce a ratio of levels of Rep protein encoding mRNA versus capsid protein encoding mRNA of at least about 0.5, at least about 0.75, at least about 1.0, at least about 1.5, at least about 2.0, at least about 5.0 or at least about 10.0. The levels of Rep and capsid encoding mRNAs are preferably determined by quantitative reverse-transcription PCR, Northern blot, or other means for RNA quantification know in the art.

Preferably, the ratio of the levels of Rep and capsid encoding mRNAs are produced in the insect cell at a time point from 24, 30, 36, 40, 44 or 46 hours after transfection to 72, 66, 60, 54, 52, or 50 hours after transfection. More preferably the ratio of the levels of Rep and capsid encoding mRNAs are at least produced in the insect cell 2 or 1 hour around 48 hours after transfection.

Alternatively preferred, the first and second expression cassettes, when present in equimolar amount in an insect cell produce a ratio of levels of Rep protein versus capsid protein of at least about 0.5, at least about 0.75, at least about 1.0, at least about 1.5, at least about 2.0, at least about 5.0 or at least about 10.0. The Rep and capsid protein levels are preferably determined using reference antibodies against the Rep and capsid proteins in a quantitative immunoassay (e.g., ELISA or quantitative Western-blot). Preferably, the ratio of the Rep and capsid protein levels are produced in the insect cell at a time point from 24, 30, 36, 40, 44 or 46 hours after transfection to 72, 66, 60, 54, 52, or 50 hours after transfection. More preferably the ratio of the Rep and capsid protein levels are produced in the insect cell 2 or 1 hour around 48 hours after transfection. Suitable reference antibodies for quantification of AAV Rep and capsid protein levels are e.g Anti-AAV-rep mouse monoclonal, clone 303.9, or anti-AAV VP1/VP2/VP3, mouse monoclonal, clone B1 obtainable from PROGEN Biotechnik GmbH.

In the method of the invention, the first and second expression cassettes are present on a single nucleic acid construct. One of the advantages of both expression cassettes being present on a single nucleic acid construct is that transfected insect cells will express both Rep protein and capsid protein. Only expression of both Rep protein and capsid protein in an insect cell will result in the formation of parvoviral virions. Another advantage is that the minimum required ratio of expression of the Rep protein versus the capsid protein can be controlled when the first and second expression cassettes are on one single construct.

It is an embodiment of the invention that another nucleic acid construct comprising a nucleotide sequence encoding a Rep protein may also be present in the cell.

In a method of the invention, the nucleotide sequence of the first expression cassette (ii) may preferably comprise only one open reading frame comprising nucleotide sequences encoding at least one of the Rep78 and Rep 68 proteins. That is to say, the Rep protein or proteins will be encoded by a single open reading frame, not by two or more open reading frames. To put it another way, the first expression cassette will typically not have two or more separate open reading frames encoding the same or different Rep proteins. For the avoidance of doubt, however, a single open reading frame may be capable of encoding more than one protein, for example two, three or four proteins.

All of the above may apply equally to the VP1, VP2 and VP3 proteins, i.e., two or all of those proteins may conveniently all be encoded by a single open reading frame.

Typically, in a method of the invention, at least one open reading frame comprising nucleotide sequences encoding the VP1, VP2 and VP3 capsid proteins or at least one open reading frame comprising an open reading frame comprising nucleotide sequences encoding at least one of the Rep78 and Rep68 proteins does not comprise an artificial intron (or a sequence derived from an artificial intron). That is to say, at least open reading frames used to encode Rep or VP proteins will not comprise an artificial intron. By artificial intron is meant an intron which would not naturally occur in an adeno-associated virus Rep or Cap sequence, for example an intron which has been engineered so as to permit functional splicing within an insect cell. An artificial intron in this context therefore encompass wild-type insect cell introns. An expression cassette of the invention may comprise native truncated intron sequence (by native is meant sequence naturally occurring in an adeno-associated virus)—such sequences are not intended to fall within the meaning of artificial intron as defined herein.

In the invention, one possibility is that no open reading frame comprising nucleotide sequences encoding the VP1, VP2 and VP3 capsid proteins and/or no open reading frame comprising nucleotide sequences encoding at least one of the Rep78 and Rep68 proteins comprises an artificial intron.

In a preferred embodiment of the invention, the nucleotide sequence comprising the transgene is also on same nucleic acid construct as first and second expression cassettes. An advantage thereof is, that all transfected cells comprise each of the three nucleotide sequences, that are needed for parvoviral virion production.

In addition, the present inventors found, that the higher the Rep protein:capsid protein ratio, the higher the full virion vs empty virion ratio is. The term "full virion" refers to a virion particle that comprises a parvoviral vector. The term "empty virion" refers to a virion particle that does not comprise a parvoviral vector. In a preferred embodiment of the invention, the full virion vs empty virion ratio is at least 1:100 more preferably at least 1:10 and even more preferably at least 1:1. Even more preferably, no empty virions can be detected and most preferably no empty virions are present. The person skilled in the art will know how to determine the full virion vs empty virion ratio, for example by dividing gene copy number by (total capsid−genome copy number), since per virion there will be only one genome copy present. Inversely, the higher the Rep protein:capsid protein ratio, the lower the ratio of empty virions vs. total virions (i.e., full+empty virions). The skilled artisan will know how to determine such ratio's. For example, the ratio of empty virions vs. total capsids may be determined by dividing the amount of genome copies (i.e., genome copy number) by the amount of total parvoviral particles (i.e., number of parvoviral particles), wherein the amount of genome copies per ml is measured by quantitative PCR and the amount of total parvoviral particles per ml is measured with an enzyme immunoassay, e.g., from Progen. In a preferred embodiment of the invention, the ratio of total virions to full virions is less than 100:1, more preferably less than 10:1. Even more preferably, no empty virions can be detected, and most preferably no empty virions are present.

In a preferred embodiment, the ratio of expression of the Rep versus the capsid protein is regulated by one or more of the following: (a) the first promoter is equally strong or stronger than the second promoter, as determined by reporter gene expression (eg luciferase or SEAP), or northern blot; (b) the presence of more and/or stronger enhancer elements in the first expression cassette as compared to the second expression cassette; (c) the nucleotide sequence coding for the parvoviral Rep protein has a higher codon adaptation index as compared to the nucleotide sequence coding for the capsid protein; (d) temperature optimization of the parvoviral Rep protein; and/or (e) variant Rep proteins with one or more alterations in the amino acid sequence as compared to a corresponding wild-type Rep protein and wherein the one or more amino acid alteration result in increases in the activity of the Rep function as assessed by detecting increased AAV production in insect cells. Methods for generation, selection and/or screening of variant Rep proteins with increased activity of Rep function as assessed by detecting increased AAV production in insect cells may be obtained by adaptation to insect cells of the methods described in US20030134351 for obtaining variant Rep proteins with increased function with respect to AAV production in mammalian cells. Variant Rep proteins with one or more alterations in the amino acid sequence as compared to a corresponding wild-type Rep protein are herein understood to include Rep proteins with one or more amino acid substitutions, insertions and/or deletions in the variant amino acid sequence as compared to the amino acid sequence of a corresponding wild type Rep protein.

The first promoter being equally strong or stronger than the second promoter means that in case of more nucleotide sequences encoding for a Rep protein than nucleotide sequences encoding for a capsid protein, an equally strong promoter may be used, since expression of Rep protein will then be increased as compared to expression of capsid protein, whereas in case of similar amounts of nucleotide sequences encoding for Rep and encoding for capsid protein, a stronger promoter may be used for expression Rep protein than for expression of capsid protein. The strength of the promoter may be determined by the expression that is obtained under conditions that are used in the method of the invention. In a preferred embodiment, the first promoter or the second promoter is selected from the group consisting of a PolH promoter, p10 promoter, basic protein promoter, an inducible promoter or a deltaIE1 promoter or an IE1 promoter, or any other late or very late baculovirus gene promoter. More preferably, the first promoter is selected from the group consisting of a PolH promoter, p10 promoter or basic protein promoter and wherein the second promoter is a deltaIE1 promoter or an IE1 promoter, or any other early or late baculovirus gene promoter. Preferably, the first promoter in the nucleic acid construct of the invention is a p10 promoter and the second promoter is a PolH promoter or a 4×Hsp27 EcRE+minimal Hsp70 promoter. In another embodiment, the first promoter in the nucleic acid construct of the invention is a 4×Hsp27 EcRE+minimal Hsp70 promoter and the second promoter is a PolH promoter. In yet another embodiment, the first promoter in the nucleic acid construct of the invention is a PolH promoter and the second promoter is a p10, a deltaIE1 or an IE1 promoter. In yet another embodiment, the first promoter in the nucleic acid construct of the invention is a PolH promoter and the second promoter is a deltaIE1 or an IE1 promoter. In yet another embodiment, the first promoter in the nucleic acid construct of the invention is a p10 promoter and the second promoter is a deltaIE1 or an IE1 promoter. In yet another embodiment, the first promoter in the nucleic acid construct of the invention is a PolH promoter and the second promoter is a PolH promoter. Most preferably, the first promoter in the nucleic acid construct op the invention is a PolH promoter and the second promoter is a deltaIE1 promoter.

An "enhancer element" or "enhancer" is meant to define a sequence which enhances the activity of a promoter (i.e., increases the rate of transcription of a sequence downstream of the promoter) which, as opposed to a promoter, does not possess promoter activity, and which can usually function irrespective of its location with respect to the promoter (i.e., upstream, or downstream of the promoter). Enhancer elements are well-known in the art. Non-limiting examples of enhancer elements (or parts thereof) which could be used in the present invention include baculovirus enhancers and enhancer elements found in insect cells. It is preferred that the enhancer element increases in a cell the mRNA expression of a gene, to which the promoter it is operably linked, by at least 25%, more preferably at least 50%, even more preferably at least 100%, and most preferably at least 200% as compared to the mRNA expression of the gene in the absence of the enhancer element. mRNA expression may be determined for example by quantitative RT-PCR.

Herein it is preferred to use an enhancer element to enhance the expression of parvoviral Rep protein. Thus, in a further preferred embodiment, the first expression cassette comprises at least one baculovirus enhancer element and/or at least one ecdysone responsive element. Preferably the enhancer element is selected from the group consisting of hr1, hr2, hr3, hr4 and hr5.

Codon optimization of the parvoviral Rep protein is discussed in more detail hereafter.

Temperature optimization of the parvoviral Rep protein refers to use the optimal condition with respect to both the temperature at which the insect cell will grow and Rep is functioning. A Rep protein may for example be optimally active at 37° C., whereas an insect cell may grow optimally at 28° C. A temperature at which both the Rep protein is active and the insect cell grows may be 30° C. In a preferred embodiment, the optimized temperature is more than 27, 28, 29, 30, 31, 32, 33, 34 or 35° C. and/or less than 37, 36, 35, 34, 33, 32, 31, 30 or 29° C.

As will be understood by the skilled person in the art, the full virion:empty virion ratio may also be improved by attenuated Cap expression, for example by means of a weaker promoter, as compared to moderate to high Rep expression.

Preferably a nucleic acid construct of the invention, is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e., the nucleic acid construct is a baculovirus-expression vector. Baculovirus-expression vectors and methods for their use are described for example in Summers and Smith. 1986. *A Manual of Methods for Baculovirus Vectors and Insect Culture Procedures*, Texas Agricultural Experimental Station Bull. No. 7555, College Station, Tex.; Luckow (1991) In Prokop et al., *Cloning and Expression of Heterologous Genes in Insect Cells with Baculovirus Vectors' Recombinant DNA Technology and Applications*, 97-152; King & Possee, 1992, supra; O'Reilly et al., 1992, supra; and Richardson, C D, 1995, *Baculovirus Expression Protocols, Methods in Molecular Biology*, vol. 39; U.S. Pat. No. 4,745,051; US2003/148506; and WO03/074714.

The number of nucleic acid constructs employed in the insect cell for the production of the recombinant parvoviral (rAAV) vector is not limiting in the invention. For example, one, two, three or more separate constructs can be employed to produce rAAV in insect cells in accordance with the methods of the present invention. If two constructs are employed, one construct may comprise the nucleotide sequence comprising the transgene that is flanked by at least one parvoviral ITR sequence and the other construct may then comprise a first and a second expression cassette. If three constructs are employed, one construct may comprise the nucleotide sequence comprising the transgene that is flanked by at least one parvoviral ITR sequence, another construct may comprise the first and second expression cassettes and still another construct may comprise an additional nucleotide sequence encoding for a Rep protein, optionally either codon optimized, AT-optimized or GC-optimized, in order to minimize or prevent recombination, as described hereinafter.

A nucleotide sequence encoding parvoviral Rep proteins, is herein understood as a nucleotide sequence encoding the non-structural Rep proteins that are required and sufficient for parvoviral vector production in insect cells such the Rep78 or Rep68, and/or the Rep52 or Rep40 proteins. The parvovirus nucleotide sequence preferably is from a dependovirus, more preferably from a human or simian adeno-associated virus (AAV) and most preferably from an AAV which normally infects humans (e.g., serotypes 1, 2, 3A, 3B, 4, 5, and 6) or primates (e.g., serotypes 1 and 4). An example of a nucleotide sequence encoding parvovirus Rep proteins is given in SEQ ID No 5, which depicts a part of the AAV serotype-2 sequence genome encoding the Rep proteins. The Rep78 coding sequence comprises nucleotides 11-1876 and the Rep52 coding sequence comprises nucleotides 683-1876, also depicted separately in SEQ ID NO:5 and 7. It is understood that the exact molecular weights of the Rep78 and Rep52 proteins, as well as the exact positions of the translation initiation codons may differ between different parvoviruses. However, the skilled person will know how to identify the corresponding position in nucleotide sequence from other parvoviruses than AAV-2.

In a preferred embodiment, the first expression cassette comprises a nucleotide sequence that encodes an amino acid sequence of a parvoviral Rep52 or 40 protein and/or a nucleotide sequence that encodes an amino acid sequence of a parvoviral Rep78 or 68 protein. Preferably, the parvoviral Rep proteins are adeno-associated virus (AAV) Rep proteins.

In a preferred embodiment, the invention relates to an insect cell that comprises no more than one type of nucleotide sequence comprising a single open reading frame encoding a parvoviral Rep protein. Preferably the single open reading frame encodes one or more of the parvoviral Rep proteins, more preferably the open reading frame encodes all of the parvoviral Rep proteins, most preferably the open reading frame encodes the full-length Rep 78 protein from which preferably at least both Rep 52 and Rep 78 proteins may be expressed in the insect cell. It is understood herein that the insect cell may comprise more than one copy of the single type of nucleotide sequence, e.g., in a multicopy episomal vector, but that these are multiple copies of essentially one and the same nucleic acid molecule, or at least nucleic acid molecules that encode one and the same Rep amino acid sequence, e.g., nucleic acid molecules that only differ between each other due to the degeneracy of the genetic code. The presence of only a single type of nucleic acid molecule encoding the parvoviral Rep proteins avoids recombination between homologous sequences as may be present in different types of vectors comprising Rep sequences, which may give rise to defective Rep expression constructs that affect (stability of) parvoviral production levels in insect cells.

In an alternative embodiment of the invention, the first expression cassette comprises more than one nucleotide sequence encoding a parvoviral Rep protein. It is preferred that the nucleotide sequence of (ii) comprises an open reading frame comprising nucleotide sequences encoding at least one of the Rep78 and Rep68 proteins. Preferably, the nucleotide sequences are of the same serotype. More preferably, the nucleotide sequences differ from each other in that they may be either codon optimized, AT-optimized or GC-optimized, to minimize or prevent recombination. Preferably, the first expression cassette comprises two nucleotide sequences encoding a parvoviral Rep protein, i.e., a first nucleotide sequence and a second nucleotide sequence. Preferably, the difference in the first and the second nucleotide sequence coding for the common amino acid sequences of a parvoviral Rep protein is maximised (i.e., the nucleotide identity is minimised) by one or more of: a) changing the codon bias of the first nucleotide sequence coding for the parvoviral Rep common amino acid sequence; b) changing the codon bias of the second nucleotide sequence coding for the parvoviral Rep common amino acid sequence; c) changing the GC-content of the first nucleotide sequence coding for the common amino acid sequence; and d) changing the GC-content of the second nucleotide sequence coding for the common amino acid sequence. Codon optimisation may be performed on the basis of the codon usage of the insect cell used in the method of the invention, preferably *Spodoptera frugiperda*, as may be found in a codon usage database (see e.g., World Wide Web URL kazusa.or.jp/codon/). Suitable computer programs for codon optimisation are available to the skilled person. (See e.g., Jayaraj et al., 2005, *Nucl. Acids Res.* 33:3011-16; and on the internet). Alternatively the optimisations can be done by hand, using the same codon usage database.

A nucleotide sequence of the first expression cassette encoding a parvoviral Rep52 protein may be defined as a nucleotide sequence:
(a) that encodes a polypeptide comprising an amino acid sequence that has at least 50, 60, 70, 80, 88, 89, 90, 95, 97, 98, or 99% sequence identity with the amino acid sequence of SEQ ID NO:6
(b) that has at least 50, 60, 70, 80, 81, 82, 85, 90, 95, 97, 98, or 99% sequence identity with the nucleotide sequence of any one of SEQ ID NO's:1-5;
(c) the complementary strand of which hybridises to a nucleic acid molecule sequence of (a) or (b);
(d) nucleotide sequences the sequence of which differs from the sequence of a nucleic acid molecule of (c) due to the degeneracy of the genetic code.

A nucleotide sequence of the first expression cassette encoding a parvoviral Rep78 protein may be defined as a nucleotide sequence:
(a) that encodes a polypeptide comprising an amino acid sequence that has at least 50, 60, 70, 80, 88, 89, 90, 95, 97, 98, or 99% sequence identity with the amino acid sequence of SEQ ID NO:8
(b) that has at least 50, 60, 70, 80, 81, 82, 85, 90, 95, 97, 98, or 99% sequence identity with the nucleotide sequence of positions 11-1876 of SEQ ID NO:7
(c) the complementary strand of which hybridises to a nucleic acid molecule sequence of (a) or (b);
(d) nucleotide sequences the sequence of which differs from the sequence of a nucleic acid molecule of (c) due to the degeneracy of the genetic code.

Preferably, the nucleotide sequence encodes parvovirus Rep proteins that are required and sufficient for parvoviral vector production in insect cells.

Elimination of possible false translation initiation sites in the Rep protein coding sequences, other than the Rep78 and Rep52 translation initiation sites, of other parvoviruses will be well understood by an artisan of skill in the art, as will be the elimination of putative splice sites that may be recognised in insect cells.

In a preferred embodiment, the initiation codon for translation of the parvoviral Rep78 protein is a suboptimal initiation codon. The suboptimal initiation codon preferably is an initiation codon that effects partial exon skipping. Partial exon skipping is herein understood to mean that at least part of the ribosomes do not initiate translation at the suboptimal initiation codon of the Rep78 protein but at an initiation codon further downstream, whereby preferably the initiation codon further downstream is the initiation codon of the Rep52 protein. The suboptimal initiation codon preferably effects partial exon skipping upon expression of the nucleotide sequence in an insect cell. Preferably, the suboptimal initiation codon effects partial exon skipping in an insect cell so as to produce in the insect cell a molar ratio of Rep78 to Rep52 in the range of 1:10 to 10:1, 1:5 to 5:1, or 1:3 to 3:1, preferably at about 20-40 hours post infection, more preferably at about 30-40 hours post infection, using a baculovirus expression. The molar ration of the Rep78 and Rep52 may be determined by means of Western blotting, preferably using a monoclonal antibody that recognizes a common epitope of both Rep78 and Rep52, or using e.g., a mouse anti-Rep antibody (303.9, Progen, Germany; dilution 1:50).

The term "suboptimal initiation codon" herein not only refers to the tri-nucleotide intitiation codon itself but also to its context. Thus, a suboptimal initiation codon may consist of an "optimal" ATG codon in a suboptimal context, e.g., a non-Kozak context. However, more preferred are suboptimal initiation codons wherein the tri-nucleotide intitiation codon itself is suboptimal, i.e., is not ATG. Suboptimal is herein understood to mean that the codon is less efficient in the inititiation of translation in an otherwise identical context as compared to the normal ATG codon. Preferably, the efficiency of suboptimal codon is less than 90, 80, 60, 40 or 20% of the efficiency of the normal ATG codon in an otherwise identical context. Methods for comparing the relative efficiency of inititiation of translation are known per se to the skilled person. Preferred suboptimal initiation codons may be selected from ACG, TTG, CTG, and GTG. More preferred is ACG. A nucleotide sequence encoding parvovirus Rep proteins, is herein understood as a nucleotide sequence encoding the non-structural Rep proteins that are required and sufficient for parvoviral vector production in insect cells such the Rep78 and Rep52 proteins.

It is also possible to replace other ATG's in the sequence with a different codon encoding methionine so that the in less possibility of initiating translation from such ATG's.

Various modifications of the coding nucleotide sequence as defined above, including e.g., the wild-type parvoviral sequences, for proper expression in insect cells is achieved by application of well-known genetic engineering techniques such as described e.g., in Sambrook and Russell (2001) *Molecular Cloning: A Laboratory Manual* (3rd edition), Cold Spring Harbor Laboratory, Cold Spring Harbor Laboratory Press, New York. Various further modifications of coding regions are known to the skilled artisan which could increase yield of the encode proteins. These modifications are within the scope of the present invention.

A nucleotide sequence encoding a parvoviral capsid (Cap) protein is herein understood to comprise nucleotide sequences encoding one or more of the three parvoviral capsid proteins, VP1, -2 and -3. The parvovirus nucleotide sequence preferably is from a dependovirus, more preferably from a human or simian adeno-associated virus (AAV) and most preferably from an AAV which normally infects humans (e.g., serotypes 1, 2, 3A, 3B, 4, 5, and 6) or primates (e.g., serotypes 1 and 4). Examples of a nucleotide sequence encoding parvovirus capsid proteins is given in SEQ ID No 20, 22 and 24.

In a preferred embodiment the nucleotide sequence of (iii) comprises an open reading frame comprising nucleotide sequences encoding the VP1, VP2 and VP3 capsid proteins. The capsid protein coding sequences may be present in various forms. E.g. separate coding sequences for each of the capsid proteins VP1, -2 and -3 may used, whereby each coding sequence is operably linked to expression control sequences for expression in an insect cell. More preferably, however, the second expression cassette comprises a nucleotide sequence comprising a single open reading frame encoding all three of the parvoviral (AAV) VP1, VP2, and VP3 capsid proteins, wherein the initiation codon for translation of the VP1 capsid protein is a suboptimal initiation codon that is not ATG as e.g., described by Urabe et al. (2002, supra) and in WO2007/046703. A suboptimal initiation codon for the VP1 capsid protein may be as defined above for the Rep78 protein. More preferred suboptimal initiation codons for the VP1 capsid protein may be selected from ACG, TTG, CTG and GTG, of which CTG and GTG are most preferred. The nucleotide sequence comprised in the second expression cassette for expression of the capsid proteins may further comprise one or more modifications as described in WO2007/046703. Various further modifications of VP coding regions are known to the skilled artisan which could either increase yield of VP and virion or have other desired effects, such as altered tropism or reduce antigenicity of the virion. These modifications are within the scope of the present invention.

In a preferred embodiment, the expression of VP1 is increased as compared to the expression of VP2 and VP3. VP1 expression may be increased by supplementation of VP1, by introduction into the insect cell of a single vector comprising nucleotide sequences for the VP1 as has been described in WO 2007/084773.

In the context of the invention "at least one parvoviral inverted terminal repeat nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans acting replication proteins such as e.g., Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a recombinant parvoviral (rAAV) vector that is unable to further propagate after initial introduction into a cell in the presence of a second AAV. Such a safety mechanism for limiting undesirable vector propagation in a recipient may be provided by using rAAV with a chimeric ITR as described in US2003148506.

The term "flanked" with respect to a sequence that is flanked by another element(s) herein indicates the presence of one or more of the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence that is "flanked" by two other elements (e.g., ITRs), indicates that one element is located 5' to the sequence and the other is located 3' to the sequence; however, there may be intervening sequences therebetween. In a preferred embodiment a nucleotide sequence of (i) is flanked on either side by parvoviral inverted terminal repeat nucleotide sequences.

In the embodiments of the invention, the nucleotide sequence comprising the transgene (encoding a gene product of interest) that is flanked by at least one parvoviral ITR sequence preferably becomes incorporated into the genome of a recombinant parvoviral (rAAV) vector produced in the insect cell. Preferably, the transgene encodes a gene product of interest for expression in a mammalian cell. Preferably, the nucleotide sequence comprising the transgene is flanked by two parvoviral (AAV) ITR nucleotide sequences and wherein the transgene is located in between the two parvoviral (AAV) ITR nucleotide sequences. Preferably, the nucleotide sequence encoding a gene product of interest (for expression in the mammalian cell) will be incorporated into the recombinant parvoviral (rAAV) vector produced in the insect cell if it is located between two regular ITRs, or is located on either side of an ITR engineered with two D regions.

AAV sequences that may be used in the present invention for the production of a recombinant AAV virion in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g., GenBank Accession numbers U89790, J01901; AF043303, and AF085716; Chiorini et al. (1997, *J. Virol.* 71:6823-33); Srivastava et al. (1983, *J. Virol.* 45:555-64); Chiorini et al. (1999, *J. Virol.* 73:1309-19); Rutledge et al. (1998, *J. Virol.* 72:309-19); and Wu et al. (2000, *J. Virol.* 74: 8635-47). AAV serotypes 1, 2, 3, 4 and 5 are preferred source of AAV nucleotide sequences for use in the context of the present invention. Preferably the AAV ITR sequences for use in the context of the present invention are derived from AAV1, AAV2, and/or AAV4. Likewise, the Rep (Rep78/68 and Rep52/40) coding sequences are preferably derived from AAV1, AAV2, and/or AAV4. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g., capsid shuffling techniques and AAV capsid libraries, or from newly designed, developed or evolved ITR's.

AAV Rep and ITR sequences are particularly conserved among most serotypes. The Rep78 proteins of various AAV serotypes are e.g., more than 89% identical and the total nucleotide sequence identity at the genome level between AAV2, AAV3A, AAV3B, and AAV6 is around 82% (Bantel-Schaal et al., 1999, *J. Viral.,* 73):939-47). Moreover, the Rep sequences and ITRs of many AAV serotypes are known to efficiently cross-complement (i.e., functionally substitute) corresponding sequences from other serotypes in production of AAV particles in mammalian cells. US2003/148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped rAAV particles comprising the capsid proteins of a serotype (e.g., AAV3) and the Rep and/or ITR sequences of another AAV serotype (e.g., AAV2). Such pseudotyped rAAV particles are a part of the present invention.

Modified "AAV" sequences also can be used in the context of the present invention, e.g., for the production of rAAV vectors in insect cells. Such modified sequences e.g., include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e., a nucleotide sequence comprises an AAV5 Rep78). Such ITR and Rep sequences can be modified as desired to obtain efficient production of rAAV5 or pseudotyped rAAV5 vectors in insect cells. E.g., the start codon of the Rep sequences can be modified, VP splice sites can be modified or eliminated, and/or the VP1 start codon and nearby nucleotides can be modified to improve the production of rAAV5 vectors in the insect cell.

The nucleotide sequence comprising the transgene as defined herein above may thus comprise a nucleotide sequence encoding at least one "gene product of interest" for expression in a mammalian cell, located such that it will be incorporated into an recombinant parvoviral (rAAV) vector replicated in the insect cell. In the context of the invention it is understood that a particularly preferred mammalian cell in which the "gene product of interest" is to be expressed, is a human cell. Any nucleotide sequence can be incorporated for later expression in a mammalian cell transfected with the recombinant parvoviral (rAAV) vector produced in accordance with the present invention. The nucleotide sequence may e.g., encode a protein it may express an RNAi agent, i.e., an RNA molecule that is capable of RNA interference such as e.g., a shRNA (short hairpinRNA) or an siRNA (short interfering RNA). "siRNA" means a small interfering RNA that is a short-length double-stranded RNA that are not toxic in mammalian cells (Elbashir et al., 2001, *Nature* 411:494-98; Caplen et al., 2001, *Proc. Natl. Acad. Sci. USA* 98:9742-47). In a preferred embodiment, the nucleotide sequence comprising the transgene may comprise two coding nucleotide sequences, each encoding one gene product of interest for expression in a mammalian cell. Each of the two nucleotide sequences encoding a product of interest is located such that it will be incorporated into a recombinant parvoviral (rAAV) vector replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g., ablation of an undesired activity, e.g., the ablation of an infected cell, or the complementation of a genetic defect, e.g., causing a deficiency in an enzymatic activity. Examples of therapeutic polypeptide gene products include CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), and cytokines or interleukins like, e.g., IL-10, porphobilinogen deaminase (PBGD), a neurotrophic factor such as glial cell line-derived neurotrophic factor (GDNF) and alanine:glyoxylate aminotransferase (AGT).

Alternatively, or in addition as another gene product, the nucleotide sequence comprising the transgene as defined herein above may further comprise a nucleotide sequence encoding a polypeptide that serves as a marker protein to assess cell transformation and expression. Suitable marker proteins for this purpose are e.g., the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel, supra. Furthermore, the nucleotide sequence comprising the transgene as defined herein above may comprise a further nucleotide sequence encoding a polypeptide that may serve as a fail-safe mechanism that allows to cure a subject from cells transduced with the recombinant parvoviral (rAAV) vector of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g., the *E. coli* cytosine deaminase gene or one of the thymidine kinase genes from herpes simplex virus, cytomegalovirus and varicella-zoster virus, in which case ganciclovir may be used as prodrug to kill the transgenic cells in the subject. (See, e.g., Clair et al., 1987, *Antimicrob. Agents Chemother.* 31: 844-49).

In another embodiment one of the gene products of interest can be an AAV protein. In particular, a Rep protein, such as Rep78 or Rep68, or a functional fragment thereof. A nucleotide sequence encoding a Rep78 and/or a Rep68, if present on the genome of a recombinant parvoviral (rAAV) vector of the invention and expressed in a mammalian cell transduced with the vector, allows for integration of the recombinant parvoviral (rAAV) vector into the genome of the transduced mammalian cell. Expression of Rep78 and/or Rep68 in an rAAV-transduced or infected mammalian cell can provide an advantage for certain uses of the recombinant parvoviral (rAAV) vector, by allowing long term or permanent expression of any other gene product of interest introduced in the cell by the vector.

In the recombinant parvoviral (rAAV) vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art. See: Sambrook and Russel, 2001, supra. Constitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an α1-anti-trypsin (AAT) promoter, a thyroid hormone-binding globulin promoter, an albumin promoter, a LPS (thyroxine-binding globlin) promoter, an HCR-ApoCII hybrid promoter, an HCR-hAAT hybrid promoter, an AAT promoter combined with the mouse albumin gene enhancer (Ealb) element and an apolipoprotein E promoter. Other examples include the E2F promoter for tumour-selective, and, in particular, neurological cell tumour-selective expression (Parr et al., 1997, *Nat. Med.* 3:1145-49) or the IL-2 promoter for use in mononuclear blood cells (Hagenbaugh et al., 1997, *J Exp Med;* 185:2101-10).

AAV is able to infect a number of mammalian cells. See, e.g., Tratschin et al. (1985, *Mol. Cell. Biol.* 5:3251-60) and Grimm et al. (1999, *Hum. Gene Ther.* 10:2445-50). However, AAV transduction of human synovial fibroblasts is significantly more efficient than in similar murine cells, Jennings et al., *Arthritis Res,* 3:1 (2001), and the cellular tropicity of AAV differs among serotypes. See, e.g., Davidson et al. (2000, *Proc. Natl. Acad. Sci. USA,* 97:3428-32), who discuss differences among AAV2, AAV4, and AAV5 with respect to mammalian CNS cell tropism and transduction efficiency. In a preferred embodiment, a host cell of the invention is any mammalian cell that may be infected by a parvoviral virion, for example, but not limited to, a muscle cell, a liver cell, a nerve cell, a glial cell and an epithelial cell. In a preferred embodiment a host cell of the invention is a human cell.

Preferably, in the construct, the nucleotide sequence encoding a parvoviral Rep protein and/or a parvoviral capsid protein is operably linked to expression control sequences for expression in an insect cell. These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. supra; Luckow. 1991, supra; King & Possee, 1992, supra; O'Reilly et al., 1992, supra; Richardson, 1995, supra; U.S. Pat. No. 4,745, 051; US2003/148506; and WO03/074714. Suitable promoters for transcription of the nucleotide sequences comprised in the first and the second construct of the invention include e.g., the polyhedron (PolH), p10, p35, IE-1 or ΔIE-1 promoters and further promoters described in the above references.

The nucleic acid construct comprising at least the first and/or second expression cassettes, may further comprise an expression control sequence that comprises a nine nucleotide sequence of SEQ. ID NO:9 or a nucleotide sequence substantially homologous to SEQ. ID NO:9, upstream of the initiation codon of the nucleotide sequence encoding the parvoviral Rep protein and/or of the initiation codon of the nucleotide sequence encoding the parvoviral VP1 capsid protein. A sequence with substantial identity to the nucleotide sequence of SEQ. ID NO:9 and that will help increase expression of the parvoviral Rep protein is e.g., a sequence which has at least 60%, 70%, 80% or 90% identity to the nine nucleotide sequence of SEQ ID NO:9.

The insect cell may be any cell that is suitable for the production of heterologous proteins. Preferably the insect cell allows for replication of baculoviral vectors and can be maintained in culture. More preferably the insect cell also allows for replication of recombinant parvoviral vectors, including rAAV vectors. For example, the cell line used can be from *Spodoptera frugiperda, Drosophila* cell lines, or mosquito cell lines, e.g., *Aedes albopictus* derived cell lines. Preferred insect cells or cell lines are cells from the insect species which are susceptible to baculovirus infection, including, e.g., S2 (CRL-1963, ATCC), Se301, SeIZD2109, SeUCR1, SD, Sf900+, Sf21, BTI-TN-5B1-4, MG-1, Tn368, HzAm1, Ha2302, Hz2E5, High Five (Invitrogen, CA, USA) and ExpresSF+® (U.S. Pat. No. 6,103,526; Protein Sciences Corp., CT, USA). A preferred insect cell according to the invention is an insect cell for production of recombinant parvoviral vectors.

The one or more nucleic acid constructs of the method of the invention may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

Growing conditions for insect cells in culture, and production of heterologous products in insect cells in culture are well-known in the art and described e.g., in the above cited references on molecular engineering of insects cells. (See also WO2007/046703.)

In a preferred embodiment of the method of the invention, the recombinant parvoviral virion is recovered. Recovery preferably comprises the step of affinity-purification of the (virions comprising the) recombinant parvoviral (rAAV) vector using an anti-AAV antibody, preferably an immobilised antibody. The anti-AAV antibody preferably is an monoclonal antibody. A particularly suitable antibody is a single chain camelid antibody or a fragment thereof as e.g., obtainable from camels or llamas (see e.g., Muyldermans, 2001, Biotechnol. 74:277-302). The antibody for affinity-purification of rAAV preferably is an antibody that specifically binds an epitope on a AAV capsid protein, whereby, preferably, the epitope is an epitope that is present on capsid protein of more than one AAV serotype. For example, the antibody may be raised or selected on the basis of specific binding to AAV2 capsid but at the same time also it may also specifically bind to AAV1, AAV3 and AAV5 capsids.

In a second aspect, the invention relates to a nucleic acid construct comprising one or more expression cassettes of the invention as herein defined above. In a preferred embodiment, the nucleic acid construct of the invention comprises a first and a second expression cassette of the invention and optionally a nucleic acid sequence of (i). Preferably, the first promoter in the nucleic acid construct of the invention is a p10 promoter and the second promoter is a PolH promoter or a 4×Hsp27 EcRE+minimal Hsp70 promoter. More preferably, the first promoter is operably linked with an enhancer, preferably an HR1 enhancer. In another embodiment, the first promoter in the nucleic acid construct of the invention is a 4×Hsp27 EcRE+minimal Hsp70 promoter and the second promoter is a PolH promoter. In yet another embodiment, the first promoter in the nucleic acid construct of the invention is a PolH promoter and the second promoter is a p10, a deltaIE1 or an IE1 promoter. In yet another embodiment, the first promoter in the nucleic acid construct of the invention is a PolH promoter and the second promoter is a deltaIE1 or an IE1 promoter. In yet another embodiment, the first promoter in the nucleic acid construct of the invention is a p10 promoter and the second promoter is a deltaE1 or an IE1 promoter. In yet another embodiment, the first promoter in the nucleic acid construct of the invention is a PolH promoter and the second promoter is a PolH promoter. In further embodiments, any other combination of the first promoter and the second promoter are part of the invention. The first promoter may be selected from the group consisting of a PolH promoter, p10 promoter, basic protein promoter, an inducible promoter or a deltaIE1 promoter or an IE1 promoter, or any other late or very late baculovirus gene promoter. The second promoter may be selected from the group consisting of a PolH promoter, p10 promoter, basic protein promoter, an inducible promoter or a deltaIE1 promoter or an IE1 promoter, or any other late or very late baculovirus gene promoter. More preferably, the first promoter is selected from the group consisting of a PolH promoter, p10 promoter or basic protein promoter and wherein the second promoter is a deltaIE1 promoter or an IE1 promoter, or any other early or late baculovirus gene promoter.

In a preferred embodiment the first expression cassette comprised in the nucleic acid construct of the invention, comprises an enhancer element as defined above.

In a third aspect, the invention relates to an insect cell as defined above.

In a fourth aspect, the invention relates to a kit comprising (a) a nucleic acid construct comprising the first and second expression cassette as defined above; and (b) a nucleic acid construct comprising a nucleotide sequence encoding a multiple cloning site for a transgene that is flanked by at least one parvoviral inverted terminal repeat nucleotide sequence, which transgene is operably linked to a promoter capable of driving expression of the transgene in a host cell.

In a preferred embodiment, the nucleic acid construct (b) comprises a nucleotide sequence encoding a transgene that is flanked by at least one parvoviral inverted terminal repeat nucleotide sequence, which transgene is operably linked to a promoter capable of driving expression of the transgene in a host cell.

The kit may further comprise insect cells and a nucleic acid sequence encoding baculovirus helper functions for expression in the insect cell.

In a further aspect the invention relates to a batch of parvoviral virions produced in the above described methods of the invention. A "batch of parvoviral virions" is herein defined as all parvoviral virions that are produced in the same round of production, optionally per container of insect cells. In a preferred embodiment, the batch of parvoviral virions of the invention comprises a full virion:total virion ratio as described above and/or a full virion:empty ratio as described above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The following Examples illustrate the invention:

EXAMPLES

Example 1

Figure 2:
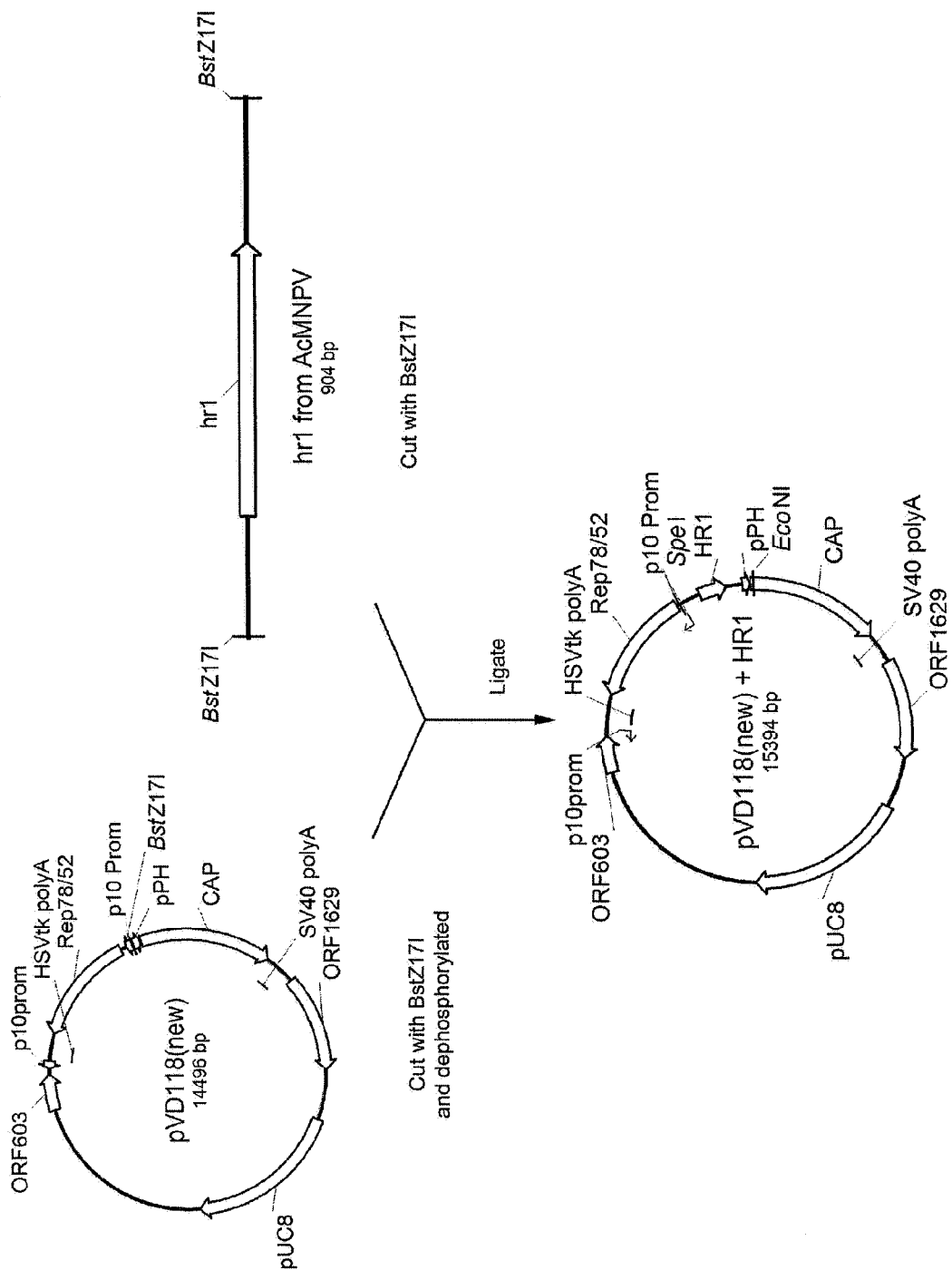
FIG. 2 shows a schematic representation of the construction of pVD118(new)+HR1.

1.1 Materials and Methods 1.1.1 Generation of Recombinant Baculovirus
The following constructs were generated:
1.1.1.1 Construction of pVD118 (New)
pVD118 (new) is a control vector comprising an expression cassette comprising the nucleotide sequence of Rep78 under the control of the p10 promoter and an expression cassette comprising the nucleotide sequence of Cap genes under the control of the polyhedron (PolH or pPH) promoter. pVD118 (new) was constructed as shown in FIG. 1. Before the final plasmid pVD118 (new) could be made the predecessors pFastBac Dual Rep78/ACG and pVD118 (lot#1) was constructed. In brief, plasmid REP-ACG/PSC (patent application WO2007148971; herein also referred to as pVD88) pVD88 was digested with SpeI* XbaI and 5' overhangs were made blunt. The 2057 bp fragment was isolated from an agarose gel, purified and ligated into the with SmaI linearized pFastBac Dual (Invitrogen), resulting in pFastBac Dual Rep78/ACG. Thereafter, this plasmid was digested with BstZ17I and SnaBI and the 2537 bp p10_Rep78/ACG fragment was isolated and ligated into the BstZ17I linearized pVD84, generating pVD118 (lot#1). However, the orientation of the Rep78/ACG expression cassette was incorrect and therefore deleted by performing a digestion with NheI*BlpI. After blunting the 5' overhangs the 12431 bp vector fragment was isolated and purified from gel. Subsequently, the 2057 bp purified fragment from REP-ACG/PSC was ligated into the vector and the transformation mix was transformed to chemically competent TOP10 cells (Invitrogen) and plated onto ampicilin containing plates. Restriction analysis with NaeI*SacI was performed on DNA isolated from miniprep cultures. Correct clones give fragments with a size of 2204 bp and 12292 bp.
1.1.1.2 Construction of pVD118 (New)+HR1
pVD118 (new)+HR1 is the same as pVD118, with the addition of an hr1 enhancer that is located in between the p10 and polyhedron promoter and was constructed as shown in FIG. 2. Briefly, a PCR performed on AcMNPV viral DNA (Protein Sciences Corporation, Meriden, USA) with primers HR1-Fw 5'-gtatacgtatgacact atcgatgttgac-3' (SEQ ID NO:10) and HR1-Rv 5'-gtatacgatcgattattgctccaatactag-3' (SEQ ID NO:11) resulted in a product of 904 bp that is cloned to the pCRII-blunt-TOPO vector (Invitrogen). After digestion with BstZ17I the 898 bp fragment was isolated from gel, purified and ligated into the pVD118(new) vector that was cut open with BstZ17I and dephosphorylated. Control digestions of correct clones with SpeI*EcoNI resulted in fragments of 1269 bp and 14125 bp.

Figure 3:
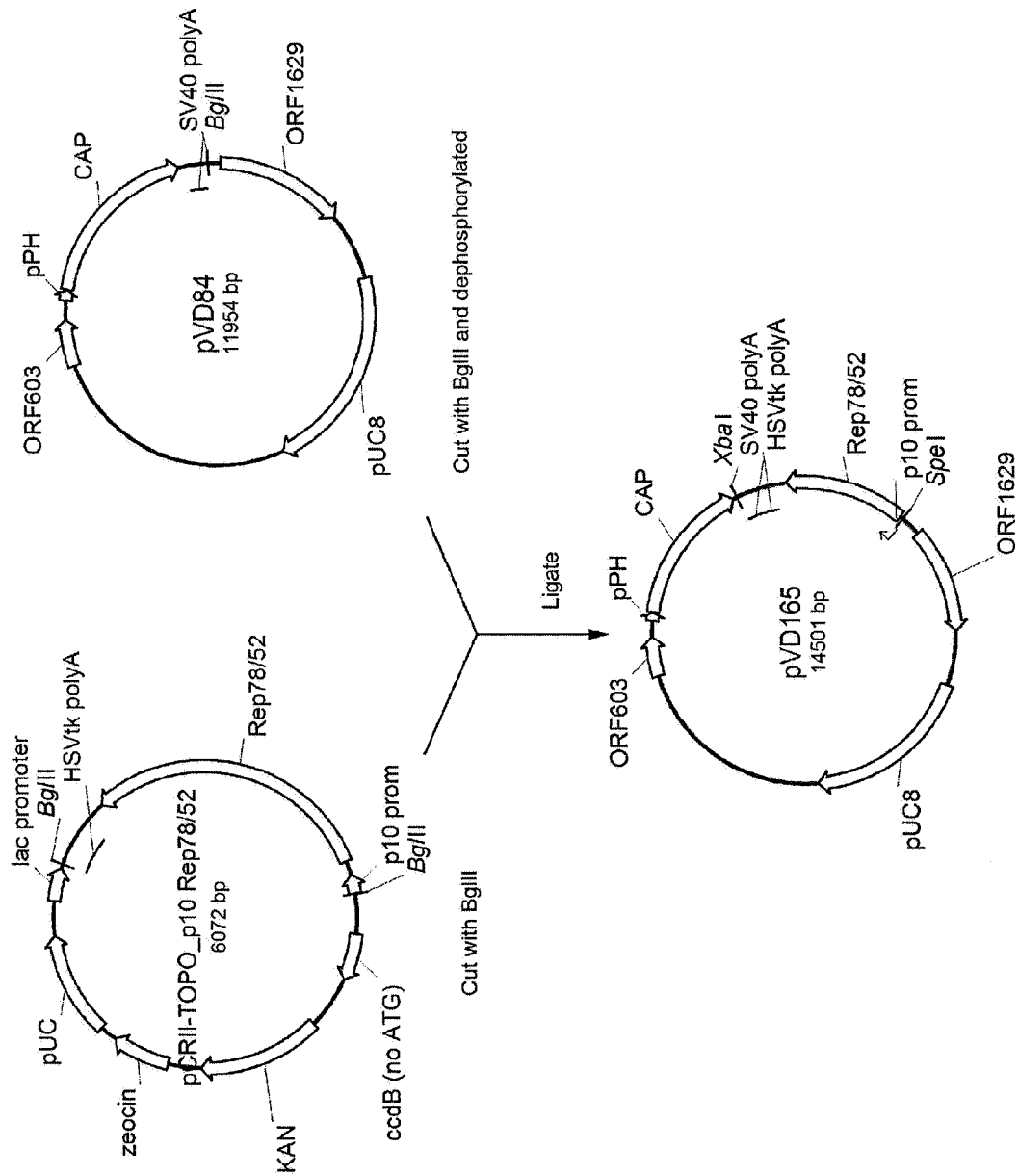
FIG. 3 shows a schematic representation of the construction of pVD165.

1.1.1.3 Construction of pVD84 (+p10 Rep) (=pVD165)

pVD165 is a control vector comprising an expression cassette comprising the nucleotide sequence of Rep78 wherein the start codon has been mutated into ACG under the control of the p10 promoter and an expression cassette comprising the nucleotide sequence of Cap genes under the control of the PolH promoter. The expression cassettes are in opposite direction in the plasmid. pVD165 was constructed as shown in FIG. 3. Briefly, a PCR performed on pVD118 (new) with primers polyA Fw 5'-agatctgtagtggctatggcagggc-3' (SEQ ID NO:12) and p10 Rv 5'-agatctcccgggacggacctttaattcaacccaac-3' (SEQ ID NO:13) resulted in a product of 2566 bp that was cloned to the pCRII-blunt-TOPO vector (Invitrogen). After digestion with BglII the 2541 bp fragment was isolated from gel, purified and ligated into the pVD84 vector that was cut open with BglII and dephosphorylated. Control digestions of correct clones with SpeI*XbaI resulted in fragments of 1269 bp and 11810 bp.

Figure 4:
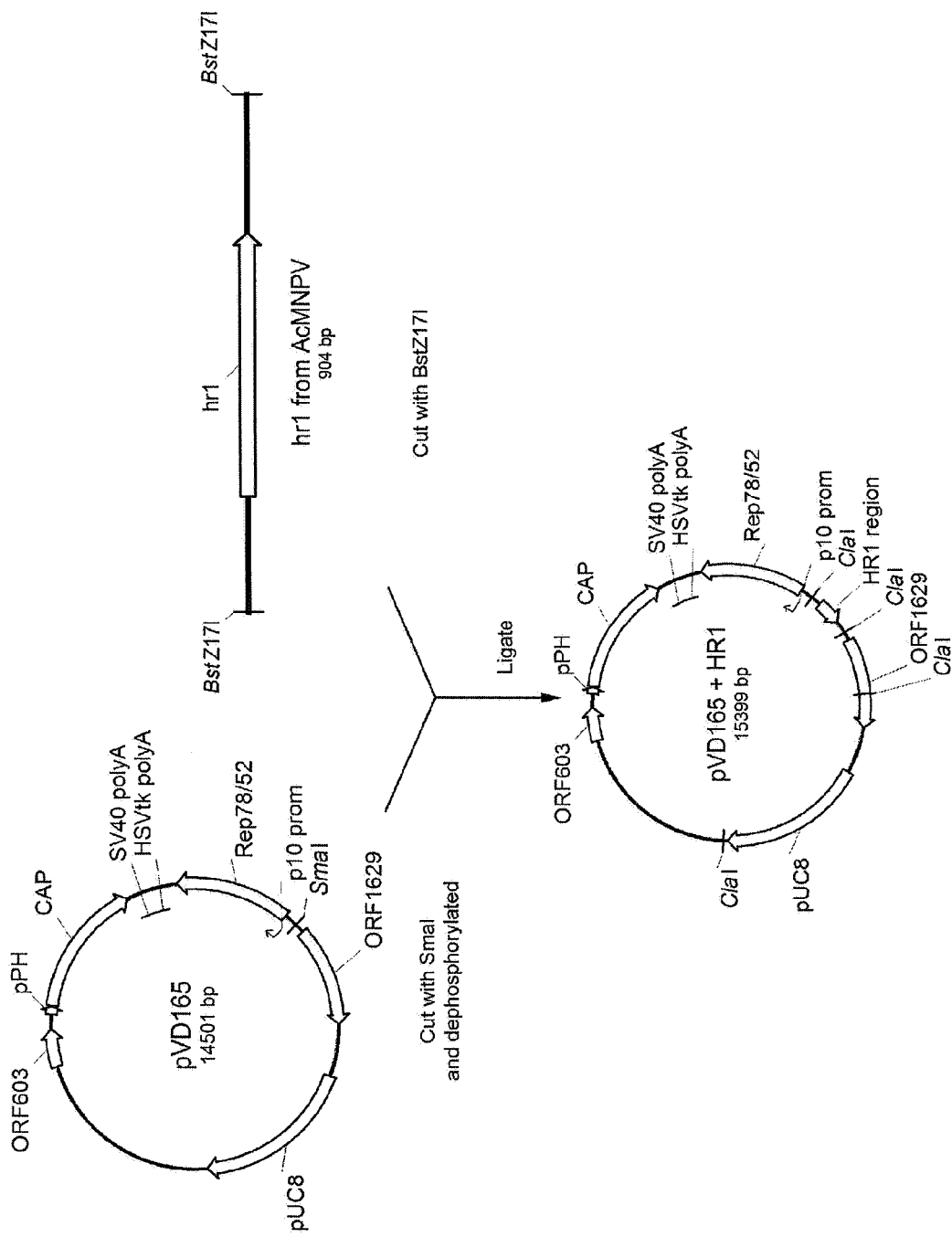
FIG. 4 shows a schematic representation of the construction of pVD165+HR1.

1.1.1.4 Construction of pVD165+HR1 pVD165+HR1 is the same as pVD165, with the addition of an hr1 enhancer donwtream of the p10 promoter and was constructed as shown in FIG. 4. Briefly, a PCR performed on AcMNPV viral DNA with primers HR1-Fw 5'-gtatacgtatgacactatcgatgttgac-3' (SEQ ID NO:10) and HR1-Rv 5'-gtatacgatcgattattgctccaatactag-3' (SEQ ID NO:11) resulted in a product of 904 bp that was cloned to the pCRII-blunt-TOPO vector (Invitrogen). After digestion with BstZ17I the 898 bp fragment was isolated from gel, purified and ligated into the pVD165 vector that was cut open with SmaI and dephosphorylated. Control digestions of correct clones with ClaI resulted in fragments of 875 bp, 1184 bp, 4160 bp and 9180 bp.

Figure 5:
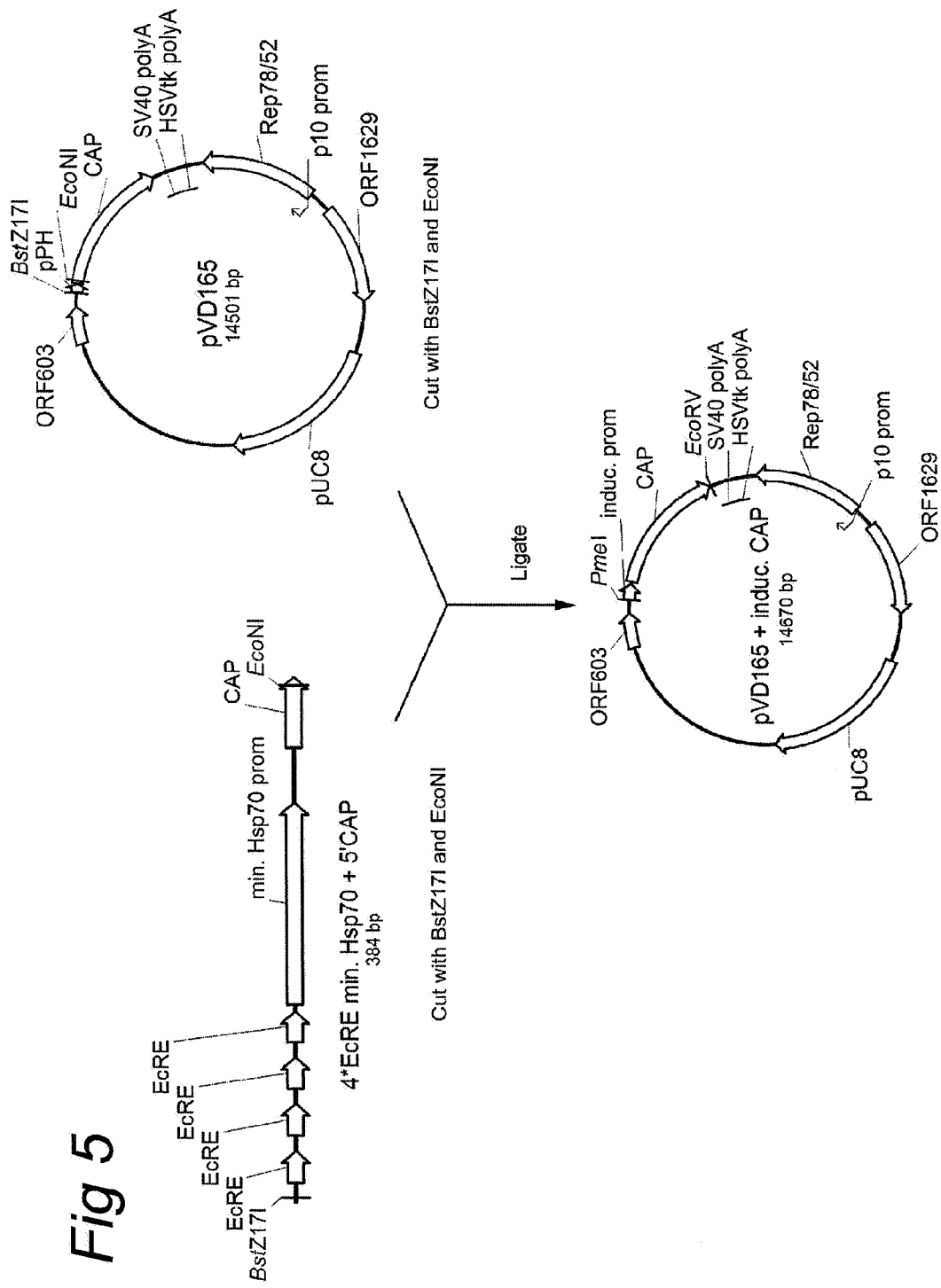
FIG. 5 shows a schematic representation of the construction of pVD165+4×EcRE CAP.

1.1.1.5 Construction of pVD165 with Inducible Promoter Upstream of CAP (pVD165+4×EcRE CAP)

pVD165+4×EcRE CAP is similar to pVD165, but comprises an inducible promoter instead of the polyhedron (pPH) promoter. pVD165+4×EcRE CAP was constructed as shown in FIG. 5. Briefly, the inducible promoter, which comprises 4 consecutive EcRE, a minimal hsp70 promoter (Poels et al. *Insect Biochem Mol Biol* 2004, 34:451-58) and part of the CAP coding sequence, was synthesized and ligated into pCRII-blunt-TOPO (Invitrogen). After digestion with BstZ17I and EcoNI the 375 bp fragment was isolated from gel, purified and ligated into the pVD165 vector that was cut open with BstZ17I and EcoNI. Control digestions of correct clones with PmeI*EcoRV resulted in fragments of 2554 bp and 12116 bp.

Figure 6:
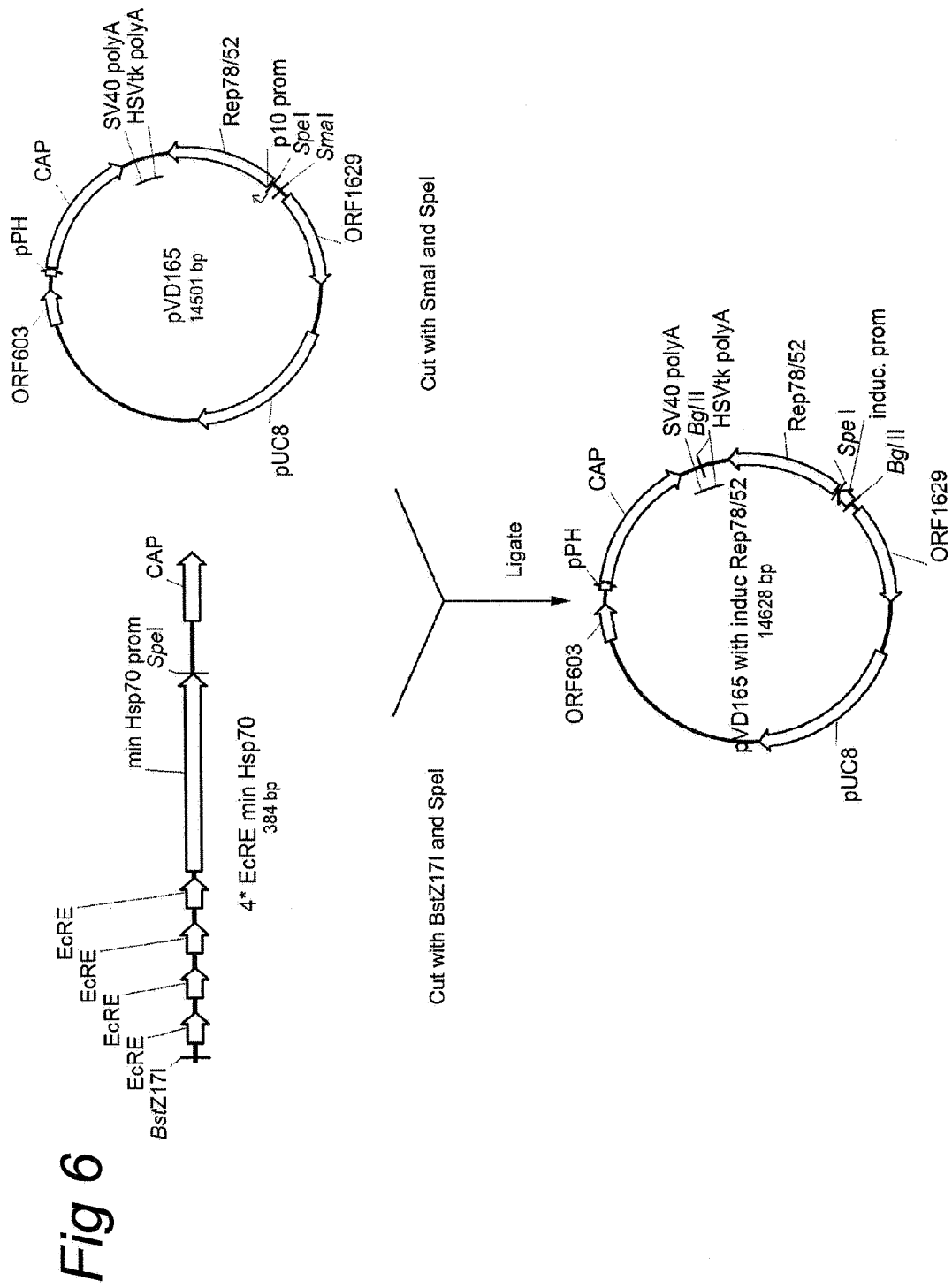
FIG. 6 shows a schematic representation of the construction of pVD165+4*EcRE Rep78.

1.1.1.6 Construction of pVD165 with Inducible Promoter Upstream of Rep (pVD165+4*EcRE Rep78-52)

pVD165+4*EcRE Rep78 is similar to pVD165, but comprises an inducible promoter instead of the p10 promoter. pVD165+4*EcRE Rep78 was constructed as shown in FIG. 6. Briefly, the inducible promoter which consist out of 4 consecutive EcRE and a minimal hsp70 promoter was synthesized and ligated into pCRII-blunt-TOPO (Invitrogen). After digestion with BstZ17I and SpeI the 290 bp fragment was isolated from gel, purified and ligated into the pVD165 vector that was cut open with SmaI and SpeI. Control digestions of correct clones with SpeI*BglII resulted in fragments of 298 bp, 2376 bp and 11954 bp.

1.1.1.7 Construction of pVD190 Construct (deltaIE1 Cap+ pPolh Rep)

Figure 7:
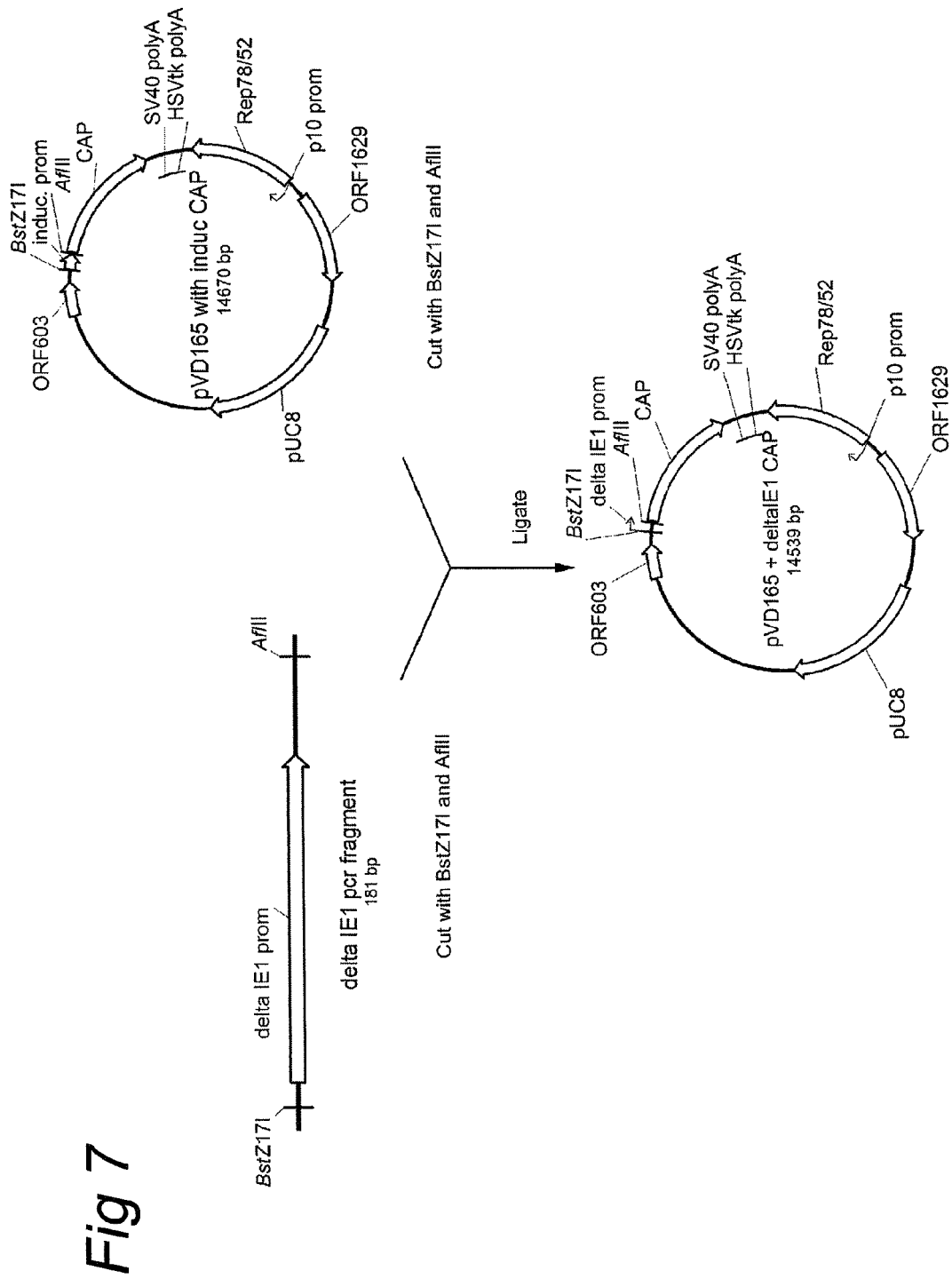
FIG. 7 shows a schematic representation of the construction of pVD165+deltaIE1 CAP.
Figure 8:
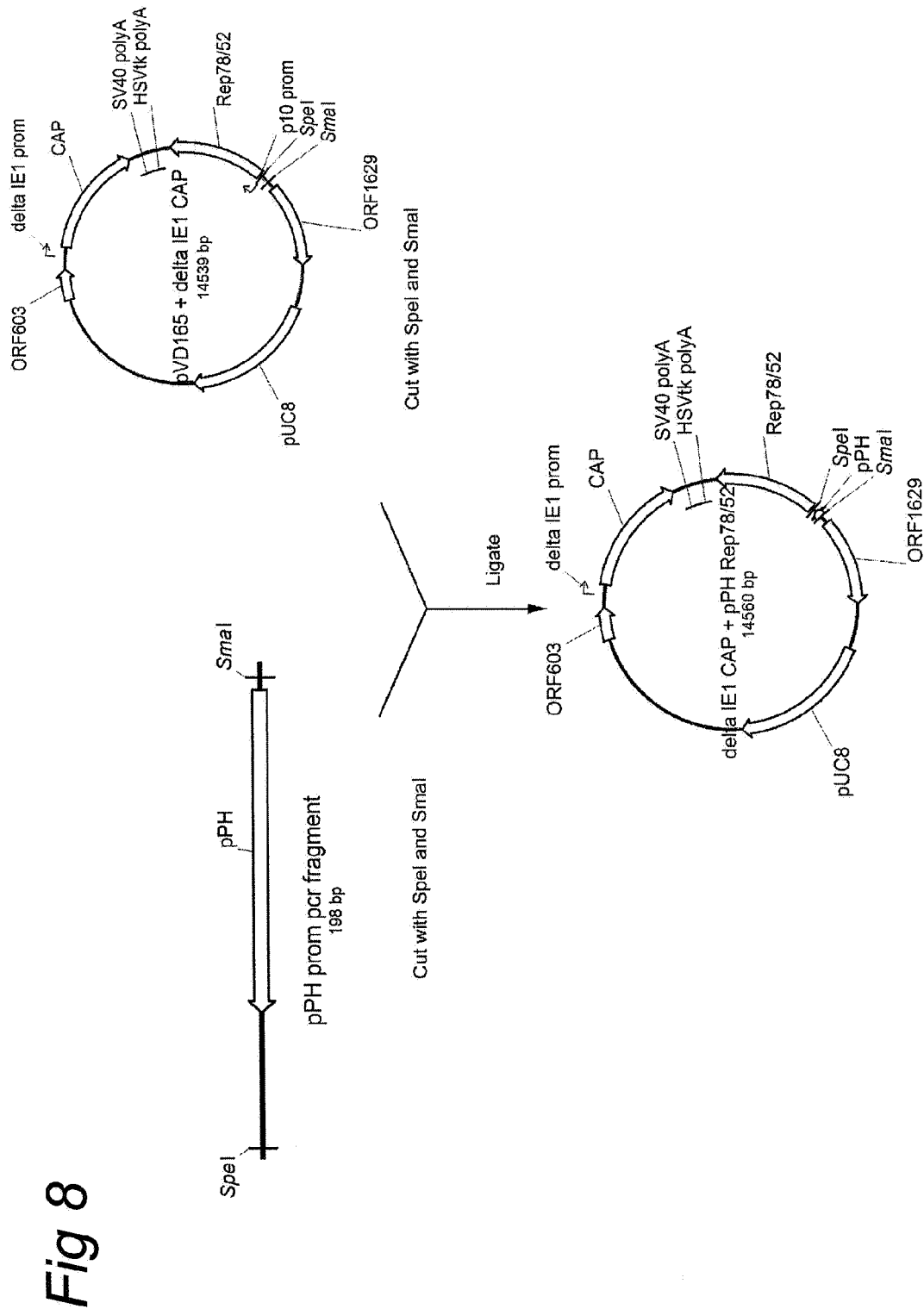
FIG. 8 shows a schematic representation of the construction of deltaIE1 Cap+pPolh Rep (pVD190).

DeltaIE1 Cap+pPolh Rep is similar to pVD165, but comprises a delta IE1 promoter instead of the pPH promoter and a pPolH promoter instead of the p10 promoter. DeltaIE1 Cap+pPolh Rep was constructed as shown in FIGS. 7 and 8. Hereto, a precursor vector was constructed in the following way. A PCR performed on pFBDSLR (Urabe et al. 2002 (supra) with primers BstZ17I-deltaIE1 Fw: 5'-ggtcc gtatacgacgataacgccgttggtggcg-3' (SEQ ID NO:14) and AflII-delta IE1 Rv: 5'-cgacttaagacggcgaattctgcagatggc-3' (SEQ ID NO:15) resulted in a product of 181 bp that was cloned to the pCRII-blunt-TOPO vector (Invitrogen). After digestion with BstZ17I*AflII the 165 bp fragment was isolated from gel, purified and ligated into the pVD165+4×EcRE CAP vector that was cut open with BstZ17I and AflII. The resulting plasmid is pVD165+deltaIE1 CAP and control digestion with BstZ17I*AflII should result in 165 bp and 14374 bp fragments. Subsequently, the polyhedrin promoter was cloned in front of the Rep expression cassette in pVD165+deltaIE1 CAP. Hereto, a PCR with primers SmaI-pPolh Fw: 5'-tct cccgggagatcatggagataattaaaatgataac-3' (SEQ ID NO:16) and SpeI-pPolh Rv: 5'-gttactagtgagctcgtcgac-3' (SEQ ID NO:17) was performed on pVD88. This generated a PCR product of 198 bp that was cloned to the pCRII-blunt-TOPO vector (Invitrogen). After digestion with SpeI*SmaI the 188 bp fragment was isolated from gel, purified and ligated into the pVD165+deltaIE1_Cap vector that was cut open with SpeI and SmaI. Finally, this resulted in the pVD165+deltaIE1 CAP construct.

1.1.1.8 Construction of p10-Cap-pPolh-Rep Construct

Figure 9:
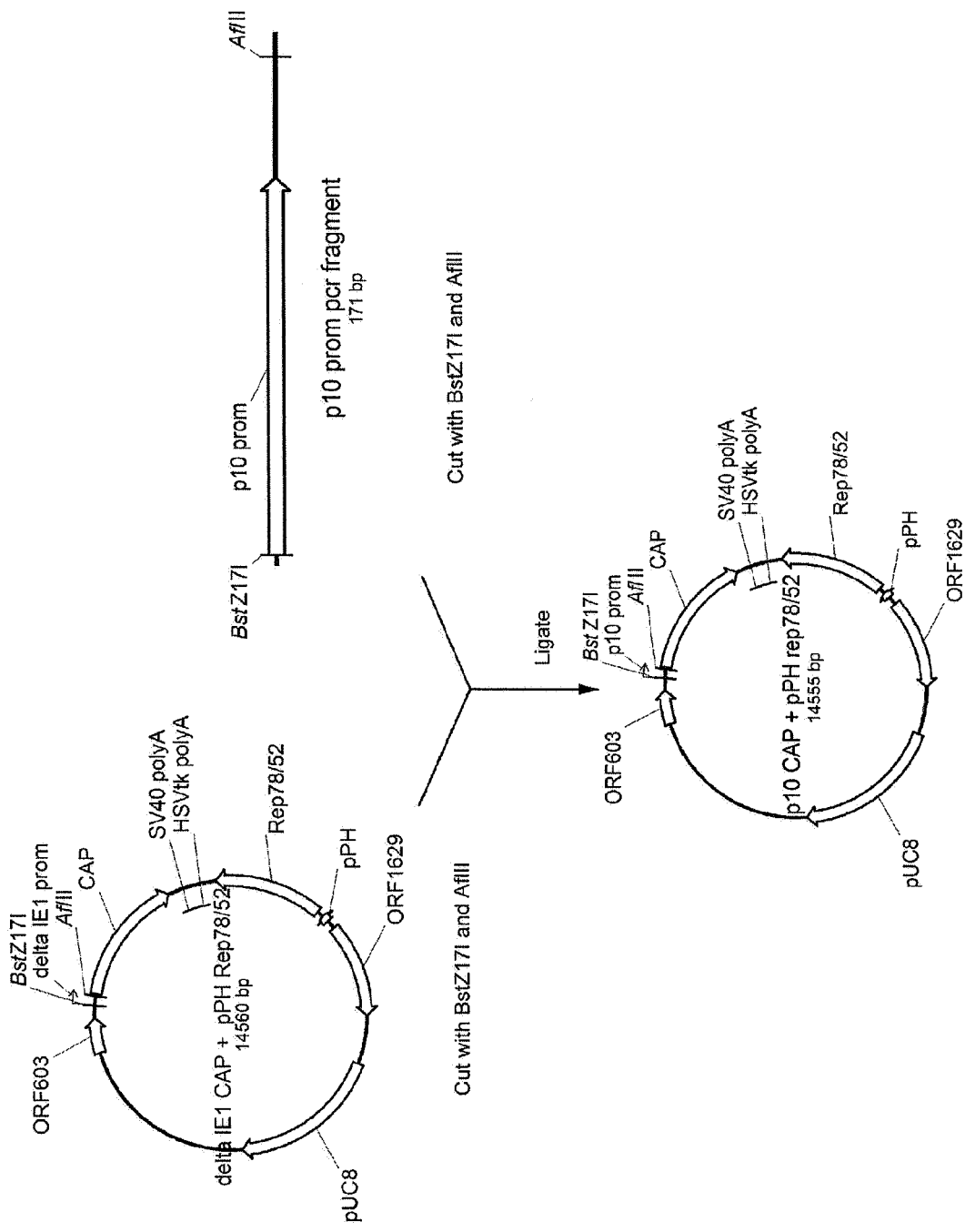
FIG. 9 shows a schematic representation of the construction of p10 Cap+pPolh Rep.

The p10_Cap+pPolh_Rep construct is similar to the delta-IE1-Cap-pPolh-Rep construct, but comprises a p10 promoter instead of the delta-IE1 promoter in front of the Cap expression cassette and was constructed as shown in FIG. 9. A PCR performed on pFastBac Dual with primers BstZ17I-p10 Fw: 5'-agtatacggaccttttaattcaac-3' (SEQ ID NO:18) and AflII-p10 Rv: 5'-cgacttaagagcgggccgctttcgaatc-3' (SEQ ID NO:19) resulted in a product of 171 bp that was cloned to the pCRII-blunt-TOPO vector (Invitrogen). After digestion with BstZ17I*AflII the 160 bp fragment was isolated from gel, purified and ligated into the delta-IE1-Cap-pPolh-Rep construct that was cut open with BstZ17I and AflII.

1.1.1.9 Construction of pVD194 (Rep78/CTG(Delta ATGs))

Figure 10:
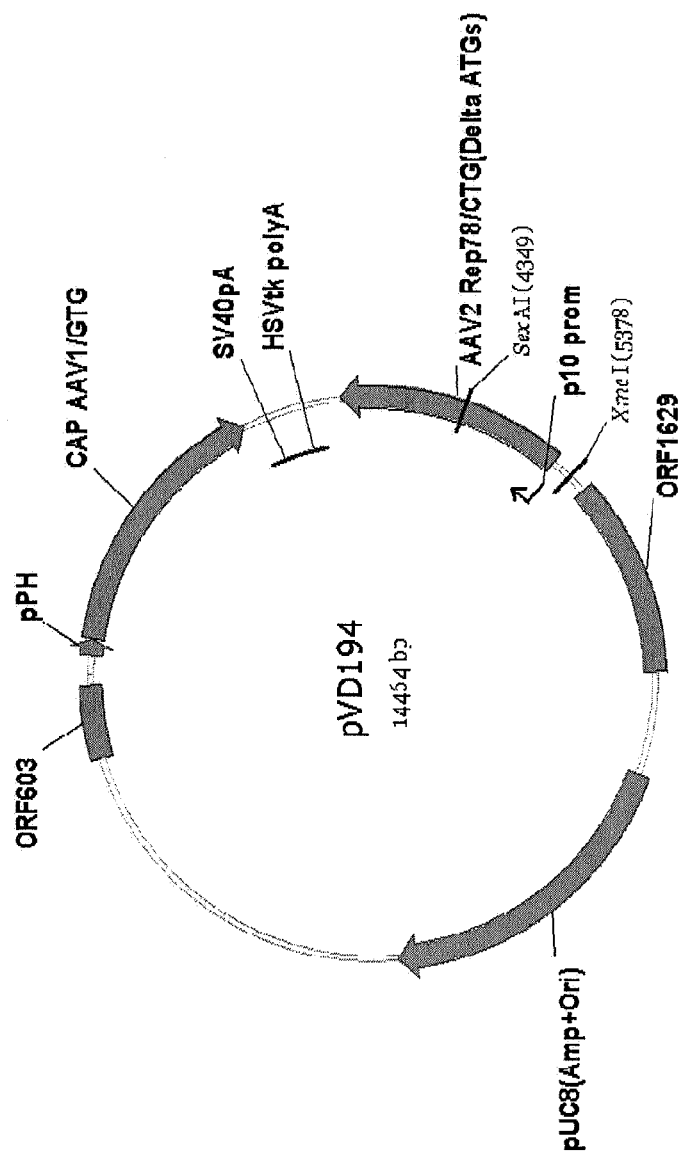
FIG. 10 shows a schematic representation of the construction of pVD194.

A rep plasmid with a CTG start codon without any internal ATG sites was first constructed by synthesizing the necessary gene according to the sequence set out in SEQ ID NO:31. The rep gene was then deleted from plasmid pVD88 using restriction enzymes RsrII and XbaI. The synthesized gene was then ligated in plasmid pVD88 using restriction sites RsrII and XbaI to give pVD195. pVD195 was then digested with BglII, resulting in 9297 bp and 2231 bp fragments. The 5' overhangs were then filled with Klenow and then digested with SexAI. This results in 9297 bp, 1372 and 859 bp fragments. The 859 bp fragment was then isolated. The necessary vector was generated by digesting pVD165 with SpeI to give a 14501 bp linear fragment. The 5' overhangs were filled with Klenow and then digested with SexAI to yield 13600 bp and 901 bp fragments. The 13600 bp fragment was isolated. The 859 bp BglII(Klenow)*SexAI fragment was then ligated into pVD165 (SpeI(Klenow)*SexAI) to yield pVD194 (see FIG. 10). A control digestion with SexAI*XmaI should result in fragments of 13435 bp and 1029 bp.

1.1.1.10 Construction of pVD84

To convert the start site of the baculovirus expression vector pFBAAV1VPm11 (Urabe et al., 2002, supra) from ACG to GTG, a PCR was performed using the following primers: The forward primer sequence contains a BamHI site (AMT primer #169; SEQ ID NO:29)

5'-TTA<u>GGATCC</u>TGTTAAGGTGGCTGCCGACGG-3'

The reverse primer sequence contains a StuI site (AMT primer #158; SEQ ID NO:30)

5'-GTCGT<u>AGGCCT</u>TGTCGTGCTCGAGGGCCGC-3'

| startsite | Primer forward | Primer reverse | AMT plasmid# (Bac-toBac) | AMTplasmid# (PSC) |
|---|---|---|---|---|
| GTG | 169 | 158 | pVD63 | pVD84 |

The PCR using primers #169 and #158 was performed and the PCR product (250 bp) was purified using the PCR Purification Kit (Qiagen Lot#11879372) and cut with restriction enzymes BamHI and StuI. The baculovirus expression vector was also digested with BamHI and StuI. Following dephosphorylation of the vector with SAP (Promega Lot#17501504), both insert (Cap with GTG startsite) and vector were purified on gel. After ligation of vector and insert, they were transformed into chemically competent DH5α cells (Invitrogen Lot#1241753) and streaked onto LB plates containing ampicillin. The DNA of pVD63 (Cap/GTG start site) was purified and examined for identity using sequence analysis by BaseClear and restriction.

To clone the Cap gene with the GTG startsite in the baculovirus expression vector pPSC10 (Protein Sciences) it was cut out of pVD63 with SmaI and AvrII and ligated into the dephosphorylated expression vector which was cut open with EcoRV and XbaI. Subsequently, the ligation mixture was transformed into chemically competent DH10β cells (invitrogen lot#1268527) and streaked onto LB-ampicillin plates. After miniprep DNA isolation using the QIAprep Spin miniprep kit (Qiagen lot #12180218) one miniprep (clone #13) was selected by restriction analysis with SphI. With this clone DNA (pVD84) was purified with the SNAP midiprep kit (Invitrogen solution Lot#1256921 and column Lot#1259367). The identity of pVD84 was checked by sequence analysis around the startcodon performed by BaseClear and by restriction analysis with BamHI and SphI (SEQ ID NO:28).

1.1.1.11 Recombinant Baculovirus Production

Recombinant Bac.VD118(new), Bac.VD118(new)+HR1, Bac.VD165, Bac.VD165+HR1, Bac.VD165+4×EcRE CAP, Bac.VD165+4*EcRE Rep78, Bac.VD190 and Bac.VD194 (p0) were generated with the Protein sciences system (Protein Sciences Corporation, Meriden, USA). Recombinant baculovirus was amplified by diluting them 1:100 into $2\times10^6$ SF$^+$ cells per ml. Three days after infection the cells were spun down and the supernatant containing the virus recovered. Amplifying of next passages was performed in same manner.

1.1.2 rAAV production rAAV batches were produced according to Urabe et al., 2002 (supra), but with the exception that two recombinant baculoviruses were used instead of three. One baculovirus harboured an expression construct under the control of the CMV promoter and is flanked by AAV ITRs. The other baculovirus is the Rep-Cap baculovirus that harboured two expression cassettes, one for the AAV replication gene and one for the for the AAV capsid. Expression of the replication or capsid gene under control of the inducible promoter was regulated by addition of 0.001-1 uM Ponasterone A to the culture medium. The different rAAV1 production experiments were performed with baculovirus stocks Bac.VD43 p5 containing the LPL transgene under control of the CMV promoter and different passages (p3, p4 or p5) of the Rep/Cap baculoviruses. In each experiment the standard rAAV1 production (Bac.VD88:Bac.VD84:Bac.VD43 with ratio 5:1:1) was taken along as a control.

1.1.3 Full/Total AAV Particle Determination

To determine the ratio of full versus total capsids, the amount of genome copies (gc) is divided by the amount of total AAV particles. The amount of gc/ml was measured by Q-PCR assay and the amount of total AAV particles was determined with an enzyme immunoassay of Progen (see below). For the Q-PCR reaction SYBR Green PCR Master Mix (Applied Biosystems, #4309155) was used according to the instructions of the producer (25 µl total volume; PCR-program: 10 min 95° C., 40 cycles of 15 sec 95° C. and 1 min 60° C.) using one of the following primer sets:

| pr59 | AATGGGCGGTAGGCGTGTA | CMV | SEQ ID NO: 26 |
| pr60 | AGGCGATCTGACGGTTCACTAA | CMV | SEQ ID NO: 27 |

The ratio is compared to the ratio obtained under standard production conditions, using a 5:1:1 volume ratio of Bac.Rep, Bac.Cap and Bac.ITR.

1.1.4 Western Blot Analysis

Three days after rAAV production cells were lysed by adding 0.1V 10×TRIS lysis buffer (1.5M NaCl, 0.5M TRIS, 0.01M MgCl, 1% TRITON X-100, pH8.5, filter sterilised) and incubated on ice for 30 minutes. Free DNA and RNA was degraded by incubation with benzonase at 37° C. for 15 minutes. Cell lysate was centrifuged (1,900×g; 15 min; 4° C.). NuPAGE LDS sample buffer (4×, Invitrogen) was added to a sample of the supernatant and was loaded onto a 4-12% Bis-Tris gel (120V). Proteins were blotted onto a PVDF membrane (BioRad) for 30 minutes, 10V (Semidry blotting). Western immunochemistry was performed by blocking the membrane with Superblock-PBS blocking buffer (PIERCE) and subsequent incubation with mouse anti-Rep (303.9, Progen, Germany; dilution 1:50) and rabbit anti-mouse—HRP (DAKO, dilution 1:500). The Rep-proteins were visualized by chemoluminescent staining with lumi-light plus Western-blotting substrate (Roche).

1.1.5 Total rAAV1 Particle ELISA

The total amount of rAAV1 particles (tp) made in each production was determined with the AAV1 Titration ELISA kit (Progen, Heidelberg, Germany) and performed according to the protocol supplied by the manufacturer, but with the exception that all samples and controls were pre-diluted in crude lysate bulk (CLB). Briefly, the CLB was made by harvesting of expressSF+ cells after three days by adding 10× lysis buffer and incubation for 1 h at 28° C. After treatment with benzonase for 1 h at 37° C., the lysate was centrifuged at 1900 g and supernatant was stored at 4° C. To determine the total rAAV1 particles in the crude lysate of each production the samples were 50-fold pre-diluted in CLB, this is the start dilution. Thereafter extra dilutions of 250, 1250 and 6250-fold were made in the CLB. The standard line was also diluted in the CLB. Samples from production with Bac.VD190 were only a 50 and 100-fold diluted, because of the low expression levels of the capsid proteins.

1.1.6 Total Particle Analysis Using HPLC

Unknown AAV-1 stocks are injected into the HPLC-system, resulting in a peak in the chromatogram. This peak can be integrated by Chemstation-software and represents the amount of total particles injected. A concentrated AAV-1 stock was titrated for its amount of total particles per milliliter by Electron Microscopy, and set into the method. Using this standard as a calibrator, the amount of total particles of the unknown can be calculated. In addition, when injecting a particular amount of genomic copies (which approximately represents the amount of full-particles) within the range of the standard, the ratio full- and empty particles can be estimated.

1.2 Results

Full:Empty AAV Particle Ratio Improves Upon Use of Two Baculovirus System, in Particular with High Rep Protein Expression and Moderate Cap Protein Expression Three constructs were investigated in detail: pVD165, pVD190 and pVD194.

To determine the total/full ratio for rAAV1 particles produced with Bac.VD165 the total particle concentration in the crude lysates was determined in two independent experiments. The results of these ELISAs and the corresponding total/full ratios are shown in Table 1.

TABLE 1

Total/full ratio of rAAV1 produced with the baculovirus stock Bac.VD165. The total particle concentration was determined with the total AAV1 particle ELISA. The full particle concentration was determined by Q-PCR. Total/full ratios can only be compared to the control produced in the same experiment.

|  | Bac.VD165: Bac.VD43 | Total particle concentration (tp/ml) | Full particle concentration (gc/ml) | Total/full ratio (tp/gc) |
|---|---|---|---|---|
| #1 | control | 7.07E+12 | 2.05E+10 | 345 |
|  | 1:1 | 4.91E+11 | 2.24E+09 | 219 |
|  | 5:1 | 8.3E+11 | 5.0E+09 | 166 |
| #2 | control | 3.19E+13 | 1.99E+10 | 1603 |
|  | 1:1 | 6.32E+11 | 6.33E+08 | 998 |
|  | 5:1 | 1.30E+12 | 1.10E+09 | 1182 |

The total/full ratio for the 1:1 productions is in both experiments 1.6 times improved as compared to the control. For the 5:1 production the total/full ratio is 2.1 and 1.4 times better as compared to the control. In conclusion, total/full ratio is improved for the rAAV1 particles produced with Bac.VD165.

In Bac.VD190, the Cap expression cassette is under control of the weak ΔIE1 promoter.

This may result in a lower capsid expression than in the productions performed with the other Rep/Cap baculoviruses or in the control situation, because in all those conditions the Cap expression is induced by the strong polyhedrin promoter. To test this hypothesis from two different experiments performed with Bac.VD190 the total particle concentration was determined. Results are shown in Table 2.

TABLE 2

Total/full ratio of rAAV1 produced with the baculovirus stock Bac.VD190. The total particle concentration was determined with the total AAV1 particle ELISA. The full particle concentration was determined by Q-PCR. Total/full ratios can only be compared to the control produced in the same experiment

|  | Bac.VD190: Bac.VD43 | Total particle concentration (tp/ml) | Full particle concentration (gc/ml) | Total/full ratio (tp/gc) |
|---|---|---|---|---|
| #1 | control | 3.19E+13 | 1.99E+10 | 1603 |
|  | 1:1 | 8.6E+10 | 5.97E+09 | 14 |
|  | 5:1 | 3.62E+11 | 1.8E+09 | 201 |
| #2 | control | 6.11E+12 | 4.03E+10 | 152 |
|  | 1:1 | 3.75E+11 | 1.74E+09 | 216 |
|  | 5:1 | 3.44E+11 | 3.12E+09 | 110 |

Results from production #1 (Table 2) show that the total/full ratios obtained by the 1:1 and 5:1 productions were 114 and 8 times improved as compared to the control, respectively. In production #2, the total/full ratio is 1.4 times lower or 1.4 times higher for the 1:1 or 5:1 production. In conclusion, total/full ratio appears to also be improved for the rAAV1 particles produced with Bac.VD190 (as was observed for Bac.VD165).

Figures 11A, 11B:
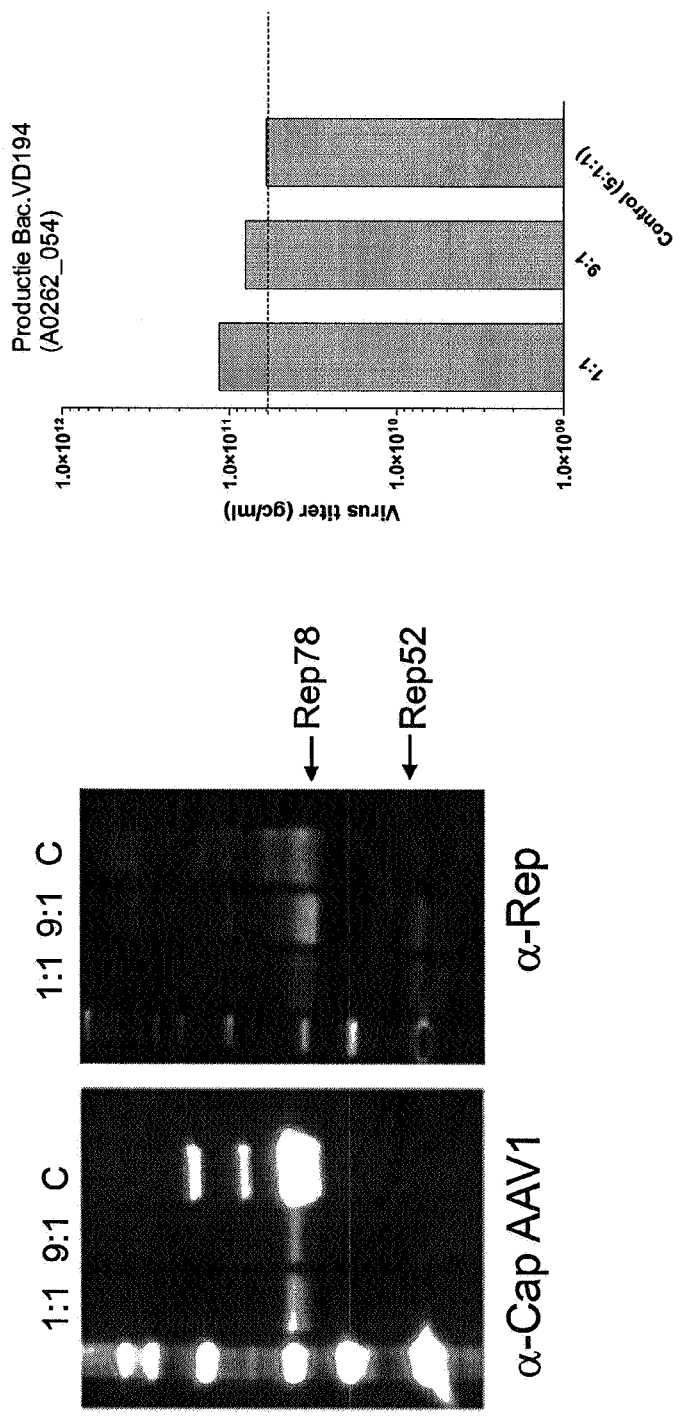
FIG. 11A shows Western blot analysis of Cap and Rep proteins expressed from Bac.VD194, three days after infection with the baculovirus ratios 1:1 and 5:1. (C=Bac.VD88: Bac.VD84:Bac.VD43 at 5:1:1, respectively).
FIG. 11B shows the viral titers for the same productions analyzed in FIG. 11A.

For Bac.VD194, Western blot analysis was carried out to determine the Rep and Cap expression. Accordingly, three days after cells were infected with 2 different baculovirus ratios (i.e., 1:1 and 9:1, with 5:1:1 for the three component control) cell lysates were harvested and subjected to Western blot analysis. As shown in FIG. 11A, the Cap expression is low in the production with the 1:1 baculovirus ratio, but the production with the 9:1 ratio is comparable to the three component control. However, for the 1:1 and 9:1 ratio productions, Rep expression is dramatically reduced as compared to the three component control. FIG. 11B, however, shows that the production of virus was greater in the productions with Bac.VD194. The fact that the production is higher, yet the Cap expression is lower indicates a more favourable total:full ratio. Again, the conclusion is that the two component system with equimolar amounts of Rep and Cap, in particular with high Rep and moderate Cap expression, leads to a lower total:full ratio (i.e., a greater percentage of filled particles).

Example 2

Materials and Methods

Three shaker flasks (all cultivated at 28° C. prior to infection) were inoculated with inoculum P5; 4 mL Bac.VD43, 4 mL Bac.VD84 and 20 mL Bac.VD88. Shakers were incubated during the 72 hour viral production at three different temperatures (26, 28 and 30° C.).

The lysis treatment of all shaker flasks was carried out within 1 shaker incubator using 0.9% (v/v) Triton X-100. After lysis buffer addition, shakers were incubated for 30 minutes at setpoint 28° C., benzonase was added (16 μL per 400 mL) and shakers were incubated for 1 hour at setpoint 37° C. After benzonase treatment, all shaker flasks were placed for viral clearance overnight at 29° C., followed by storage at 4° C. for maximal 3 days.

Out of each shaker incubator, 200 ml of crude lysed bulk was processed on a 1 mL affinity column using a flow rate of 1 mL/min After washing, the product was eluted using PBS, pH 3.5.

Results

The in-process cell count of the shaker flasks used for the temperature study are show in Table 3. An increase of temperature correlates with a decrease of total cell concentration and viability at the time of harvest. The viability obtained at 28° C. was comparable to the results obtained with the Wave bioreactor system.

TABLE 3

In process cell counts shaker productions

| Shaker flask (lot nr) | Prior to infection | | Prior to lysis buffer addition | |
|---|---|---|---|---|
| | Total cell conc. (#/mL) | Viability (%) | Total cell conc. (#/mL) | Viability (%) |
| Shaker flask infection temperature 26° C. (Lot nr 0078) | $1.89 \times 10^6$ | 99.5 | $2.74 \times 10^6$ | 85.7 |
| Shaker flask infection temperature 28° C. (Lot nr 0078) | $1.89 \times 10^6$ | 99.5 | $2.51 \times 10^6$ | 74.9 |
| Shaker flask infection temperature 30° C. (Lot nr 0078) | $1.89 \times 10^6$ | 99.5 | $2.42 \times 10^6$ | 61.0 |

The test results of the crude lysed bulks and eluates of the shaker flasks are shown in Table 4.

TABLE 4

Total:full ratio of rAAV particles produced at different temperatures

| Shaker flask (lot nr) | Total particles (tp/mL) HPLC method | Q-PCR CLB (gc/mL) | Q-PCR Eluate (gc/mL) | Ratio total: full (tp/gc) |
|---|---|---|---|---|
| Shaker flask 26° C. (Lot nr 0078) | $6.14 \times 10^{12}$ | $1.28 \times 10^{10}$ | $5.52 \times 10^{10}$ | 111 |
| Shaker flask 28° C. (Lot nr 0078) | $6.58 \times 10^{12}$ | $2.00 \times 10^{10}$ | $1.43 \times 10^{11}$ | 46 |
| Shaker flask 30° C. (Lot nr 0078) | $7.24 \times 10^{12}$ | $3.94 \times 10^{10}$ | $1.73 \times 10^{11}$ | 42 |

DISCUSSION AND CONCLUSION

Increasing the temperature during rAAV production in SF+ cells, slightly increases the total amount of rAAV particles that are produced, but increases the amount of full particles that are produced more, leading to an decreased total:full ratio.

What is claimed is:

1. A method for the production of a recombinant parvoviral virion which decreases the total:full virion particle ratio, wherein the method comprises culturing an insect cell comprising one or more nucleic acid constructs which comprise:

(a) a nucleotide sequence comprising a transgene that is flanked by at least one parvoviral inverted terminal repeat (ITR) nucleotide sequence;

(b) a first expression cassette comprising a nucleotide sequence encoding parvoviral Rep proteins Rep78 and Rep52, which nucleotide sequence is operably linked to a first promoter that is capable of driving expression of the Rep78 and Rep52 proteins in the insect cell and wherein the nucleotide sequence encoding the parvoviral Rep proteins is a single open reading frame encoding Rep78 and Rep52 proteins; and (c) a second expression cassette comprising a nucleotide sequence encoding parvoviral capsid proteins which is operably linked to a second promoter that is capable of driving expression of the capsid proteins in the insect cell;

under conditions conducive to the expression of the Rep proteins and the capsid proteins wherein expression of the Rep 78 and Rep52 proteins is greater than expression of the capsid proteins; wherein (i) the first and second expression cassettes are present on a single nucleic acid construct and are present in equimolar amounts in the insect cell, (ii) the ratio of the expression of Rep78 and Rep52 proteins to the expression of capsid proteins is regulated by one or more of the following structures or conditions:

(A) the first promoter is stronger than the second promoter;

(B) more and/or stronger enhancer elements are present in the first expression cassette as compared to the second expression cassette;

(C) the nucleotide sequence encoding the Rep78 and the Rep52 proteins has a higher codon adaptation index compared to the nucleotide sequence encoding the capsid proteins;

(D) the Rep78 and the Rep52 proteins are temperature optimized;

(E) the Rep78 and the Rep52 proteins are variants with altered amino acid sequences as compared to the sequences of corresponding wild-type Rep78 and Rep52 proteins, wherein the altered sequences result in increased Rep78 and Rep52 protein function manifest as increased adeno-associated virus (AAV) production in the insect cell; and/or (F) the first promoter is as strong as the second promoter, one or more of structures or conditions (B)-(E) is present, and the insect cell comprises an additional nucleotide sequence encoding for an additional Rep protein, resulting in expression of the Rep78 and Rep52 proteins that is greater than expression of the capsid proteins, thereby decreasing the total:full virion particle ratio compared to a method in which the expression of the Rep78 and the Rep52 proteins is not greater than the expression of the capsid proteins.

2. The method according to claim 1, wherein the initiation codon for translation of the parvoviral Rep78 protein is a suboptimal initiation codon.

3. The method according to claim 2, wherein the suboptimal initiation codon is selected from the group consisting of ACG, TTG, CTG and GTG.

4. The method according to claim 3, wherein the suboptimal initiation codon is ACG or CTG.

5. The method according to claim 1, wherein possible false translation initiation sites in the Rep protein coding sequences other than the Rep78 and Rep52 translation initiation sites, are eliminated.

6. The method according to claim 1, wherein the nucleotide sequence encoding the parvoviral capsid proteins of (c) comprises an open reading frame (ORF) comprising nucleotide sequences encoding the VP1, VP2 and VP3 capsid proteins.

7. The method according to claim 6, wherein (i) at least one ORF comprising nucleotide sequences encoding VP1, VP2 or VP3 capsid proteins does not comprise an artificial intron, or (ii) at least one ORF comprising a nucleotide sequence encoding said Rep78 and Rep52 proteins does not comprise an artificial intron.

8. The method according to claim 7, wherein:

(A) no ORF comprising nucleotide sequences encoding the VP1, VP2 and VP3 capsid proteins comprises an artificial intron; and/or (B) no ORF comprising nucleotide sequences encoding said Rep78 and Rep52 proteins comprises an artificial intron.

9. The method according to claim 1, wherein the first promoter or the second promoter is selected from the group consisting of (a) a PolH promoter,
(b) p10 promoter,
(c) a basic promoter,
(d) an inducible promoter,
(e) an E1 promoter, and
(f) a deltaE1 promoter.

10. The method according to claim 9, wherein (a) the first promoter is:
  (i) a PolH promoter,
  (ii) p10 promoter or
  (iii) basic promoter, and
(b) the second promoter is:
  (i) a deltaE1 promoter or
  (ii) an E1 promoter.

11. The method according to claim 1, wherein the first expression cassette comprises at least one baculovirus enhancer element and/or at least one ecdysone responsive element.

12. The method according to claim 11, wherein the enhancer element is selected from the group consisting of hr1, hr2, hr3, hr4 and hr5.

13. The method according to claim 1, wherein the parvoviral ITR sequence, the parvoviral Rep78 and Rep52 proteins and/or the parvoviral capsid proteins are from an AAV.

14. The method according to claim 1, further comprising a step of recovering the recombinant parvoviral virion from the culture.

15. A nucleic acid construct comprising a first and a second expression cassette as defined in claim 1, wherein:

(a) the first promoter is a p10 promoter and the second promoter is a PolH promoter or a 4×Hsp27 EcRE+minimal Hsp70 promoter;

(b) the first promoter is a PolH promoter and the second promoter is a deltaIE1 or an IE1 promoter;

(c) the first promoter is a p10 promoter and the second promoter is a deltaIE1 or an IE1 promoter; or (d) the first promoter is a PolH promoter and the second promoter is a PolH promoter, and wherein the first expression cassette optionally comprises an enhancer element.

16. A kit comprising (a) a first nucleic acid construct comprising:
  (i) a first expression cassette comprising a nucleotide sequence encoding parvoviral Rep proteins Rep78 and Rep52 which is operably linked to a first promoter that is capable of driving expression of the Rep78 or Rep52 protein in a host insect cell and wherein the nucleotide sequence encoding the parvoviral Rep protein is a single open reading frame encoding Rep78 and Rep52 proteins; and
  (ii) a second expression cassette comprising a nucleotide sequence encoding parvoviral capsid proteins which is operably linked to a second promoter that is capable of driving expression of the capsid proteins in the insect cell;

wherein expression of Rep78 and Rep52 proteins in insect cells is regulated by one or more of the following structures or conditions:
  (A) the first promoter is stronger than the second promoter;
  (B) the first expression cassette comprises more and/or stronger enhancer elements as compared to the second expression cassette;
  (C) the nucleotide sequence encoding the Rep78 and the Rep52 proteins has a higher codon adaptation index compared to the nucleotide sequence encoding the capsid proteins;
  (D) the Rep78 and the Rep52 proteins are temperature optimized;
  (E) the Rep78 and the Rep52 proteins are variants with altered amino acid sequences as compared to the sequences of corresponding wild-type Rep78 and Rep52 proteins, wherein the altered sequences result in increased Rep78 and Rep52 protein function manifest as increased adeno-associated virus (AAV) production in the insect cell; and/or
  (F) the first promoter is as strong as the second promoter and one or more of structures or conditions (B)-(E) is present;
  such that, when expressed in the insect cell, expression of the Rep78 and the Rep52 proteins is greater than expression of the capsid proteins,
  which decreases the total:full virion particle ratio compared to a method in which the expression of the Rep78 and the Rep52 proteins is not greater than the expression of the capsid proteins,
  wherein when the first promoter is as strong as the second promoter and one or more of (B)-(E) is present, then the insect cell comprises an additional nucleotide sequence encoding an additional Rep protein, and
  (b) a second nucleic acid construct comprising a nucleotide sequence encoding a multiple cloning site for a transgene, which site is flanked by at least one parvoviral ITR nucleotide sequence, and which transgene is operably linked to a promoter capable of driving its expression in a host insect cell.

17. The kit according to claim 16, wherein the initiation codon for translation of the parvoviral Rep78 protein is a suboptimal initiation codon.

18. The kit according to claim 17, wherein the suboptimal initiation codon is selected from the group consisting of ACG, TTG, CTG and GTG.

19. The kit according to claim 18, wherein the suboptimal initiation codon is ACG or CTG.

20. The kit according to claim 16, wherein possible false translation initiation sites in the Rep protein coding sequences other than the Rep78 and Rep52 translation initiation sites, are eliminated.

21. An insect cell comprising one or more nucleic acid constructs, which comprise:
  (a) a nucleotide sequence comprising a transgene that is flanked by at least one parvoviral ITR nucleotide sequence;
  (b) a first expression cassette comprising a nucleotide sequence encoding parvoviral Rep proteins Rep78 and Rep52, which nucleotide sequence is operably linked to a first promoter that is capable of driving expression of the Rep78 and Rep52 proteins in the insect cell and wherein the nucleotide sequence encoding the parvoviral Rep proteins is a single open reading frame encoding Rep78 and Rep52 proteins; and
  (c) a second expression cassette comprising a nucleotide sequence encoding parvoviral capsid proteins which is operably linked to a second promoter that is capable of driving expression of the capsid proteins in the insect cell;
  wherein
  (i) the first and second expression cassettes are present on a single nucleic acid construct and are present in equimolar amounts in the insect cell, and
  (ii) the ratio of the expression of Rep78 and Rep52 proteins to the expression of capsid proteins in said cell is regulated by one or more of the following structures or conditions:
  (A) the first promoter is stronger than the second promoter;
  (B) more and/or stronger enhancer elements are present in the first expression cassette as compared to the second expression cassette;
  (C) the nucleotide sequence encoding the Rep78 and the Rep52 proteins has a higher codon adaptation index compared to the nucleotide sequence encoding the capsid proteins;
  (D) the Rep78 and the Rep52 proteins are temperature optimized;
  (E) the Rep78 and the Rep52 proteins are variants with altered amino acid sequences as compared to the sequences of corresponding wild-type Rep78 and Rep52 proteins, wherein the altered sequences result in increased Rep78 and Rep52 protein function manifest as increased adeno-associated virus (AAV) production in the insect cell; and/or
  (F) the first promoter is as strong as the second promoter, one or more of structures or conditions (B)-(E) is present, and the insect cell comprises an additional nucleotide sequence encoding for an additional Rep protein,
  such that, when expressed in the insect cell, expression of the Rep78 and Rep52 proteins is greater than expression of the capsid proteins,
  which decreases the total:full virion particle ratio compared to a method in which the expression of the Rep78 and the Rep52 proteins is not greater than the expression of the capsid proteins.

22. The insect cell according to claim 21, wherein the initiation codon for translation of the parvoviral Rep78 protein is a suboptimal initiation codon.

23. The insect cell according to claim 22, wherein the suboptimal initiation codon is selected from the group consisting of ACG, TTG, CTG and GTG.

24. The insect cell according to claim 23, wherein the suboptimal initiation codon is ACG or CTG.

25. The insect cell according to claim 21, wherein possible false translation initiation sites in the Rep protein coding sequences other than the Rep78 and Rep52 translation initiation sites, are eliminated.

* * * * *